United States Patent
Lee

(10) Patent No.: US 8,557,250 B2
(45) Date of Patent: Oct. 15, 2013

(54) METHODS FOR PREPARING COMPLEX MULTIVALENT IMMUNOGENIC CONJUGATES

(75) Inventor: Che-Hung Robert Lee, Silver Spring, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/440,856

(22) Filed: Apr. 5, 2012

(65) Prior Publication Data

US 2012/0195922 A1 Aug. 2, 2012

Related U.S. Application Data

(60) Division of application No. 12/283,894, filed on Sep. 15, 2008, now Pat. No. 8,173,135, which is a continuation-in-part of application No. PCT/US2007/006627, filed on Mar. 16, 2007.

(60) Provisional application No. 60/783,490, filed on Mar. 17, 2006.

(51) Int. Cl.
  *A61K 39/395* (2006.01)
  *A61K 39/02* (2006.01)
  *A61K 39/00* (2006.01)

(52) U.S. Cl.
  USPC ............. 424/197.11; 424/184.1; 424/193.1; 424/203.1; 424/234.1

(58) Field of Classification Search
  USPC ......... 424/184.1, 193.1, 197.11, 203.1, 234.1
  See application file for complete search history.

(56) References Cited

U.S. PATENT DOCUMENTS

| | | | |
|---|---|---|---|
| 4,963,232 A | 10/1990 | Kuriyama et al. | |
| 5,066,408 A | 11/1991 | Powell | |
| 5,480,643 A | 1/1996 | Donovan et al. | |
| 5,651,971 A | 7/1997 | Lees | |
| 5,849,301 A | 12/1998 | Lees | |
| 5,965,714 A | 10/1999 | Ryall | |
| 6,800,728 B2 | 10/2004 | Schwartz | |
| 2004/0096461 A1 | 5/2004 | Michon et al. | |
| 2004/0151733 A1 | 8/2004 | Livingston et al. | |
| 2005/0002948 A1 | 1/2005 | Ryall | |
| 2005/0002957 A1 | 1/2005 | Ryall | |
| 2005/0019337 A1 | 1/2005 | Ryall | |
| 2007/0110762 A1 | 5/2007 | Jessouroun et al. | |
| 2007/0141084 A1 | 6/2007 | Lee et al. | |

FOREIGN PATENT DOCUMENTS

| WO | WO 99/42130 | 8/1999 |
|---|---|---|
| WO | WO 00/04922 | 2/2000 |
| WO | WO 02/058737 A2 | 8/2002 |
| WO | WO 03/007985 A2 | 1/2003 |
| WO | WO 2005/014037 A2 | 2/2005 |
| WO | WO 2005/037320 A2 | 4/2005 |
| WO | WO 2005/117965 A1 | 12/2005 |
| WO | WO 2006/077397 A2 | 7/2006 |

OTHER PUBLICATIONS

Behr et al., "Asymmetric synthesis of potent glycosidase and very potent α-mannosidase inhibitors: 4-amino-4-deoxy-L-erythrose and 4-amino-4,5-dideoxy-L-ribose," *Tetrahedron* 59:543-553, 2003.

Carmenate et al. "Effect of conjugation methodology on the immunogenicity and protective efficacy of meningococcal group C polysaccharide-P64k protein conjuates," *FEMS Immunology and Medical Microbiology* 40:193-199, 2004.

Chu et al. "Further Studies on the Immunogenicity of *Haemophilus influenza* Type b and Pneumococcal Type 6A Polysaccharide-Protein Conjugates," *Infection and Immunity* 40(1):245-256, 1983.

Gupta et al., "Comparativbe Immunogenicity of Conjugates Composed of *Escherichia coli* O111 O-Specific Polysaccharide, prepared by Treatment with Acetic Acid or Hydrazine, Bount to Tetanus Toxoid by Two Synthetic Schemes," *Infection and Immunity* 63(8):2805-2810, 1995.

King et al., "Preparation of Protein Conjugates via Intermolecular Hydrazone Linkage," *Biochemistry* 25(19):5774-5779, 1986.

Konadu et al., "Preparation, Characterization, and Immunological Properties in Mice of *Escherichia coli* O157 O-Specific Polysaccharide-Protein Conjugate Vaccines," *Infection and Immunity* 62(11):5048-5054, 1994.

Lee et al., "Combined synthesis of multi-valent conjugate vaccines," *12th Annual FDA Science Forum*, Apr. 18-20, 2006 (Abstract).

Lee, "Quality Control of Polyvalent Pheumococcal Polysaccharide-Protein Conjugate Vaccine by Nephelometry," *Biologicals* 30:97/103, 2002.

Shen et al., "Group B *Streptococcus* Capsular Polysaccharide-Cholera Toxin B Subunit Conjugate Vaccines Prepared by Different Methods for Intranasal Immunization," *Infection and Immunity* 69(1):297-306, 2001.

International Search Report from PCT/US2007/006627 dated Aug. 30, 2007.

Non-Final Office Action from U.S. Appl. No. 10/566,898 dated Oct. 7, 2009.

Non-Final Office Action from U.S. Appl. No. 10/566,899 dated Jun. 25, 2010.

Laferriere et al., "The synthesis of Streptococcus pneumonia polysaccharide-tetanus toxoid conjugates and the effect of chain length on immunogenicity," *Vaccine* 15(2):179-186, Feb. 1997.

Lees et al., "Activation of soluble polusaccharides with 1-cyano-4-dimethylaminopyridinium tetrafluoroborate for use in protein-polysaccharide conjugate vaccines and immunological reagents," *Vaccine* 14(3):190-198, Feb. 1996.

*Primary Examiner* — Rodney P. Swartz
(74) *Attorney, Agent, or Firm* — Klarquist Sparkman, LLP

(57) ABSTRACT

Methods for preparing complex multivalent immunogenic conjugates that include simultaneously reacting a plurality or immunogenic-distinct polysaccharides with at least one protein to make the complex multivalent immunogenic conjugates. The simultaneous reaction involves reaction of a hydrazide group on one reactant with an aldehyde or cyanate ester group on the other reactant.

27 Claims, 15 Drawing Sheets

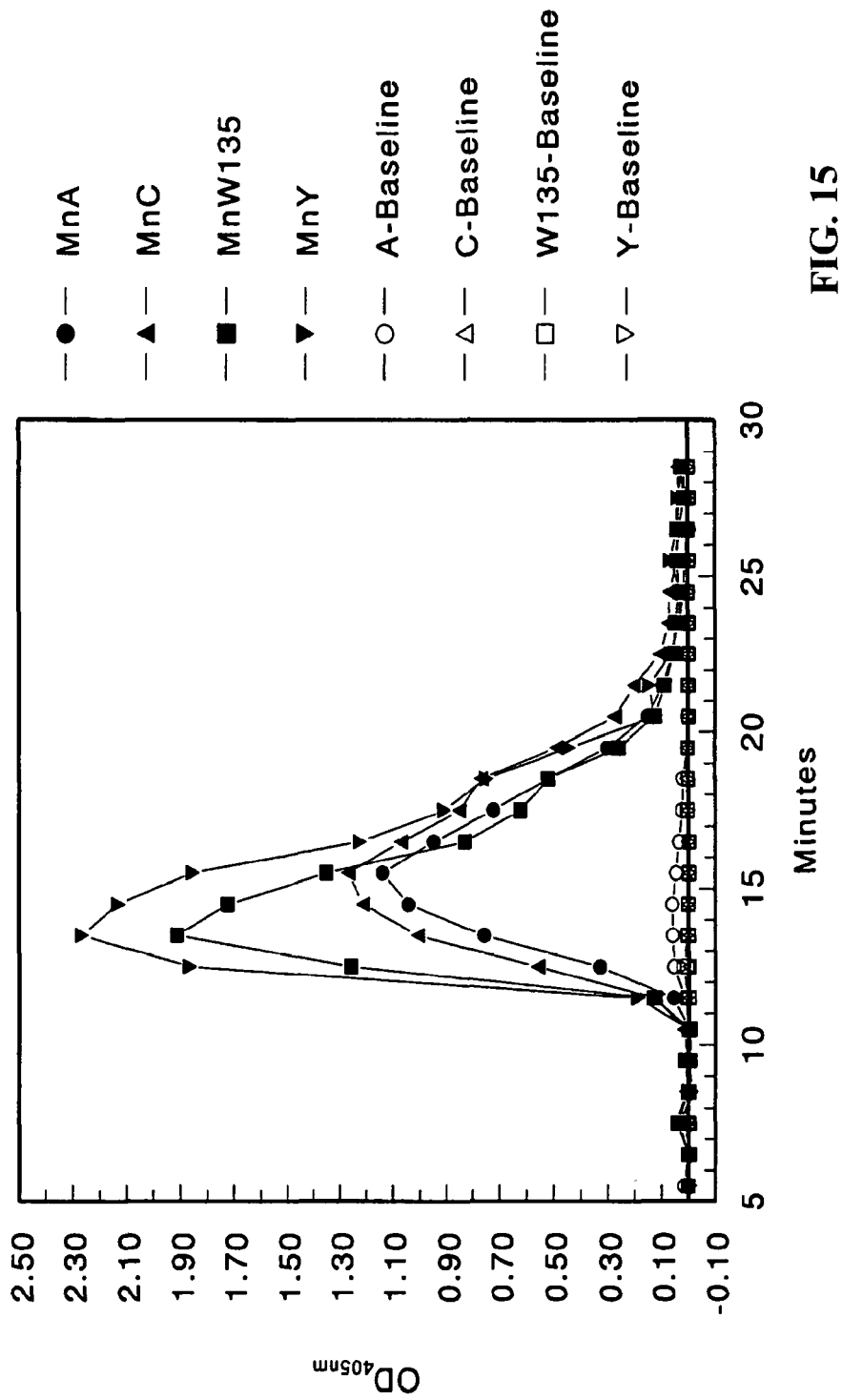

METHODS FOR PREPARING COMPLEX MULTIVALENT IMMUNOGENIC CONJUGATES

PRIORITY CLAIM

This application is a divisional application of U.S. application Ser. No. 12/283,894, filed Sep. 15, 2008, issued as U.S. Pat. No. 8,173,135, which is a continuation-in-part of International Application No. PCT/US2007/006627, filed Mar. 16, 2007, which claims the benefit of U.S. Provisional Application No. 60/783,490, filed Mar. 17, 2006, both of which are incorporated herein by reference in their entireties.

CROSS-REFERENCE TO RELATED APPLICATIONS

This application relates to WO 2005/014037 filed Aug. 6, 2004, and WO 2005/037320, filed Aug. 6, 2004, both of which are incorporated herein by reference in their entireties.

FIELD

The present disclosure relates to methods for making multivalent immunogenic conjugates, and the conjugates made from such methods.

BACKGROUND

Bacterial polysaccharides (PSs) are T-independent antigens inducing short-term immunity in older children and adults, but frequently not in young infants. PSs are incapable of binding to the major histocompatibility complex molecules, which is required for antigen presentation to and stimulation of T-helper lymphocytes. PSs are able to stimulate B lymphocytes for antibody production without the help of T-helper lymphocytes. As a result of the T-independent stimulation of the B lymphocytes, there is a lack of memory induction following immunization by these antigens.

T-independent polysaccharide antigens can be converted to T-dependent antigens by covalent attachment of the polysaccharides to protein molecules. B cells that bind the polysaccharide component of the conjugate vaccine can be activated by helper T cells specific for peptides that are a part of the conjugated carrier protein. The T-helper response to the carrier protein serves to augment the antibody production to the polysaccharide. PS-conjugate vaccines are polysaccharide-protein hybrids formed by the covalent attachment of a protein to a PS. Chemical modification of the PS prior to attachment is typically required because most native bacterial PSs cannot be chemically linked to a protein without first undergoing some chemical modification ("activation").

Attachment to the protein renders the PSs to have an access to the immune property of a number of T cell epitopes of the protein. These T cell epitopes interact with CD4 helper T cells, greatly facilitating an antibody response to the attached polysaccharide. The T helper cell-dependent response to a conjugate results in both serum IgG antibodies and immune memory, even in infants, such as infants less than two years age. Additionally, the immunogenicity of the PS-conjugate, in contrast to the native PS, is less dependent on the size of the conjugated PS. Accordingly, conjugates prepared with either PS or oligosaccharides can have similar immunogenicity.

There are many conjugation reactions that have been employed for covalently linking polysaccharides to proteins. Three of the more commonly employed methods include: 1) reductive amination, wherein the aldehyde or ketone group on one component of the reaction reacts with the amino or hydrazide group on the other component, and the C=N double bond formed is subsequently reduced to C—N single bond by a reducing agent; 2) cyanylation conjugation, wherein the polysaccharide is activated either by cyanogens bromide (CNBr) or by 1-cyano-4-dimethylammoniumpyridinium tetrafluoroborate (CDAP) to introduce a cyanate group to the hydroxyl group, which forms a covalent bond to the amino or hydrazide group upon addition of the protein component; and 3) a carbodiimide reaction, wherein carbodiimide activates the carboxyl group on one component of the conjugation reaction, and the activated carbonyl group reacts with the amino or hydrazide group on the other component. These reactions are also frequently employed to activate the components of the conjugate prior to the conjugation reaction.

The *Haemophilus influenzae* type b (Hib) conjugate vaccines represent the first PS-protein conjugate vaccines produced for clinical use. Robbins and his colleagues in 1980 utilized the biotechnological process of chemically attaching Hib saccharides to protein carriers, a concept developed 50 years earlier. See Avery et al., J. Exp. Med. 1929; 50:533-SSO; Schneerson et al., J. Exp. Med. 1980; 152:361-376. There are now four different Hib conjugate vaccines licensed in the United States, each different, and each having their own physical, chemical, and immunological characteristics, as summarized in Table A. A detailed review of the conjugation chemistry and quality control used in these vaccines has been published. See Kniskem et al., "(Conjugation: design, chemistry, and analysis" in Ellis et al., Development and clinical uses of *Haemophilus* b conjugate vaccines. New York: Marcel Dekker. 1994: 37-69.

TABLE A

| Vaccine | Saccharide size | Carrier protein | Spacer (linker) |
| --- | --- | --- | --- |
| PRP-D (Connaught) | Polysaccharide | Diphtheria toxoid | 6-carbon spacer (ADH) |
| HbOC (Wyeth-Dederle) | Oligosaccharide | Diphtheria protein (CRM) | None (amide) |
| PRP-OMPC (Merck) | Small polysaccharide | Meningococcal protein | Thioether (bigeneric) |
| PRP-T (Aventis Pasteur) | Polysaccharide | Tetanus toxoid | 6-carbon spacer (ADH) |

The first commercial Hib conjugate, polyribosylribitol phosphate diphtheria toxoid conjugate (PRP-D), consists of partially size-reduced Hib PS attached through a six-carbon spacer, adipic acid dihydrazide (ADH) to diphtheria toxoid using the procedure of Schneerson et al., J. Exp. Med. 1980; 152:361-376. The ADH derivative of diphtheria toxoid was obtained in this method by reaction with ADH in the presence of 1-[3-(dimethylamino)propyl]-3-ethyl carbodiimide hydrochloride (EDC). The Hib PS was then activated by creating cyanate groups on the hydroxyl groups using CNBr. The activated PS was conjugated to the ADH-toxoid (cyanylation conjugation), but the process created an unstable linkage and the conjugate had solubility problems.

The Robbins conjugation chemistry was later modified such that the ADH spacer is added first to the polysaccharide, which is then conjugated to the purified protein in the presence of EDC (carbodiimide reaction). See Chu et al., Infect. Immun 1983; 40:245-256; Schneerson et al. Infect. Immun. 1986, 52:519-528. This modification improved the conjugation efficiency and product solubility. The vaccine polyribosylribitol phosphate tetanus protein conjugate (PRP-T) utilizes the improved chemistry to covalently link Hib polysaccharide to tetanus toxoid (see Table A).

The polyribosylribitol phosphate cross-reacting mutant diphtheria toxoid conjugate (PRP-CRM) vaccine, also referred to as *Haemophilus* b oligosaccharide conjugate (HbOC), does not contain Hib PS. Instead, it utilizes oligosaccharides of about 20 repeat units derived by periodate oxidation of the glycol functionality in the ribitol moiety. The oxidized oligosaccharides are then attached directly to $CRM_{197}$ a nontoxic mutant form of diphtheria toxin in the presence of sodium cyanoborohydride (reductive amination). See Anderson et al., J. Immunol. 1989; 142:2464-8; and Anderson, Infect. Immun. 1983, 39:233-238. In this conjugation method, the ratio of oligosaccharide to protein was found to be critical for optimal antibody response. See Kniskern et al., "Conjugation: design, chemistry, and analysis" in Ellis et al., Development and clinical uses of *Haemophilus* b conjugate vaccines. New York: Marcel Dekker, 1994: 37-69; Anderson et al., J. Immunol. 1989; 142:2464-8.

Compared to the other Hib conjugate vaccines, Hib polysaccharide—*Neisseria meningitidis* outer membrane protein complex conjugate vaccine (PRP-OMPC) has a number of unique properties. The protein carrier is not a component of the diphtheria, tetanus, and pertussis (DTP) vaccine, but consists of lipopolysaccharide-depleted meningococcal outer membrane vesicles to which are attached size-reduced Hib PS through a thioether linkage. See Marburg et al., J. Amer. Chem. Soc. 1986; 108:5282-5287; Kniskern et al., "Conjugation: design, chemistry, and analysis" in Ellis et al., Development and clinical uses of *Haemophilus* b conjugate vaccines. New York: Marcel Dekker, 1994: 37-69; Anderson et al., J. Immunol. 1989; 142:2464-8. In this process, separate linkers are attached to both the protein and Hib polysaccharide, followed by fusion of the linkers to form a thioether linkage.

*Neisseria meningitidis* is a leading cause of bacterial meningitis and sepsis throughout the world. Pathogenic meningococci are enveloped by a polysaccharide capsule that is attached to the outer membrane surface of the organism. Thirteen different serogroups of meningococci have been identified on the basis of the immunological specificity of the capsular polysaccharide (Frasch, C. E., et. al. 1985). Of these thirteen serogroups, five cause the majority of meningococcal disease; these include serogroups A, B, C, W135, and Y. Serogroup A is responsible for most epidemic disease. Serogroups B, C, and Y cause the majority of endemic disease and localized outbreaks. Host defense of invasive meningococci is dependent upon complement-mediated bacteriolysis. The serum antibodies that are responsible for complement-mediated bacteriolysis are directed in large part against the outer capsular polysaccharide.

Conventional vaccines based on meningococcal polysaccharide elicit an immune response against the capsular polysaccharide. These antibodies are capable of complement-mediated bacteriolysis of the serogroup specific meningococci. The meningococcal polysaccharide vaccines were shown to be efficacious in children and adults. However, efficacy was limited in infants and young children, and subsequent doses of the polysaccharide in younger populations elicited a weak or no booster response.

There are a number of approaches that have been employed for activation of the meningococcal PS and for conjugation, as summarized in Table B. Each mode of activation has the potential to alter important epitopes, even when relatively few sites are activated on the PS molecule. Periodate activation of the group C meningococcal PS, for example, results in chain breakage generating smaller saccharide units with terminal aldehyde groups that can be linked to the protein via reductive amination. Richmond et al., J. Infect. Dis. 1999; 179:1569-72.

TABLE B

| Method | Saccharide size | Carrier protein | Spacer | Procedure | Used in humans |
|---|---|---|---|---|---|
| #1 Reductive amination | Reduced | Tetanus toxoid | None | Aldehyde form of PS combined with protein in presence of sodium cyanoborohydride | No |
| #2 Carbodiimide | Native | Tetanus toxoid | None | PS and protein combined in presence of carbodiimide, then blocked with ethanolamine | No |
| #3 Active ester[a] | Oligosaccharide | $CRM_{197}$ | Adipic acid | Animated reducing terminus of the oligosaccharide conjugate to protein by adipic acid $(NHS)_2$ | Yes |
| #4 Reductive amination | Reduced | $CRM_{197}$ | None | Aldehyde form of combined with protein in presence of sodium cyanoborohydride | Yes |
| #5 Reductive Amination | De-OAc-PS[b] | Tetanus toxoid | None | Aldehyde form of PS combined with protein in presence of sodium cyanoborohydride | Yes |

[a]Hydroxysuccinimide diester of adipic acid
[b]Deacetylylate PS only reported for Meningococcal group C Initial studies on production and optimization of meningococcal group C conjugates were reported well before commercialization of the Hib conjugates. See Beuvery et al., Infect. Immun. 1982; 37:15-22; Beuvery et al., Infect. Immun. 1983; 40:39-45; Beuvery et al., J. Infect. 1983; 6:247-55; Jennings, et al., J. Immunol. 1981; 127:1011-8.

Two different conjugation methodologies have been reported for chemically linking the group C PS to a protein carrier. See Jennings et al., J. Immunol. 1981; 127:1011-8; Beuvery et al., Infect. Immun. 1983; 40:39-45. The first approach employs partially depolymerized PS, which is activated by creation of terminal aldehyde groups through periodate oxidation (Method #1 in Table B). The aldehydes are then reacted through reductive amination with free amino groups on the protein, mostly lysines, in the presence of sodium cyanoborohydride. See Jennings et al., J Immunol 1981; 127:1011-8. In this method, activation occurs at one specific site of de-0 acetylation on the group C PS.

The second approach utilizes the carbodiimide reaction (Method #2 in Table B) to covalently link carboxylic groups in the high molecular weight PS to lysine ε-amino groups on the carrier protein. The activation sites in this method are more random, compared to periodate activation.

Group C meningococcal conjugates prepared by these two methods have been evaluated in animals. See Beuvery et al., Dev. Biol. Stand. 1986; 65:197-204; and Beuvery et al., J. Infect. 1983; 6:247-55. The conjugates stimulated both T cell independent and T cell dependent responses upon initial immunization. See Beuvery et al., J. Infect. 1983; 6:247-55. Studies have shown that the PS must, however, be covalently linked to the carrier protein to induce a T cell dependent antibody response.

The first group A and group C meningococcal conjugates to be used in clinical trials were prepared by Chiron Vaccines and were reported in 1992 (Method #3 in Table B). See Costantino et al., Vaccine 1992; 10:691-8. The conjugation method was based upon selective terminal group activation of small oligosaccharides produced by mild acid hydrolysis followed by coupling to a protein through a hydrocarbon spacer. The non-toxic mutant of diphtheria toxin, CRM, was used as the protein carrier. To activate the oligosaccharides for conjugation, an amino group was added to the end of the oligosaccharide, and then reacted with the N-hydroxysuccinimide diester of adipic acid to create an active ester. This active ester was then covalently bound to lysine ε-amino groups in the $CRM_{197}$ protein, creating the conjugate.

Conventional methods for the preparation of PS-protein conjugate vaccines do not use hydrazide chemistry in the reductive amination conjugation reaction, even though hydrazide in the form of ADH has been used in activating polysaccharide. These prior art methods utilize ε-amino groups of lysine residues on the protein to react with functional groups on activated PSs, such as aldehyde groups (reductive amination) and carboxyl groups. The efficiency of the reaction is low, typically only about 20%. The reaction also requires two to three days for the conjugation to be completed, necessitating the use of purification steps to separate the conjugate from unreacted PS. See Guo et al. "Protein-polysaccharide conjugation" in: Pollard et al., Methods in Molecular Medicine, Vol. 66: Meningococcal Vaccines: methods and Protocols, Humana Press, Totowa, N.J., 2001, pg 49-54. There are a number of explanations that have been proposed for the low yields observed. First, the £-amino group of lysine (pKa=10.5) has low reactivity at the conjugation conditions (pH 6.5-7.4). See Inman et al., Biochemistry 1969; 8:4074-4082 Secondly, most conjugation methods employ toxoids as the carrier proteins. The toxoids are derived from toxins by detoxification with formaldehyde, which combines with the amino groups of the toxins, leaving a limited numbers of amino groups available for conjugation. Thirdly, reduced solubility of the resulting activated protein and protein-PS conjugate can lead to precipitation.

Accordingly, methods for the synthesis and manufacture of polysaccharide-protein conjugate vaccines in high yields are desirable. Also desirable are methods wherein the reaction proceeds at a rapid rate, with reduced production of undesired by-products, and with reduced amounts of unreacted protein and polysaccharide remaining at the end of the reaction.

Existing vaccines based on PSs are of limited use in young children and do not provide long-lasting protection in adults. Thus, a need exists for a protein-PS conjugate vaccine capable of conferring long term protection against diseases in children and adults at risk for, e.g., bacterial meningitis, pneumonia, tetanus, and other bacterial infections. The protein-PS conjugates of the preferred embodiment can be employed to prepare vaccine formulations capable of conferring long term protection to infants, children, and adults.

Administration of multi-valent (or combination) vaccines, which contain multiple vaccines, has become more prevalent recently due to economic and logistic advantages as well as better patient compliance in field application. Similar trends are occurring for conjugate vaccines. Typical examples of such combination conjugate vaccine are Prevnar (Wyeth Lederle), the 7-valent pneumococcal conjugate vaccine, and Menactra (Aventis Pasteur), the tetravalent meningococcal conjugate vaccine.

SUMMARY

Described herein are methods for making complex multivalent immunogenic conjugates, including conjugate vaccines.

In one embodiment, there is described a method for making a complex multivalent immunogenic conjugate, comprising:

reacting a plurality of immunogenic-distinct polysaccharides with an oxidizing agent resulting in a mixture of a plurality of aldehyde-activated immunogenic-distinct polysaccharides;

reacting at least one protein with hydrazine, carbohydrazide, hydrazine chloride, a dihydrazide or a mixture thereof under conditions sufficient to produce a solution of at least one hydrazide-activated protein;

contacting the mixture of the plurality of aldehyde-activated immunogenic-distinct polysaccharides with the at least one hydrazide-activated protein at a pH of about 5 to about 8 such that the plurality of aldehyde-activated immunogenic-distinct polysaccharides simultaneously react with the at least one hydrazide-activated protein resulting in a complex multivalent conjugate that includes at least one C=N double bond formed between each attached immunogenic-distinct polysaccharide and the protein; and reducing substantially all of the C=N double bonds of the complex multivalent conjugate to C—N bonds resulting in a complex multivalent immunogenic conjugate product.

In a further embodiment, there is described a method for making a complex multivalent immunogenic conjugate, comprising:

reacting a plurality of immunogenic-distinct polysaccharides with a cyanylation agent resulting in a mixture of a plurality of cyanate-activated immunogenic-distinct polysaccharides;

reacting at least one protein with hydrazine, carbohydrazide, hydrazine dichloride, a dihydrazide, or a mixture thereof under conditions sufficient to produce a solution of at least one hydrazide-activated protein; and contacting the mixture of the plurality of cyanate-activated immunogenic-distinct polysaccharides with the at least one hydrazide-activated protein at a pH of about 6 to about 8 such that the plurality of cyanate-activated immunogenic-distinct polysaccharides simultaneously react with the at least one hydrazide-activated protein resulting in a complex multivalent immunogenic conjugate that includes at least one C—N bond formed between each attached immunogenic-distinct polysaccharide and the protein.

In another embodiment, there is described a method for making a complex multivalent immunogenic conjugate, comprising:

reacting a protein with 1-amino-2,3-propanediol (ADPO) in the presence of 1-[3-(dimethylamino)propyl]-3-ethyl carbodiimide hydrochloride at a pH of from about 6 to about 7 resulting in a solution of an ADPO-modified protein;

reacting the ADPO-modified protein with an oxidizing agent resulting in a solution of an aldehyde-activated protein;

contacting a mixture of the plurality of hydrazide-activated immunogenic-distinct polysaccharides with the aldehyde-activated protein at a pH of about 5 to about 8 such that the plurality of hydrazide-activated immunogenic-distinct polysaccharides simultaneously react with at least one aldehyde-activated protein resulting in a complex multivalent conjugate that includes at least one C=N double bond formed between each attached immunogenic-distinct polysaccharide and the protein; and reducing substantially all of the C=N double bonds of the complex multivalent conjugate to C—N bonds resulting in a complex multivalent immunogenic conjugate product.

Also disclosed herein are methods for preparing a hydrazide-activated protein, comprising:

reacting a protein with hydrazine, carbohydrazide, hydrazine chloride, a dihydrazide, or a mixture thereof in the presence of (i) a carbodiimide and (ii) at least one amino acid, at least one peptide, or a mixture of at least one amino acid and at least one peptide.

A further embodiment disclosed herein for making a complex multivalent immunogenic conjugate includes:

(a) contacting at least one first aldehyde-activated immunogenic-distinct polysaccharide with at least one hydrazide-activated protein under conditions sufficient for forming a first conjugate intermediate such that at least one C=N double bond forms between the first immunogenic-distinct polysaccharide and the protein;

(b) contacting at least one second aldehyde-activated immunogenic-distinct polysaccharide with the first conjugate intermediate such that at least one C=N double bond forms between the second immunogenic-distinct polysaccharide and the protein; and (c) reducing substantially all of the C=N double bonds to C—N bonds resulting in a complex multivalent immunogenic conjugate product (the reduction is preferably a single step so that all of the C=N double bonds are reduced substantially simultaneously);

wherein the reactivity of the first aldehyde-activated immunogenic-distinct polysaccharide with the hydrazide-activated protein is lower than the reactivity of the second aldehyde-activated immunogenic-distinct polysaccharide with the hydrazide-activated protein.

The foregoing and other objects, features, and advantages will become more apparent from the following detailed description, which proceeds with reference to the accompanying figures.

BRIEF DESCRIPTION OF THE DRAWINGS

FIG. 15 ELISA detection of conjugated component polysaccharide in the combined synthesized multi-valent conjugate vaccine of lot TTH2C/A/WY070209. A 25 uL conjugate sample containing 0.05 mg/mL protein (tetanus toxoid) and 0.0125 mg/mL each of Mn A, C, W135 and Y PS was analyzed by HPLC. Only protein-containing species (i.e. conjugates and free TTH) of the HPLC fractions adhered to the ELISA plate during coating, and the conjugated polysaccharides were subsequently detected by antisera specific to each respective PS but not cross-reacting to tetanus toxoid (solid symbols). A sample of native polysaccharide mixture was also analyzed in parallel (open symbols). Significant incorporation of all four PS into the conjugate is indicated by their respective ELISA signals as compared to their native PS. The weaker reactivity of activated Mn C PS in conjugating to TTH shown in FIG. 14 was compensated with a higher dose (double in this case) and earlier exposure to TTH prior to reaction with activated Mn A, W135 and Y PS.

DETAILED DESCRIPTION

Figure 1:
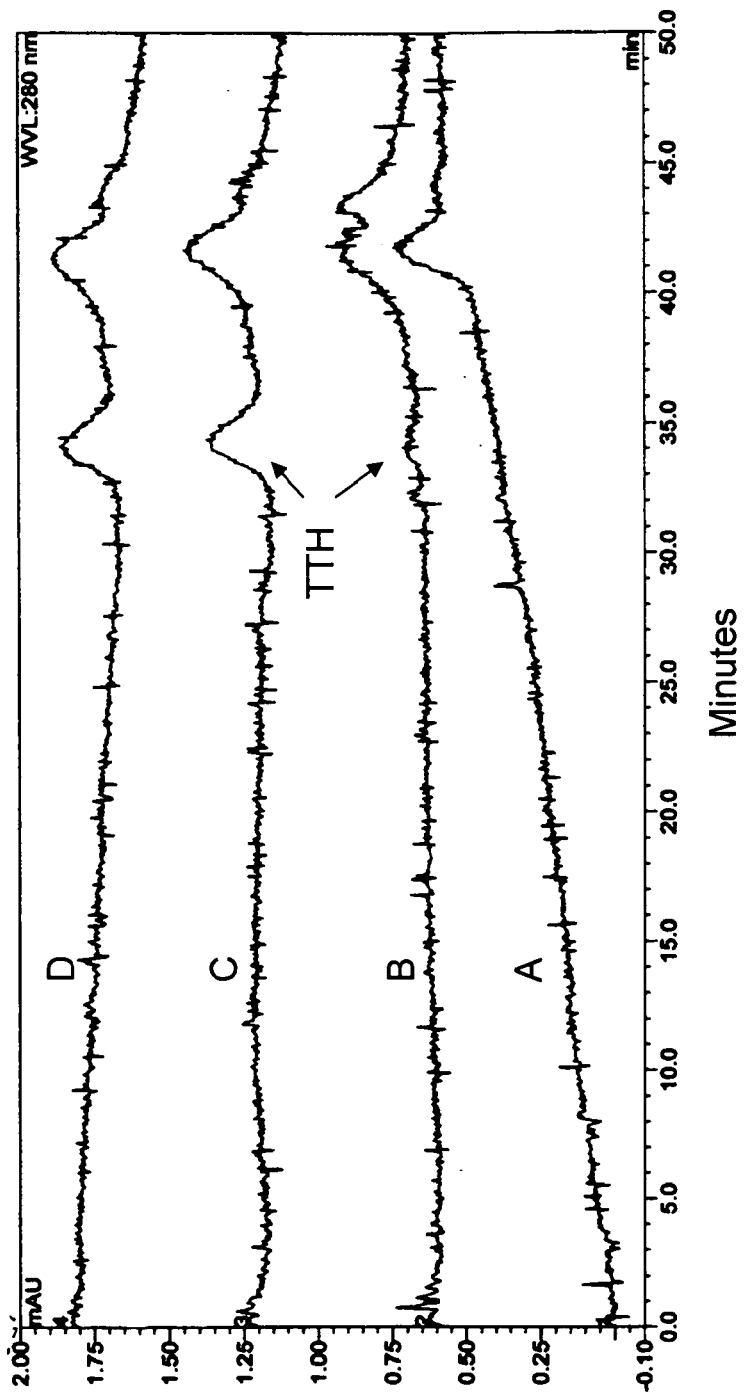
FIG. 1 HPLC profiles (280 nm, by a Superose 6 column) of tetanus toxoid activation product (TTH) with hydrazine or adipic acid dihydrazide (ADH) catalyzed by various EDC concentrations and reaction times. The reaction conditions are: (A) hydrazine, 24 mM EDC for 4 hours; (B) hydrazine, 12 mM EDC, overnight; (C) ADH, 36 mM EDC for 4 hours; (D) ADH, 48 mM EDC for 2 hours. The product has too high molecular weight to pass through the column and shows no TTH signal in profile (A). In profile (B), only small fraction of the product passes through the column and shows a shadow peak for TTH at 34 minute. In profiles (C) and (D), the product passes through the column and shows a peak for TTH at 34 minute.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. In addition, the materials, methods, and examples are illustrative only and not intended to be limiting. The methods and processes described herein are not limited to performance in any specific sequence or steps, unless otherwise noted. For example, activation of the polysaccharides can occur before, or after, or parallel to activation of the proteins.

In order to facilitate review of the various examples of this disclosure, the following explanations of specific terms are provided:

"Animal" includes living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, rodents, horses, and cows.

An "antigen" is a compound, composition, or substance that may be specifically bound by the products of specific humoral or cellular immunity, such as an antibody molecule or T-cell receptor. Antigens can be any type of biologic molecule including, for example, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

A "carrier" is an immunogenic molecule to which a hapten or an antigen such as a polysaccharide, can be bound. When bound to a carrier, the bound molecule may become more immunogenic. Carriers are chosen to increase the immunogenicity of the bound molecule and/or to elicit antibodies against the carrier which are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, proteins from bacteria or viruses), semi-synthetic or synthetic materials containing one or more functional groups to which a reactant moiety can be attached.

Examples of bacterial products for use as carriers include bacterial toxins, such as *B. anthracia* PA (including fragments that contain at least one antigenic epitope and analogs or derivatives capable of eliciting an immune response), LF and LeTx, and other bacterial toxins and toxoids, such as tetanus toxin/toxoid, diphtheria toxin/toxoid, *P. aeruginosa* exotoxin/toxoid, pertussis toxin/toxoid, and *C. perfringens* exotoxin/toxoid. Viral proteins, such as hepatitis B surface antigen and core antigen can also be used as carriers.

A "covalent bond" is an interatomic bond between two atoms, characterized by the sharing of one or more pairs of electrons by the atoms. The terms "covalently bound" or "covalently linked" refer to making two separate molecules into one contiguous molecule.

An "epitope" is an antigenic determinant. These are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

"Linked," "joined," conjugated," or "attached" refer to covalent bond linkage of a polysaccharide to a carrier protein. The covalent bond linkage can be direct or indirect, e.g., linked though a spacer molecule.

A "complex multivalent immunogenic conjugate" or "complex multivalent conjugate vaccine" comprises more than one antigenic epitope. In a first embodiment, complex multivalent immunogenic conjugates disclosed herein include mixtures of different molecules, each molecule comprising different immunogenic-distinct polysaccharides wherein each different immunogenic-distinct polysaccharide is conjugated to a separate protein carrier. In a second embodiment, complex multivalent immunogenic conjugates disclosed herein include molecules in which a plurality of immunogenic-distinct polysaccharides are conjugated to a single protein molecule or single protein construct (which protein construct itself includes more than one different protein). A third embodiment includes a mixture of the conjugates of the first embodiment and the conjugates of the second embodiment. An example of the first embodiment may be depicted as a mixture of the different structures represented by:

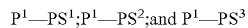

wherein $P^1$ is a carrier protein; and $PS^1$, $PS^2$, and $PS^3$ are each immunogenic-distinct polysaccharides.

An example of the second embodiment may be depicted as a structure represented by:

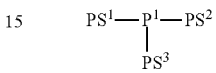

wherein $P^1$ is a carrier protein; $PS^1$, $PS^2$, and $PS^3$ are each immunogenic-distinct polysaccharides that are covalently attached to $P^1$.

The protein and polysaccharide in the above formulae can be singular or plural structural units, and there is at least one bond formed between the protein and the polysaccharide.

An "immune response" is a response of a cell of the immune system, such as a B-cell, T-cell, macrophage or polymorphonucleocyte, to a stimulus. An immune response can include any cell of the body involved in a host defense response for example, an epithelial cell that secretes interferon or a cytokine. An immune response includes, but is not limited to, an innate immune response or inflammation.

"Immunogenic conjugate or composition" is a term used herein to mean a composition useful for stimulating or eliciting a specific immune response (or immunogenic response) in a vertebrate. In some embodiments, the immunogenic response is protective or provides protective immunity, in that it enables the vertebrate animal to better resist infection or disease progression from the organism against which the immunogenic composition is directed. One specific example of a type of immunogenic composition is a vaccine.

An "immunogen" refers to a compound, composition, or substance which is capable, under appropriate conditions, of stimulating the production of antibodies or a T-cell response in an animal, including compositions that are injected or absorbed into an animal.

An "immunogenic-distinct polysaccharide" includes a polysaccharide that elicits an immune response that differs from the immune response elicited by another type of polysaccharide. Immunogenic-distinct polysaccharides may be two or more polysaccharides from different encapsulated bacteria. For example, a pneumococcal polysaccharide is an immunogenic-distinct polysaccharide compared to a meningococcal polysaccharide. Immunogenic-distinct polysaccharides also are inclusive of two or more polysaccharides from different serogroups or serotypes. For example, a meningococcal polysaccharide of serogroup A is an immunogenic-distinct polysaccharide compared to a meningococcal polysaccharide of serogroup B.

"Inhibiting or treating a disease" includes inhibiting the full development of a disease or condition, for example, in a subject who is at risk for a disease such as anthrax. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

A "peptide" includes a molecule in which the structural units are at least two amino acid residues which are joined together through amide bonds. A peptide includes a dipeptide, a tripeptide or an oligopeptide. The term "residue" or "amino acid residue" includes reference to an amino acid that is incorporated into a peptide.

A "therapeutically effective amount" refers to a quantity of a specified agent sufficient to achieve a desired effect in a subject being treated with that agent. For example, this may be the amount of a multivalent polysaccharide conjugate useful in increasing resistance to, preventing, ameliorating, and/or treating infection and disease caused by a bacterial infection in a subject. Ideally, a therapeutically effective amount of an agent is an amount sufficient to increase resistance to, prevent, ameliorate, and/or treat infection and disease caused by infection in a subject without causing a substantial cytotoxic effect in the subject. The effective amount of an agent useful for increasing resistance to, preventing, ameliorating, and/or treating infection and disease caused by infection in a subject will be dependent on the subject being treated, the severity of the affliction, and the manner of administration of the therapeutic composition.

A vaccine is a pharmaceutical composition that elicits a prophylactic or therapeutic immune response in a subject. In some cases, the immune response is a protective response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a polysaccharide, a virus, a bacterium, a cell or one or more cellular constituents. In some cases, the virus, bacterium or cell may be inactivated or attenuated to prevent or reduce the likelihood of infection, while maintaining the immunogenicity of the vaccine constituent.

Disclosed are novel methods for preparing complex multivalent immunogenic conjugates and conjugate vaccines. In one embodiment, the multivalent conjugates and conjugate vaccines are synthesized by conjugating mixtures of more than one polysaccharide at a desired ratio of the component polysaccharides to at least one carrier protein using the method of hydrazide chemistry. Because of the high efficiency of hydrazide chemistry in conjugation, the polysaccharides are effectively conjugated to carrier protein(s) so that the resulting complex synthesized vaccine conjugate products, without requiring tedious and complicated purification procedures such as chromatography and/or ammonium sulfate precipitation, are efficacious in inducing antibody in mice against each component polysaccharide. The methods of certain embodiments disclosed herein simplify the preparation of multivalent conjugate vaccines by utilizing simultaneous conjugation reactions in a single reaction mixture or batch that includes at least two immunogenic-distinct polysaccharides. This single-batch simultaneous reaction eliminates the need for multiple parallel synthesis processes for each polysaccharide vaccine conjugate component as employed in conventional methods for making multivalent conjugate vaccines. In other words, according to conventional methods each individual polysaccharide conjugate component is prepared by a separate process, and then the resulting individual polysaccharide conjugate components are mixed together into a single dosage formulation (see, e.g., US 2005/0002948 A1, paragraph [0033]). Synthesizing multivalent conjugates and vaccines according to the presently disclosed inventive methods will significantly reduce the costs of production and facilitate field application of vaccination, thus greatly promoting the public health.

In the presently disclosed methods, high efficiency chemistry is applied to the combined synthesis of multivalent conjugate vaccines as such that all the activated component polysaccharides are able to form a conjugate with the activated protein as detected by HPLC in conjunction with ELISA using respective PS-specific antibodies for detection.

In certain embodiments, less reactive polysaccharide(s) are initially reacted with the activated protein. The more reactive polysaccharide(s) are then subsequently reacted with the less reactive PS/protein intermediate conjugate. The less reactive polysaccharides are reacted first to provide a longer reaction time without competition from the more reactive polysaccharides so that a greater amount of the less reactive polysaccharides are conjugated.

The relative reactivity of an activated polysaccharide with an activated protein refers to the reaction rate and/or amount of conjugated polysaccharide. A higher reaction rate and/or a greater amount of achieved conjugation are indicative of a more reactive polysaccharide. The reactivity of an activated polysaccharide depends on at least several factors: the degree of activation (the more attached functional groups, the higher the reactivity); chain length (at the same degree of activation, a longer chain containing more functional groups has a higher reactivity); and polysaccharide structure (steric hindrance, structural stability, etc.).

In the specific instance of reductive amination conjugation, the degree of activation of the polysaccharide is controlled by the activation agent (e.g., $NaIO_4$), temperature, reaction time, and the polysaccharide structure. The activation agent breaks the chain of Mn C polysaccharide, but not Mn A, Mn W 135, and Mn Y polysaccharides. In the specific instance of cyanylation conjugation, the degree of activation of the polysaccharide is controlled by the activation agent, pH, reaction time, and the hydroxyl group density of the polysaccharide. Mn A and Mn C polysaccharides have a lower hydroxyl density relative to Mn W135 and Mn Y polysaccharides. It has been found that, in general, the reactivity of activated Mn C and Mn A polysaccharides is lower relative to the reactivity of Mn W135 and Mn Y polysaccharides.

As described above, also disclosed herein is a novel method for activating a carrier protein that includes reacting a protein with hydrazine, carbohydrazide, hydrazine dihydrochloride, a dihydrazide (e.g., succinyl dihydrazide or adipic acid dihydrazide), or a mixture thereof in the presence of (i) 1-[3-(dimethylamino)propyl]-3-ethyl carbodiimide hydrochloride and (ii) at least one amino acid, at least one peptide, or a mixture of at least one amino acid and at least one peptide. The novel protein activation method can be used to conjugate to polysaccharides for monovalent conjugate vaccines or to mixtures of polysaccharides for multivalent (or complex multivalent) conjugate vaccines as described below. Useful amino acids include protein amino acids in alpha-L-form (or isomer, normally called L-amino acids). Other amino acids include alpha-D-form (D-amino acids), beta-form (beta amino acid), gamma-form, delta-form and epsilon-form, etc. Illustrative amino acids include lysine, arginine, histidine, glycine, serine, threonine, glutamic acid, cysteine, and mixtures thereof. The broad, preferred, and more preferred concentration ranges for the amino acids present in the activation composition are 1-500 mM, 20-300 mM and 36-144 mM, respectively.

Although not bound by any theory, it is believed that the amino acids can also get incorporated to the protein molecule like hydrazine during the activation reaction. The incorporated amino acid residues can possibly perturb the protein hydration environment and also provide steric hindrance, leading to prevention of protein aggregation and precipitation.

In one example, this method includes introducing at least one hydrazide group onto the carrier protein by reacting the protein with excess hydrazine, carbohydrazide, succinyl dihydrazide or ADH catalyzed by a carbodiimide under controlled conditions including: 1) the reaction time, 2) the concentration of EDC, and 3) the concentration of amino acid or amino acid mixture in the reaction. The resulting hydrazide-activated carrier protein can be maintained soluble at neutral pH for an extended period of time (e.g., for at least about one year).

Conventional methods for synthesis and manufacturing of polysaccharide-protein conjugate vaccines typically employ conjugation reactions with low efficiency (typically about 20%). This means that up to 80% of the added activated polysaccharide is lost. In addition, a chromatographic process for purification of the conjugates from unconjugated PS is typically required. The synthetic methods of the preferred embodiments utilize the characteristic chemical property of hydrazide groups on one reactant to react with aldehyde groups or cyanate esters on the other reactant with an improved conjugate yield (typically as high as about 60%).

When the conjugation reaction proceeds with greater conjugation efficiency, the amount of unconjugated protein and polysaccharide remaining after reaction can be sufficiently low so as to make its removal unnecessary. Accordingly, the process of purifying the conjugate product can be simplified to, e.g., a diafiltration step for removal of small molecule by-products. The hydrazide-based conjugation reaction can be carried to completion within one to three days at reactant concentrations of from about 1 to about 50, particularly about 1 to about 40, mg/mL, or about 1 to about 50 mg/mL, at PS/protein weight ratios of from about 1:5 to about 5:1, preferably from about 1:2 to about 2:1, and most preferably about 1:1, although in certain embodiments higher or lower ratios can be preferred. The conjugation reaction is preferably conducted at temperatures of from about 4° C. to about 40° C., preferably from about 4, 10, 15, or 20° C. to about 25, 30, or 35° C., and at a pH of from about 6 to about 8.5, preferably from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, or 8.4, with optimal conditions varying according to the polysaccharide. Accordingly, conjugate vaccine can be manufactured at lower cost when a hydrazide-based conjugation reaction is employed.

To overcome certain drawbacks of conventional methods for synthesizing conjugate vaccines, a method for conjugation of PSs to carrier proteins using hydrazide chemistry in reductive amination and cyanylation conjugation reactions is provided. Hydrazide groups having the structure —NH—NH$_2$ are introduced onto the carboxyl groups of the aspartic acid and/or glutamic acid residues of protein molecules by carbodiimide reaction with hydrazine, ADH, carbohydrazide, or succinyl dihydride. In one embodiment, the activated protein is maintained soluble at a pH of from about 10 to about 11.5, preferably from about 10.1, 10.2, 10.3, or 10.4 to about 10.6, 10.7, 10.8, 10.9, 11.0, 11.1, 11.2, 11.3, or 11.4, and most preferably about 10.5, with a buffer at a concentration of from about 3 or less to about 10 mM or more, preferably from about 4 or 5 mM to about 6, 7, 8, or 9; mM, before conjugation. Suitable buffers include but are not limited to Na$_2$CO$_3$, 3 (cyclohexylamino)-1-propanesulfonicacid (CAPS), and (2-(N-cyclohexylamino)ethane sulfonic acid (CHES). In another embodiment, the activated protein is maintained soluble at neutral or approximately neutral pH (e.g., pH of about 7 to about 7.5) by activating the protein in the presence of at least one amino acid as described above, and exemplified in more detail below.

The activated protein is then reacted with activated polysaccharide containing either aldehyde (reductive amination) or cyanate (cyanylation conjugation) groups at a pH of from about 6 to about 8.5, preferably from about 6.1, 6.2, 6.3, 6.4, or 6.5 to about 6.6, 6.7, 6.8, 6.9, 7.0, 7.1, 7.2, 7.3, 7.4, 7.5, 7.6, 7.7, 7.8, 7.9, 8.0 in the presence of a buffer at a concentration about 100 mM or less to about 200 mM, preferably from about 110, 120, 130, 140 or 150 mM to about 160, 170, 180 or 190 mM. Suitable buffers include but are not limited to N-(2-hydroxyethyl)piperazine-N'-(2-ethanesulfonic acid) (HEPES), phosphate buffered saline (PBS), 2 morpholino-propanesulfonic acid (MOPS), and N,N-bis(2-hydroxy-ethyl)-2-aminoethanesulfonic acid (BES).

Alternatively, the PS can be functionalized with hydrazide groups. The activated PS can be conjugated, at pH 6.5-7.5 with a strong buffer, to activated proteins containing aldehyde groups (reductive amination). The protein is maintained soluble at a pH of about 10.5 with a weak buffer until the point of conjugation. Because of the higher reactivity of hydrazide groups (pKa-2.6) compared to the lysine epsilon-amino group (pKa=10.5) at neutral/mild acidic conditions, and the enhanced solubility of the conjugate using activated protein maintained soluble at about pH 10.5 before conjugation, the yield of the conjugation reaction is greatly increased.

Conjugates prepared by these methods are immunogenic in experimental animals, as demonstrated in experiments on mice. In addition, the conjugation reaction can be efficiently carried out without sodium cyanoborohydride, thereby avoiding introduction of cyanide ion in the conjugate product. The reaction can be conducted under mild acidic or neutral pH conditions at 4° C. for 1-3 days or at room temperature overnight as opposed to days for conventional reductive amination conjugation methods. This again ensures high yield conjugate vaccine production for unstable polysaccharides, such as those from *Haemophilus influenzae* type b, *Streptococcus pneumonias* type 19F and *Neisseria meningitides* group A. The methods of preferred embodiments can be employed to produce less expensive complex multivalent conjugate vaccines, thereby greatly promoting public health.

The Polysaccharide

The term "polysaccharide" as used herein, is a broad term and is used in its ordinary sense, including, without limitation, saccharides comprising a plurality of repeating units, including, but not limited to polysaccharides having 50 or more repeat units, and oligosaccharides having 50 or less repeating units. Typically, polysaccharides have from about 50, 55, 60, 65, 70, 75, 80, 85, 90, or 95 repeating units to about 2,000 or more repeating units, and preferably from about 100, 150, 200, 250, 300, 350, 400, 500, 600, 700, 800, 900 or 1000 repeating units to about, 1100, 1200, 1300, 1400, 1500, 1600, 1700, 1800, or 1900 repeating units. Oligosaccharides typically about from about 6, 7, 8, 9, or 10 repeating units to about 15, 20, 25, 30, or 35 to about 40 or 45 repeating units.

Suitable polysaccharides for use in the preferred embodiments include polysaccharides and oligosaccharides from encapsulated bacteria. The polysaccharides and oligosaccharides can be from any source, for example, they can be derived from naturally-occurring bacteria, genetically engineered bacteria, or can be produced synthetically. The polysaccharides and oligosaccharides can be subjected to one or more processing steps prior to activation, for example, purification, functionalization, depolymerization using mild oxidative conditions, deacetylation, and the like. Post processing steps can also be employed, if desired. Any suitable method known in the art for synthesizing, preparing, and/or purifying suitable polysaccharides and oligosaccharides can be employed.

Polysaccharides and oligosaccharides for use in preferred embodiments include pneumococcal polysaccharides of, for example, serogroups 1, 2, 3, 4, 5, 6B, 7F, 8, '9N, 9V, 10A, 11A, 12F, 14, 15B, 17F, 18C, 19A, 19F, 20, 22F, 23F and 33F; meningococcal polysaccharides of serotypes A, B, C, W135, and Y, *Haemophilus influenzae* type b polysaccharide polyribosylribitol phosphate, group B streptococcal polysaccharides of serotypes III and V and *Salmonella typhi* Vi polysaccharide. Other polysaccharides of pneumococcal and group B streptococcal serotypes, and meningococcal serogroups are also suitable for use herein, as are other T-independent polysaccharide and oligosaccharide antigens, for example, polysaccharides or oligosaccharides derived from group A *streptococcus, Staphylococci, Enterococci, Klebsiella pneumoniae, E. coli, Pseudomonas aeruginosa*, and *Bacillus anthracis*. While bacterial polysaccharides and oligosaccharides are particularly preferred, gram (−) bacterial lipopolysaccharides and lipooligosaccharides and their polysaccharide and oligosaccharide derivatives, and viral polysaccharides and oligosaccharides can also be employed.

Polysaccharides with side chain phosphorus and/or backbone phosphorus are suitable for use in preferred embodiments. The conjugation reactions of preferred embodiments are particularly well suited for use with polysaccharides having phosphorus in the backbone. Such polysaccharides are sensitive to fragmentation and degradation, so the low temperature (4° C.) reaction condition and rapidity of the conjugation reaction results in a higher quality conjugate due to the reduced degradation of polysaccharide.

After completion of any pre-processing steps, the polysaccharide or oligosaccharide is subjected to an "activation" step. The term "activation" refers to a chemical treatment of the polysaccharide to provide chemical groups capable of reacting with the protein. In a particularly preferred embodiment, activation involves functionalization of the polysaccharide or oligosaccharide with aldehyde groups, ketone groups or cyanate groups that are reacted with hydrazide groups on a functionalized protein. Alternatively, the polysaccharide or oligosaccharide can be functionalized with hydrazide groups that are reacted with aldehyde groups or ketone groups on a functionalized protein.

According to one embodiment, a mixture of more than one polysaccharide can be simultaneously activated by reaction with a single activating agent (or a mixture of activating agents) in single batch step. For example, a mixture of Mn A, Mn C, Mn W135 and Mn Y polysaccharides can be reacted with an aldehyde-functionalizing agent in a single batch reaction. According to another embodiment, each individual polysaccharide can be activated by reaction with an activating agent in a separate process. The separately activated polysaccharides can then be mixed together prior to the conjugation step so the activated polysaccharides can be simultaneously conjugated in a single process.

Any suitable functionalization reaction can be employed to activate the polysaccharide or oligosaccharide with cyanate groups. Preferably, the polysaccharide or oligosaccharide is reacted with 1-cyano-4-dimethylammoniumpyridinium tetrafluoroborate in the presence of triethylamine.

Any suitable functionalization reaction can be employed to activate the polysaccharide or oligosaccharide with aldehyde groups. Certain polysaccharides and oligosaccharides possess terminal aldehyde groups that can participate in the conjugation reaction. If the polysaccharide or oligosaccharide is activated with aldehyde groups, a preferred reaction involves reaction with an oxidizing agent, such as $NaIO_4$. Oxidizing agents have the potential for fragmenting the polysaccharide or oligosaccharide. Undesirable fragmentation can be avoided or controlled through selection of the particular oxidizing agent and the concentration of the oxidizing agent employed. Ketone groups are also capable of reacting with hydrazide, so activation of the polysaccharide or oligosaccharide with ketone groups can be employed in certain embodiments.

Any suitable functionalization reaction can be employed to activate the polysaccharide or oligosaccharide with hydrazide groups. A preferred functionalization reaction is reductive amination, wherein the polysaccharide or oligosaccharide is reacted with $NaIO_4$ in a periodate activation reaction to yield aldehyde groups, which are then reacted with hydrazine and adipic acid dihydrazide, followed by subsequent reduction with $NaBH_4$. Alternatively, a cyanylation conjugation reaction can be employed, wherein polysaccharide or oligosaccharide is reacted with cyanogen bromide or 1-cyano-4-dimethylammoniumpyridinium tetrafluoroborate to introduce a cyanate group which is subsequently reacted with hydrazine and adipic acid dihydrazide. A carbodiimide reaction can also be employed, wherein polysaccharide or oligosaccharide is reacted with adipic acid dihydrazide in the presence of 1-[3-(dimethylamino)propyl]-3-ethyl carbodiimide hydrochloride).

A strongly buffered (at pH of from about 6.5 to about 8, with a high buffer concentration of from about 100 mM to about 200 mM) activated polysaccharide solution is preferably employed in the conjugation reaction in the form of a strongly buffered solution. Any suitable buffer can be employed, preferably a buffer such as N-(2-Hydroxyethyl) piperazine-N'-(2-ethanesulfonic acid) or phosphate buffered saline.

The Protein

The activated polysaccharide or oligosaccharide is coupled to a protein to yield a conjugate vaccine. Suitable proteins include bacterial toxins that are immunologically effective carriers that have been rendered safe by chemical or genetic means for administration to a subject. Examples include inactivated bacterial toxins such as diphtheria toxoid, $CRM_{197}$, tetanus toxoid, pertussis toxoid, *E. coli* LT, *E. coli* ST, and exotoxin A from *Pseudomonas aeruginosa*. Bacterial outer membrane proteins such as, outer membrane complex c (OMPC), porins, transferrin binding proteins, pneumolysis, pneumococcal surface protein A (PspA), pneumococcal adhesin protein (PsaA), or pneumococcal surface proteins BVH-3 and BVH-11 can also be used. Other proteins, such as protective antigen (PA) of *Bacillus anthracis* and detoxified edema factor (EF) and lethal factor (LF) of *Bacillus anthracis*, ovalbumin, keyhole limpet hemocyanin (KLH), human serum albumin, bovine serum albumin (BSA) and purified protein derivative of tuberculin (PPD) can also be used. The proteins are preferably proteins that are non-toxic and non-reactogenic and obtainable in sufficient amount and purity that are amenable to the conjugation methods of preferred embodiments. For example, diphtheria toxin can be purified from cultures of *Corynebacterium diphtheriae* and chemically detoxified using formaldehyde to yield a suitable protein.

Fragments of the native toxins or toxoids, which contain at least one T-cell epitope, are also useful, as are outer membrane protein complexes, as well as certain analogs, fragments, and/or analog fragments of the various proteins listed above. The proteins can be obtained from natural sources, can be produced by recombinant technology, or by synthetic methods as are known in the art. Analogs can be obtained by various means, for example, certain amino acids can be substituted for other amino acids in a protein without appreciable loss of interactive binding capacity with structures such as, for example, antigen-binding regions of antibodies or binding sites on substrate molecules. Other proteins can also be employed, such as those containing surface exposed glutamic acid or aspartic acid groups.

Any suitable functionalization reaction can be employed to activate the protein with hydrazide groups. Conventional methods for preparing hydrazide-modified proteins include EDC catalysis and a two-step process using N-succinimidyl iodoacetate and thiol hydrazide through lysine s-amino groups of the protein. See King et al., Biochemistry 1986; 25:5774-5779. Modified protein prepared by EDC catalysis typically needs to be fractionated in order for it to be suitable for use in conjugation, and the two-step process is tedious. Accordingly, it is generally not preferred to employ such methods for preparing the hydrazide-modified protein. However, in certain embodiments such methods can be acceptable or even desirable.

Preferably, hydrazide groups are introduced into proteins through the carboxyl groups of aspartic acid and glutamic acid residues on the protein using a carbodiimide reaction, for example, by reaction with hydrazine, carbohydrazide, succinyl dihydrazide, adipic acid dihydrazide, hydrazine chloride (e.g., hydrazine dihydrochloride) or any other dihydrazides in the presence of EDC. EDC is employed as a catalyst to activate and modify the protein reactant with hydrazine or the dihydrazide. Any water-soluble carbodiimide including EDC can be used as a catalyst. EDC-catalyzed proteins generally have a tendency to polymerize and precipitate. See Schneerson et al., Infect. Immun. 1986, 52:519-528; Shafer et al., Vaccine 2000; 18(13): 1273-1281; and Inman et al., Biochemistry 1969; 8:4074-4082. Aggregation and precipitation of the activated protein depends, in part, on its pH environment. Accordingly, the tendency to polymerize and precipitate can be controlled by maintaining such hydrazide-modified proteins soluble in a buffered solution. By buffer-exchanging the reaction mixture so as to maintain the activated protein at a pH of about 10.5, the activated protein remains soluble and stable for conjugation. Any suitable buffer can be employed. Preferably a weak buffer such as $Na_2CO_3$ at a low concentration of from about 3 mM to about 10 mM is employed.

The buffered hydrazide-modified protein can then be employed in preparing protein-polysaccharide conjugates without precipitation when added to activated polysaccharide at a pH of from about 6 to 8.5, preferably from about 6.5 to about 8. Any suitable functionalization reaction can be employed to activate the protein with aldehyde groups. Preferably, the protein is reacted with 1-amino-2,3-propanediol in the presence of EDC followed by oxidation with $NaIO_4$. Amino sugars such as glucosamine, galactosamine, and the like can be used in place of 1-amino-2,3-propanediol. In this reaction, EDC is also employed as a catalyst to activate and modify the protein reactant with the aminodiol through the carboxyl groups of aspartic acid and glutamic acid residues of the protein.

The protein may also be activated in the presence of an amino acid or amino acid mixtures as described above, and maintained soluble at neutral pH of about 7 to about 7.5.

Preparation of Conjugates by Reductive Amination

Conjugates can be prepared via the reaction of aldehyde and hydrazide groups (reductive amination). The reductive amination conjugation reaction can be employed to conjugate a hydrazide-modified reactant (protein or polysaccharide) to the other component containing aldehyde groups.

In conventional reductive amination, the reaction between aldehyde and amino groups is reversible and unfavorable, such that sodium cyanoborohydride is needed to facilitate the conjugation by converting the C=N double bond to a C—N single bond to render the entire reductive amination event irreversible. In contrast, the reductive amination conjugation reaction of preferred embodiments proceeds without the aid of sodium cyanoborohydride because of the high efficiency of the hydrazide-aldehyde reaction. At the end of the reductive amination conjugation reaction, sodium borohydride or another suitable reductant is employed to reduce the C=N double bond to a C—N single bond, as well as to reduce any residual aldehyde groups to alcohol groups. The reductive amination conjugation reaction of preferred embodiments avoids contamination of the resulting conjugate with cyanide, a by-product of sodium cyanoborohydride.

To reduce precipitation of activated protein during the conjugation reaction, the activated protein is preferably in the form of a weakly buffered solution with a low buffer concentration of from about 3 mM to about 10 mM which is added to a strongly buffered (at pH of from about 6.5 to about 7.5, with a high buffer concentration of from about 100 mM to about 200 mM) activated polysaccharide solution. Preferably, the pH of the activated protein solution is buffered to from about 10 pH to about 11.5 pH, most preferably to about 10.5 pH. The activated polysaccharide solution is preferably strongly buffered to from about 6 pH to about 8 pH, most preferably to from about 6.5 pH to about 7.5 pH. The hydrazide-aldehyde reductive amination reaction proceeds at a fast rate, and the precipitating effect of a pH lower than 10.5 (for example, a pH as low as from about 8.5 to about 9.5) on activated protein is overcome by the molecular properties of the reacting activated polysaccharide.

Preparation of Conjugates by Cyanylation Conjugation

Conjugates can be prepared via the reaction of hydrazide and cyanate groups (cyanylation conjugation). The cyanylation conjugation reaction is efficient and reversible, favoring the product formation. In certain embodiments, blocking agents are employed to remove residual cyanate groups. However, addition of a blocking agent to the reaction mixture drives the conjugation reaction backward and reduces the conjugation yield by 5-12%. The effect of various blocking agents on yield was investigated. The pneumococcal polysaccharide Pn 18C PS was activated with CDAP and then conjugated to hydrazide activated tetanus toxoid (TTH) overnight. Five aliquots were added with either water or a blocking agent to 0.2 M. After 4 hours incubation, the samples were analyzed by HPSEC using a Waters Ultrahydrogel 2000 column with a 280 nm monitor. The conjugation yield of each sample, provided in Table C, was determined as the % area of the conjugate peak at 1 5.5 minutes over total protein, i.e. conjugate peak plus the free TTH peak (at 22 minutes). While in certain embodiments it can be desirable to employ blocking agents to quench the leftover residual cyanate groups, it is generally preferred to avoid their use so as to avoid reduction in conjugate yield.

TABLE C

| Blocking agent (0.2M) | Conjugation yield | % Control | % Reduction |
|---|---|---|---|
| None (control) | 75 | 100 | 0 |
| ADH | 63 | 84 | 16 |
| Hydrazine | 70 | 93 | 7 |
| Glycine | 66 | 89 | 11 |
| Ethanolamine | 65 | 87 | 13 |

To remove residual cyanate groups in the conjugation product without using a blocking agent, the conjugation time can be prolonged. Preferably, conjugation is conducted at a temperature of from about 0° C. to about 5° C. for about 36 to about 48 hours, most preferably at about 4° C. for about 36 hours, followed by about an additional 18 to 24 hours at a temperature of from about 20° C. to about 25° C., most preferably at about 18 hours at about 20 to 24° C., such that the residual cyanate groups react with water and decompose. Longer or shorter conjugation times and/or higher or lower conjugation temperatures can be employed, and different sequences of steps at various times and temperatures can be conducted, as desired. It is desirable, however, to conduct the conjugation reaction, at least initially, at low temperatures, preferably from about 0° C. to about 5° C., more preferably at about 4° C., so as to reduce the degree of precipitation of the conjugate.

With high conjugation yields and high immunogenicity of the conjugation product, purification processes such as column chromatography and/or ammonium sulfate precipitation of the conjugate from unconjugated polysaccharide may not be necessary. However, in certain embodiments it can be desirable to conduct one or more purification steps.

The Conjugates

Both reactants contain multiple reactive groups per molecule. An activated polysaccharide molecule can react with and form more than one linkage to more than one activated protein molecule. Likewise, an activated protein molecule can react with and form more than one linkage to more than one activated polysaccharide molecule.

Therefore, the conjugate product is a mixture of various crosslinked matrix-type lattice structures. For example, a single linkage can be present, or 2, 3, 4, 5, 6, 7, 8, 9, 10, 11, 12, 13, 14, 15, 16, 17, 18, 19, 20, 21, 22, 23, 24, 25, 26, 27, 28, 29, 30 or more linkages can be present. The average number of linkages between a polysaccharide and a protein can be adjusted, as preferred. The preferred average number of linkages can depend upon the type of polysaccharide, the type of protein, the conjugation method, the reaction conditions, and the like. Generally, an average of 1 linkage to about 2, 3, 4, or 5 linkages is present, so as to avoid interfering with the ability of the protein to stimulate the immune system by over-conjugation, and so as to not cause changes in the polysaccharide structure. However, in certain embodiments more than 5 linkages can be tolerated or even desirable.

As described above, complex multivalent conjugates are produced by the methods disclosed herein. The number of immunogenic-distinct polysaccharides included in a complex multivalent conjugate is not limited, and may range from 2 to 28, preferably 5 to 25, and most preferably 15, in certain embodiments. The number of different carrier proteins included in a complex multivalent conjugate also is not limited, and may range from 1 to 10, preferably 4 to 6, and most preferably 5, in certain embodiments. For example, one carrier protein molecule may be conjugated to 2, 3, 4, 5, 6, etc., immunogenic-distinct polysaccharides. A construct conjugate may include a lattice structure that includes two or more different protein molecules conjugated each other and 2, 3, 4, 5, 6, etc., immunogenic-distinct polysaccharides.

After conjugation, the conjugate can be purified by any suitable method. Purification is employed to remove unreacted polysaccharide, protein, or small molecule reaction byproducts. Purification methods include ultrafiltration, size exclusion chromatography, density gradient centrifugation, hydrophobic interaction chromatography, ammonium sulfate fractionation, and the like, as are known in the art. As discussed above, the conjugation reactions of preferred embodiments proceed with higher yield, and generate fewer undesirable small molecule reaction byproducts. Accordingly, no purification may be necessary, or only a minor degree of purification such as diafiltration can be desirable. The conjugate can be concentrated or diluted, or processed into any suitable form for use in pharmaceutical compositions, as desired.

Methods of Treatment

Conjugates prepared according to the preferred embodiment are administered to a subject in an immunologically effective dose in a suitable form to prevent and/or treat infectious diseases. The term "subject" as used herein, refers to animals, such as mammals. For example, mammals contemplated include humans, primates, dogs, cats, sheep, cattle, goats, pigs, horses, mice, rats, rabbits, guinea pigs, and the like. The terms "subject", "patient", and "host" are used interchangeably. As used herein, an "immunologically effective" dose of the conjugate vaccine is a dose which is suitable to elicit an immune response. The particular dosage depends upon the age, weight and: medical condition of the subject to be treated, as well as on the method of administration. Suitable doses can be readily determined by those of skill in the art.

Pharmaceutical compositions comprising conjugate vaccines of preferred embodiments can offer various advantages over conventional vaccines, including enhanced immunogenicity of weakly immunogenic antigens, potential reduction in the amount of antigen used, less frequent booster immunizations, improved efficacy, preferential stimulation of immunity, or potential targeting of immune responses. The vaccines can be administered to a subject by a variety of routes, as discussed below, including but not limited to parenteral (e.g., by intracisternal injection and infusion techniques), intradermal, transmembranal, transdermal (including topical), intramuscular, intraperitoneal, intravenous, intra-arterial, intralesional, subcutaneous, oral, and intranasal (e.g., inhalation) routes of administration. Conjugate vaccines can be administered by bolus injection or by continuous infusion, as well as by localized administration, e.g., at a site of disease or injury. The conjugate vaccine can be optionally administered in a pharmaceutically or physiologically acceptable vehicle.

The term "vaccine" as used herein, is a broad term and is used in its ordinary sense, including, without limitation, conjugates of preferred embodiments or other antigens formulated with adjuvants, diluents, excipients, carriers, and other pharmaceutically acceptable substances. The term "pharmaceutically acceptable" is used to refer to a non-toxic material that is compatible with a biological system such as a cell, cell culture, tissue, or organism.

Immunization protocols for use with the conjugates of preferred embodiments provide compositions and methods for preventing or treating a disease, disorder and/or infection in a subject. The term "treating" as used herein, is a broad term and is used in its ordinary sense, including, without limitation, curative, preventative, prophylactic, palliative and/or ameliorative treatment.

The vaccine compositions are preferably sterile and contain either a therapeutically or prophylactically effective amount of the conjugate in a unit of weight or volume suitable for administration to a subject. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The characteristics of the carrier depend on the route of administration. Physiologically and pharmaceutically-acceptable carriers include diluents, fillers, salts, buffers, stabilizers, solubilizers, and other materials which are well known in the art.

The components of the pharmaceutical compositions also are capable of being co-mingled with the conjugates of the preferred embodiment, and with each other, in a manner such that there is no interaction which substantially impairs the desired pharmaceutical efficacy.

Formulation of the conjugate vaccines of preferred embodiments into pharmaceutical compositions can be accomplished using methods known in the art. The vaccine compositions can also contain one or more adjuvants. Suitable adjuvants include, for example, aluminum adjuvants, such as aluminum hydroxide or aluminum phosphate, Freund's Adjuvant, BAY, DC-chol, pcpp, monophoshoryl lipid A, CpG, QS-21, cholera toxin and formyl methionyl peptide. See, e.g., Vaccine Design, the Subunit and Adjuvant Approach, 1995 (M. F. Powell and M. J. Newman, eds., Plenum Press, N.Y.).

The dosage of conjugate vaccine to be administered a subject and the regime of administration can be determined in accordance with standard techniques well known to those of ordinary skill in the pharmaceutical and veterinary arts, taking into consideration such factors as the intended use, particular antigen, the adjuvant (if present), the age, sex, weight, species, general condition, prior illness and/or treatments, and the route of administration. Preliminary doses can be determined according to animal tests, and the scaling of dosages for human administration is performed according to art-accepted practices such as standard dosing trials. For example, the therapeutically effective dose can be estimated initially from serum antibody level testing. The dosage depends on the specific activity of the conjugate and can be readily determined by routine experimentation.

In practicing immunization protocols for treatment and/or prevention of specified diseases, a therapeutically effective amount of conjugate is administered to a subject. The "effective amount" means the total amount of therapeutic agent (e.g., conjugate) or other active component that is sufficient to show a meaningful benefit to the subject, such as, enhanced immune response, treatment, healing, prevention or amelioration of the relevant medical condition (disease, infection, or the like), or an increase in rate of treatment, healing, prevention or amelioration of such conditions. When "effective amount" is applied to an individual therapeutic agent administered alone, the term refers to that therapeutic agent alone. When applied to a combination, the term refers to combined amounts of the ingredients that result in the therapeutic effect, whether administered in combination, serially or simultaneously. As used herein, the phrase "administering an effective amount" of a therapeutic agent means that the subject is treated with said therapeutic agent(s) in an amount and for a time sufficient to induce an improvement, and preferably a sustained improvement, in at least one indicator that reflects the severity of the disease, infection, or disorder.

An improvement is considered "sustained" if the patient exhibits the improvement on at least two occasions separated by a period of time. The degree of improvement can be determined based, for example, on immunological data, or on signs or symptoms of a disease, infection, or disorder. Various indicators that reflect the extent of the patient's illness can be assessed for determining whether the amount and time of the treatment is sufficient. The baseline value for the chosen indicator or indicators can established based on by examination of the patient prior to administration of the first dose of the therapeutic agent, or based on statistical values generated from a population of healthy patients. If the therapeutic agent is administered to treat acute symptoms, the first dose is administered as soon as practically possible. Improvement is induced by administering therapeutic agents until the subject manifests an improvement over baseline for the chosen indicator or indicators. In treating chronic conditions, this degree of improvement is obtained by repeatedly administering the therapeutic agents over a period time, e.g., for one, two, or three months or longer, or indefinitely. A single dose can be sufficient for treating or preventing certain conditions. Treatment can be continued indefinitely at the same level or at a reduced dose or frequency, regardless of the patient's condition, if desired. Once treatment has been reduced or discontinued, it later can be resumed at the original level if symptoms reappear.

Generally, the amount of conjugate that provides an efficacious dose or therapeutically effective dose for vaccination against bacterial infection is from about 1 µg or less to about 100 µg or more, preferably from about 2, 3, 4, 5, 6, 7, 8, 9, 10, 15, 20, 25, 30, 35, 40, 45 or 50 µg to about 55, 60, 65, 70, 75, 80, 85, 90, or 95 µg per kg body weight. An efficacious dosage can require less antibody if the post-infection time elapsed is less, since there is less time for the bacteria to proliferate. An efficacious dosage can also depend on the bacterial load at the time of diagnosis. Multiple injections administered over a period of days can be considered for therapeutic usage.

The conjugate vaccines can be administered as a single dose or in a series including one or more boosters. For example, an infant or child can receive a single dose early in life, then be administered a booster dose up to 1, 2, 3, 4, 5, 6, 7, 8, 9, 10 or more years later. The booster dose generates antibodies from primed B-cells, i.e., an anamnestic response. That is, the conjugate vaccine elicits a high primary functional antibody response in infants or children, and is capable of eliciting an anamnestic response following a booster administration, demonstrating that the protective immune response elicited by the conjugate vaccine is long-lived.

The conjugate vaccines can be formulated into liquid preparations for, e.g., oral, nasal, anal, rectal, buccal, vaginal, peroral, intragastric, mucosal, perlinqual, alveolar, gingival, olfactory, or respiratory mucosa administration. Suitable forms for such administration include suspensions, syrups, and elixirs. The conjugate vaccines can also be formulated for parenteral, subcutaneous, intradermal, intramuscular, intraperitoneal or intravenous administration, injectable administration, sustained release from implants, or administration by eye drops. Suitable forms for such administration include sterile suspensions and emulsions. Such conjugate vaccines can be in admixture with a suitable carrier, diluent, or excipient such as sterile water, physiological saline, glucose, and the like. The conjugate vaccines can also be lyophilized. The conjugate vaccines can contain auxiliary substances such as wetting or emulsifying agents, pH buffeting agents, gelling or viscosity enhancing additives, preservatives, flavoring agents, colors, and the like, depending upon the route of administration and the preparation desired. Standard texts, such as "Remington: The Science and Practice of Pharmacy", Lippincott Williams & Wilkins; 20th edition (Jun. 1, 2003) and "Remington's Pharmaceutical Sciences", Mack Pub. Co.; 18th and 19th editions (December 1985, and June 1990, respectively), incorporated herein by reference in their entirety, can be consulted to prepare suitable preparations, without undue experimentation. Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysoleeithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

The conjugate vaccines are preferably provided as liquid suspensions or as freeze-dried products. Suitable liquid preparations include, e.g., isotonic aqueous solutions, suspensions, emulsions, or viscous compositions that are buffered to a selected pH. Transdermal preparations include lotions, gels, sprays, ointments or other suitable techniques. If nasal or respiratory (mucosal) administration is desired (e.g., aerosol inhalation or insufflation), compositions can be in a form and dispensed by a squeeze spray dispenser, pump dispenser or aerosol dispenser. Aerosols are usually under pressure by means of a hydrocarbon. Pump dispensers can preferably dispense a metered dose or a dose having a particular particle size, as discussed below.

When in the form of solutions, suspensions and gels, formulations of the conjugate can typically contain a major amount of water (preferably purified water) in addition to the active ingredient. Minor amounts of other ingredients such as pH adjusters, emulsifiers, dispersing agents, buffering agents, preservatives, wetting agents, jelling agents, colors, and the like can also be present.

The compositions are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the compositions can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener can depend upon the agent selected. The important point is to use an amount that can achieve the selected viscosity. Viscous compositions are normally prepared from solutions by the addition of such thickening agents.

A pharmaceutically acceptable preservative can be employed to increase the shelf life of the compositions. Benzyl alcohol can be suitable, although a variety of preservatives including, for example, parabens, thimerosal, chlorobutanol, or benzalkonium chloride can also be employed. A suitable concentration of the preservative can be from 0.02% to 2% based on the total weight although there can be appreciable variation depending upon the agent selected.

Pulmonary delivery of the conjugate can also be employed. The conjugate is delivered to the lungs of a mammal while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of the conjugate. Typically, each formulation is specific to the type of device employed and can involve the use of an appropriate propellant material, in addition to diluents, adjuvants and/or carriers useful in therapy.

The conjugate is advantageously prepared for pulmonary delivery in particulate form with an average particle size of from 0.1 µm or less to 10 µm or more, more preferably from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm for pulmonary delivery. Pharmaceutically acceptable carriers for pulmonary delivery of the conjugates include carbohydrates such as trehalose, mannitol, xylitol, sucrose, lactose, and sorbitol. Other ingredients for use in formulations can include DPPC, DOPE, DSPC and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Formulations suitable for use with a nebulizer, either jet or ultrasonic, typically comprise the conjugate dissolved or suspended in water at a concentration of about 0.01 or less to 100 mg or more of conjugate per mL of solution, preferably from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg of conjugate per mL of solution. The formulation can also include a buffer and a simple sugar (e.g., for protein stabilization and regulation of osmotic pressure). The nebulizer formulation can also contain a surfactant, to reduce or prevent surface induced aggregation of the conjugate caused by atomization of the solution in forming the aerosol.

Formulations for use with a metered-dose inhaler device generally comprise a finely divided powder containing the inventive compound suspended in a propellant with the aid of a surfactant. The propellant can include conventional propellants, such chlorofluorocarbon, a hydrochlorofluorocarbons, hydrofluorocarbons, and hydrocarbons, such as trichlorofluoromethane, dichlorodifluoronethane, dichlorotetrafluoroethanol, and 1,1,1,2-tetrafluoroethane, and combinations thereof.

Suitable surfactants include sorbitan trioleate, soya lecithin, and oleic acid.

Formulations for dispensing from a powder inhaler device typically comprise a finely divided dry powder containing the conjugate, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, preferably from about 5, 10, 15, 20, 25, 30, 35, 40, 45, or 50 wt. % to about 55, 60, 65, 70, 75, 80, 85, or 90 wt. % of the formulation.

When the conjugate is administered by intravenous, cutaneous, subcutaneous, or other injection, the conjugate vaccine is preferably in the form of a pyrogen-free, parenterally acceptable aqueous solution. The preparation of parenterally acceptable solutions with suitable pH, isotonicity, stability, and the like, is within the skill in the art. A preferred pharmaceutical composition for injection preferably contains an isotonic vehicle such as Sodium Chloride Injection, Ringer's Injection, Dextrose injection, Dextrose and Sodium Chloride Injection, Lactated Ringer's Injection, or other vehicles as are known in the art. The pharmaceutical compositions can also contain stabilizers, preservatives, buffers, antioxidants, or other additives known to those of skill in the art.

The duration of the injection can vary depending upon various factors, and can comprise a single injection administered over the course of a few seconds or less, to 1, 2, 3, 4, 5, 6, 7, 8, 9, 10, 11, 12, 13, 14, 15, 16, 17, 18, 19, 20, 21, 22, 23, or 24 hours or more of continuous intravenous administration.

The conjugate can be administered topically, systematically, or locally, via a liquid or gel, or as an implant or device.

The conjugates of preferred embodiments, or the conjugation methods of preferred embodiments, can be useful in preparing vaccines for the treatment of a variety of bacterial infections, including infections by *Helicobacter pyloris, Borelia burgdorferi, Legionella pneumophilia, Mycobacteria* sps, (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalaciae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoiae, Pasturella multocida, Bacteroides, Fusobacterium nucleatum, Streptobacillus moniliformis, Treponema pallidium, Treponema pertenue, Leptospira*, and *Actinomyces israeli*.

Certain methods of the preferred embodiments can also be of use in preparing vaccines for treating or vaccinating subjects against cancer, such as mammalian sarcomas and carcinomas, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, serminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuron, oligodendroglioma, meningioma, melanoma, neuroblastoma, retinoblastoma; leukemias, such as acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia Vera, lymphoma (Hodgkin's disease and non-Hodgkin's disease), multiple myeloma, Waldenstrom's macroglobulinemia, and heavy chain disease, lymphoproliferative disorders including autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Ban virus-positive T cell lymphoma, histiocytic lymphoma, Hodgkin's disease, diffuse aggressive lymphoma, acute lymphatic leukemias, T gamma lyrnphoproliferative disease, cutaneous B cell lymphoma, cutaneous T cell lymphoma (i.e., mycosis fungoides) and Szary syndrome.

The conjugates can be administered in combination with various vaccines either currently being used or in development, whether intended for human or non-human subjects. Examples of vaccines for human subjects and directed to infectious; diseases include the combined diphtheria and tetanus toxoids vaccine; pertussis whole cell vaccine; the inactivated influenza vaccine; the 23-valent pneumococcal vaccine; the live measles vaccine; the live mumps vaccine; live rubella vaccine; Bacille Calmette-Guerin I (BCG) tuberculosis vaccine; hepatitis A vaccine; hepatitis B vaccine; hepatitis C vaccine; rabies vaccine (e.g., human diploid cell vaccine); inactivated polio vaccine; meningococcal polysaccharide vaccine; quadrivalent meningococcal conjugate vaccine; yellow fever live virus vaccine; typhoid killed whole cell vaccine; cholera vaccine; Japanese B encephalitis killed virus vaccine; adenovirus vaccine; cytomegalovirus vaccine; rotavirus vaccine; varicella vaccine; anthrax vaccine; small pox vaccine; and other commercially available and experimental vaccines.

The conjugates can be provided to an administering physician or other health care professional in the form of a kit. The kit is a package which houses a container which contains the conjugate vaccine and instructions for administering the conjugate vaccine to a subject. The kit can optionally also contain one or more other therapeutic agents. The kit can optionally contain one or more diagnostic tools and instructions for use. For example, a vaccine cocktail containing two or more vaccines can be included, or separate pharmaceutical compositions containing different vaccines or therapeutic agents. The kit can also contain separate doses of the conjugate vaccine for serial or sequential administration. The kit can contain suitable delivery devices, e.g., syringes, inhalation devices, and the like, along with instructions for administrating the therapeutic agents. The kit can optionally contain instructions for storage, reconstitution (if applicable), and administration of any or all therapeutic agents included. The kits can include a plurality of containers reflecting the number of administrations to be given to a subject. If the kit contains a first and second container, then a plurality of these can be present.

EXAMPLES

Materials and Methods

Materials—

Tetanus toxoid (TT) was from Lederle Vaccines, Pearl River, N.Y. and Serum Institute of India, Pune, India. Meningococcal groups A and C polysaccharides (Mn A PS and Mn C PS, respectively) were from Bio-Manguinhos, Rio de Janeiro, Brazil. Mn A PS was also obtained from SynCo Bio Partners, Amsterdam, The Netherlands. Mn W135 and Y PS's were from Aventis Pasteur and Chiron. Pneumococcal (Pn) and *Haemophilus influenzae* type b (Hib) polysaccharides were from Wyeth. Hydrazine, carbohydrazide, adipic acid dihydrazide (ADH), acetic hydrazide, 1-[3-(dimethylamino)propyl]-3-ethyl carbodiimide hydrochloride (EDC), N-(2-

Hydroxyethyl)piperazine-N'-(2-ethanesulfonic acid) (HEPES), sodium periodate, sodium borohydride, sodium cynoborohydride, 4-cyno-dimethylamino pyridium tetrafluoroborate (CDAP), and 1-amino-2,3-propanediol, and various amino acids were purchased from Sigma/Aldrich Chemical Company. TNBSA (2,4,6-trinitrobenzenesulfonic acid) and BCA (bicinchoninic acid) assay kits were purchased from Pierce.

Methods—

As described above, there is disclosed herein a method for activation of protein with hydrazide groups catalyzed by carbodiimide in the presence of amino acids, amino acid mixture, peptides and peptide mixtures, and three general methods for conjugating polysaccharides and mixtures of polysaccharides to proteins. The bacterial polysaccharides used for conjugation to protein by these methods include Meningococcal serogroups A, C, W135 and Y polysaccharides.

Activation of Protein with Hydrazide Groups Catalyzed by Carbodiimide in the Presence of Amino Acids, Amino Acid Mixture, Peptides and Peptide Mixtures 1. Protein (tetanus toxoid or TT, 4 mg/mL, measured by Lowry assay [26] or BCA assay [35]) reacted with 0.36 M hydrazine or adipic acid dihydrazide (ADH) in the presence of 12-72 mM EDC, 0.2 M MES, pH 5-6.5 and 0-144 mM amino acid or amino acid mixture for 1-24 hours.
2. The reaction mixture was neutralized with 1 N NaOH and dialyzed against 30 mM NaCl, 10 mM HEPES, pH 7.5, 4° C.
3. After dialysis, the samples were recorded for precipitate formation.
4. Samples were stored at 4° C. for 1-8 weeks, precipitate formation was examined and recorded.
5. The samples showing little or no precipitate were analyzed by HPLC with a Superose 6 column.
6. Protein concentration is determined by BCA assay [35], and hydrazide concentration is determined by TNBS assay [34]. Number of hydrazide group per TT molecule, i.e. degree of activation (DA), is calculated.

General Method a for Conjugation—Aldehyde-Activated PS or PS Mixture Reacting with Hydrazide-Activated Protein (Reductive Amination Conjugation)

1. Two methods were used to activate tetanus toxoid. Tetanus toxoid was activated with hydrazine or adipic acid dihydrazide in the presence of EDC at pH 5.5-6.5 and then buffer exchanged with 30 mM NaCl, 3 mM $Na_2CO_3$, pH about 10.5. Alternatively, tetanus toxoid was activated with hydrazine or adipic acid dihydrazide in the presence of EDC at pH 5.5 and 0-144 mM amino acid or mixture of amino acid, and then buffer exchanged with 30 mM NaCl, 10 mM HEPES, pH 7.5, 4° C.
2. Polysaccharide or a mixture of polysaccharides (at a desired weight ratio of the component polysaccharides) was activated with $NaIO_4$, and buffer exchanged with 10 mM HEPES, pH 7.5, 4° C.
3. Hydrazide-activated TT was reacted with aldehyde-activated polysaccharide or polysaccharide mixture at ratios from 2:1 to 1:2 and concentration range of 1-40 mg/mL overnight, pH 6.5-7.5, 4-40° C.
4. $NaBH_4$ (ten-fold moles of the aldehyde groups in the initial reactant) was then added for 6 hrs to overnight to reduce the C=N double bond to C—N single bond and also reduce the unreacted aldehyde groups to alcohol.
5. The solution was buffer-exchanged with saline, 10 mM HEPES, pH 7.5, 1 mM EDTA using a 12-14 KDa molecular weight cut-off membrane.
6. The volume of the sample was determined.
7. Protein concentration was calculated based on the initial starting quantity measured by Lowry assay [26] or BCA assay [35].
8. Polysaccharide concentration was calculated based on the initial starting quantity measured by appropriate assay methods for each component polysaccharide before mixing, e.g. resorcinol assay [27] for Mn A and C PS's, anthrone assay [32] for Mn W135 and Y PS's, phosphorus assay [33] for Mn A PS, and purpald assay [31] for Mn W135 and Y PS's.

General Method B for Conjugation—Cyanate-Activated PS or PS Mixture Reacting with Hydrazide-Activated Protein (Cyanylation Conjugation)

1. Two methods were used to activate tetanus toxoid. Tetanus toxoid was activated with hydrazine or adipic acid dihydrazide in the presence of EDC at pH 5.5-6.5 and then buffer exchanged with 30 mM NaCl, 3 mM $Na_2CO_3$, pH about 10.5. Alternatively, tetanus toxoid was activated with hydrazine or adipic acid dihydrazide in the presence of EDC at pH 5.5 and 0-144 mM amino acid or amino acid mixture, and then buffer exchanged with 30 mM NaCl, 10 mM HEPES, pH 7.5, 4° C.
2. Polysaccharide or a mixture of polysaccharides (at a desired weight ratio of the component polysaccharides) was activated with CDAP for 2-2.5 minutes at 20-24° C. in the presence of triethylamine.
3. At 4° C., hydrazide-activated TT was reacted with cyanate-activated polysaccharide or polysaccharide mixture at ratios from 2:1 to 1:2 and concentration range of 0.2-1 mg/mL, pH 6.5-7.5.
4. After reaction for 3 overnights at 4° C., (The prolonged incubation is to ensure decomposition of the residual leftover unreacted cyanate groups), the solution was buffer-exchanged with saline, 10 mM HEPES, pH 7.5, 1 mM EDTA using a 12-14 KDa molecular weight cut-off membrane.
5. The volume of the sample was determined.
6. Protein concentration was calculated based on the initial starting quantity measured by Lowry assay [26] or BCA assay [35].
7. Polysaccharide concentration was calculated based on the initial starting quantity measured by appropriate assay methods for each component polysaccharide before mixing, e.g. resorcinol assay [27] for Mn A and C PS's, anthrone assay [32] for Mn W135 and Y PS's, phosphorus assay [33] for Mn A PS, and purpald assay [31] for Mn W135 and Y PS's.

The conjugation time for reaction of method B to prepare combined synthesized multi-valent conjugate vaccines without use of a blocking agent is 3 overnights at 4° C. Because of high conjugation yield and the high immunogenicity of the conjugation product, purification process such as column chromatography and/or ammonium sulfate precipitation of the conjugate from unconjugated polysaccharide are necessary.

General Method C for Conjugation—Hydrazide-Activated PS or PS Mixture Reacting with Aldehyde-Activated Protein (Reductive Amination Conjugation)

1. Two methods were used to activate tetanus toxoid. Tetanus toxoid was reacted with 1-amino-2,3-propanediol (APDO) in the presence of EDC at pH 5.5-6.5 and then buffer-exchanged with 30 mM NaCl, 3 mM $Na_2CO_3$, pH about 10.5, 4° C. TT-APDO was reacted with $NaIO_4$ to create aldehyde groups and then buffer exchanged with 30 mM NaCl, 3 mM $Na_2CO_3$, pH about 10.5, 4° C. Alternatively, tetanus toxoid was reacted with 1-amino-2,3-propanediol (APDO) in the presence of EDC at pH 5.5-6.5 and 0-144 mM amino acid or amino acid mixture, and then buffer exchanged with 30 mM NaCl, 10 mM HEPES, pH 7.5, 4° C. TT-APDO was reacted with $NaIO_4$ to create aldehyde groups and then buffer exchanged with 30 mM NaCl, 10 mM HEPES, pH 7.5, 4° C.

2. Three methods were used to prepare hydrazide-activated polysaccharide or polysaccharide mixture (at a desired weight ratio of the component polysaccharides): a) PS or PS mixture was reacted with $NaIO_4$ and then hydrazine or adipic acid dihydrazide with subsequent reduction with $NaBH_4$ (reductive amination); b) PS or PS mixture was activated with CDAP and then reacts with hydrazine or adipic acid dihydrazide (cyanylation conjugation reaction); and c) PS or PS mixture was reacted with hydrazine or adipic acid dihydrazide in the presence EDC (carbodiimide reaction).

3. Aldehyde-activated TT was reacted with hydrazide-activated PS or PS mixture at ratios from 2:1 to 1:2 and concentration range 1-5 mg/mL for 18 hours, pH 6.5-7.5, 4-40° C.

4. $NaBH_4$ (ten-fold moles of the aldehyde in the initial reactant) was then added for 6 hrs—overnight to reduce the C=N double bond to C—N single bond and also reduce the unreacted aldehyde groups to alcohol.

5. The solution was buffer-exchanged with saline, 10 mM HEPES, pH 7.5, 1 mM EDTA using a 12-14 KDa molecular weight cut-off membrane.

6. The volume of the sample was determined.

7. Protein concentration was calculated based on the initial starting quantity measured by Lowry assay [26] or BCA assay [35].

8. Polysaccharide concentration was calculated based on the initial starting quantity measured by appropriate assay methods for each component polysaccharide before mixing, e.g. resorcinol assay [27] for Mn A and C PS's, anthrone assay [32] for Mn W135 and Y PS's, phosphorus assay [33] for Mn A PS, and purpald assay [31] for Mn W135 and Y PS's.

Physico-Chemical Assays of Activated Protein and Conjugate Products

High Performance Liquid Size-Exclusion Chromatography (HPSEC)

Samples of proteins, polysaccharides and conjugate products (25 uL, 0.05-1 mg/mL) were run through a Waters Ultrahydrogel 2000 or Ultrahydrogel Linear column, or a Superose 6 column with saline, 10 mM Tris, pH 7.5, 1 mM EDTA at 0.5 mL/minute in Dionex HPLC system using Chromelean software and a UV detector at 280 nm. The UV detector at 280 nm monitors the signals of protein-containing species as well as compounds containing aromatic moieties. The RI detector measures the signals of proteins, polysaccharides, conjugates and salts. When the combined synthesized multi-valent conjugate vaccines were analyzed by HPLC, fractions were collected each minute for detection of the polysaccharide-protein conjugate by ELISA.

ELISA Method for Detection of PS-Protein Conjugate

Immunolon 1 plates (Dynatech) were coated with 20 uL of each HPLC fraction plus 80 uL 1×PBS (a total volume of 100 µL coating solution) for 3 hours. Only the protein-containing molecular species (i.e. conjugates and un-conjugated free protein) adhere to the polystyrene plate. After washing three times with 150 uL washing buffer (PBS with 0.05% Tween 20, 0.02% $NaN_3$), 100 uL of respective PS-specific (but not cross-reactive to carrier protein) anti-serum (1/100-1/250, diluted with buffer containing PBS, 5% new born calf serum, 0.02% $NaN_3$) was added to each well. After overnight incubation, the plate was washed three times and incubated with 100 uL goat anti-mouse IgG Fc conjugated with alkaline phosphatase (1/10,000 dilution in dilution buffer) for three hours. After washing (3×150 uL) the plates were incubated with 100 uL p-nitrophenyl phosphate (1 mg/mL in 1 M Tris, pH 9.8, 0.3 mM $MgCl_2$) for 30-180 minutes and the ELISA readings at 405 nm were measured with a plate reader. After subtracting the background, the reading representing the conjugated PS in each fraction since the un-conjugated free PS does not stick or adhere to the plate during plate coating. The presence of all the component polysaccharide species in the combined synthesized multi-valent conjugate vaccines was thus demonstrated.

Immunogenicity of Polysaccharide-Protein Conjugates in Mice

Immunization of Mice

Unless specified, mice (NIH-Swiss; groups of 5 or 10) were immunized with 1 µg/dose of each polysaccharide (in PS mixture or in the conjugates prepared by conjugation Methods A, B and C) on days 0, 14 and 28 with antisera collected on day 42. ELISA was carried out for determination of antibody levels against respective native polysaccharides.

ELISA Method for Determination of Antibody Titer

Immunolon 1 plates (Dynatech) were coated for 18 hours with 100 µL coating solution containing polysaccharide and methylated human serum albumin (mHSA) with specific concentrations for each polysaccharide listed in the following Table.

| PS | [Polysaccharide], µg/mL | [mHSA], µg/mL |
| --- | --- | --- |
| 1 | 5 | 2 |
| 3 | 5 | 1 |
| 4 | 2.5 | 1 |
| 5 | 5 | 5 |
| 6B | 2 | 5 |
| 7F | 5 | 5 |
| 9V | 2.5 | 2.5 |
| 14 | 1 | 0.5 |
| 18C | 5 | 5 |
| A | 5 | 5 |
| C | 5 | 5 |
| W135 | 5 | 5 |
| Y | 5 | 5 |
| Hib | 10 | 1.25 |

After washing three times with 150 uL washing buffer (PBS with 0.05% Tween 20, 0.02% $NaN_3$), 100 uL of specific anti-serum samples and reference serum (with arbitrarily assigned 3200 units/mL anti-polysaccharide antibody; duplicate) at a serial two-fold dilution starting from 1/200 (diluted with dilution buffer containing PBS, 4% new born calf serum, 0.02% $NaN_3$ with 2 µg/mL cell wall polysaccharide in pneumococcal cases), was added to each well. After overnight incubation, the plates were washed three times and incubated with 100 uL goat anti-mouse IgG Fc conjugated with alkaline phosphate (1/10,000 dilution in dilution buffer) for two hours. After washing (3×150 uL) the plates were incubated with 100 uL p-nitrophenyl phosphate (1 mg/mL in 1 M Tris, pH 9, 0.3 mM $MgCl_2$) for 30-45 minutes and the reaction was stopped by 50 uL 1 N NaOH. The ELISA procedure for Hib polysaccharide was carried at 4° C. or on ice except for the step of color development with substrate. The ELISA readings were measured at 405 nm with a plate reader and the anti-polysaccharide antibody levels of the antiserum samples were calculated from their ELISA readings and the standard curve of the reference serum co-assayed in the same plate. The geometric mean of antibody level for each mouse group was calculated.

Bactericidal Assay for Determination of Biological Functionality of Antibody (Bactericidal Titer)

The biological function of the induced antibody was determined by bactericidal assay of the induced antisera against the homologous bacterial strain according to the method in [Maslanka S E, Gheesling L L, Libutti D E, Donaldson K B, Harakeh H S, Dykes J K et al. Standardization and a multi-laboratory comparison of *Neisseria meningitidis* serogroup A and C serum bactericidal assays. The Multilaboratory Study Group. Clin Diagn Lab Immunol 1997; 4(2):156-167.] with minor modifications. Briefly, bacteria were first cultured overnight on a brain heart infusion (BHI)/5% normal horse serum (NHS) plate, and then transferred to a fresh plate and cultured for 4-5 hours. Prepared a bacterial suspension of 80% transmittance at 530 nm in DPBS from the fresh 4-5 hours culture, and dilute it to 50-80 colony-forming unit (CFU)/25 uL with DPBS (approximately 1:50,000 dilution). Thawed the complement at room temperature while preparing the bacterial dilution and stored it on ice until use. In a 96-well tissue culture plate, a series of 2-fold dilutions of test and control samples was carried out with DPBS containing 0.5 mM $MgCl_2$ and 0.9 mM $CaCl_2$. Added 25 uL bacterial suspension to each well followed by 25 uL complement (Lot #34426-A, Pel-Freez, Rogers, Aakansas). After incubation at 37° C. for 30 min without $CO_2$, 10 uL of bacterial suspension from each well was plated. The colonies were counted after overnight incubation at 37° C. with 5% $CO_2$. The bactericidal titer is the highest dilution of the test sample yielding a 50% reduction in CFU as compared to the control well containing complement without antiserum.

Specific Examples

Activation of Protein with Hydrazine or Hydrazide Catalyzed by Carbodiimide Under Controlled Conditions Including Reaction Time, the Concentration of EDC and the Concentration of Amino Acids and Amino Acid Mixture It has been reported that protein reaction with hydrazine or di-hydrazide catalyzed by EDC tends to result in aggregation and precipitation of the product. Several reaction conditions for reacting 4 mg/mL TT with 0.36 M hydrazine or ADH were explored in order to attain the reaction product without precipitation.

Activation Reaction in the Absence of Amino Acid

In the absence of amino acid, the reaction was carried out in the presence of 12-48 mM EDC for 1-24 hours. The reaction mixture was buffer-exchanged with 30 mM NaCl, 10 mM HEPES, pH 7.5 and stored at 4° C. Some products of these reactions formed precipitate during the reaction or after storing the dialyzed product at 4° C. for 1-8 weeks. The degree of activation (DA; number of hydrazide group per TT molecule) of the remaining samples was determined and listed in Table 3. The HPLC profiles of some of these products are shown in FIG. 1.

TABLE 3

Degree of activation (DA; number of hydrazide group per TT molecule) for activated tetanus toxoid resulted from various activation conditions in the absence of amino acid.

| [EDC] | Reaction time for hydrazine (hours) | | | | Reaction time for ADH (hours) | | | |
|---|---|---|---|---|---|---|---|---|
| (mM) | 1 | 2 | 4 | 24 | 1 | 2 | 4 | 24 |
| 12 | —[a] | — | — | (92)[b] | 49 | — | — | — |
| 18 | — | (110) | (81) | (99) | — | — | — | — |
| 24 | — | (83) | (90) | (107) | — | — | — | — |
| 36 | (77) | (96) | (102) | (112) | — | — | 75 | 66 |
| 48 | — | — | — | — | — | 76 | 77 | (103) |

[a]DA is not determined for sample showing precipitate.
[b]The number in parenthesis is the DA value of the sample without precipitation but showing substantial reduction of protein signal in HPLC profile (FIG. 1, Profiles A and B).

Figure 2:
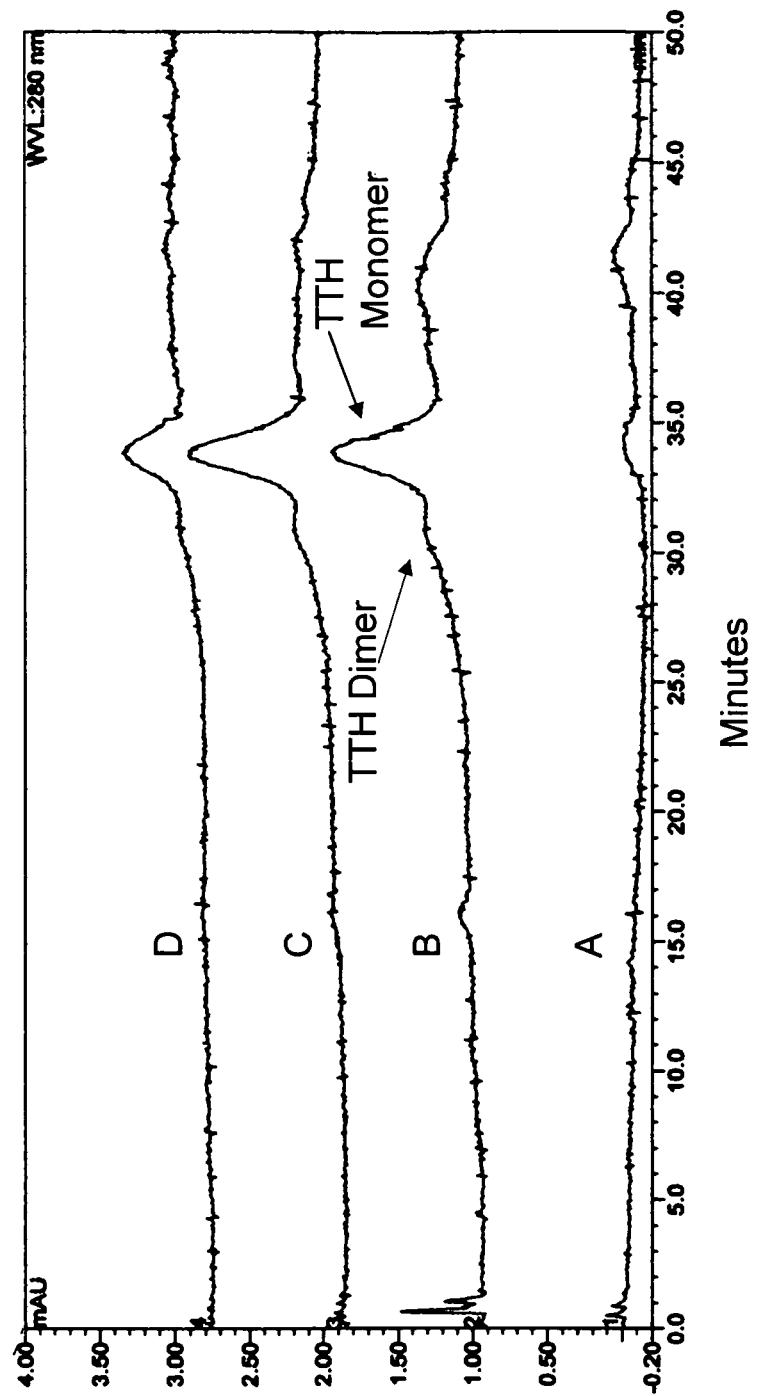
FIG. 2 HPLC profiles (280 nm, by a Superose 6 column) of tetanus toxoid activation product (TTH) with hydrazine or adipic acid dihydrazide (ADH) catalyzed by various EDC concentrations in the presence of different lysine concentrations and reaction times. The reaction conditions are: (A) hydrazine, 24 mM EDC, 36 mM lysine for 2 hours; (B) hydrazine, 12 mM EDC, 144 mM lysine for 2 hours; (C) ADH, 12 mM EDC, 36 mM lysine for 1 hour; and (D) ADH, 12 mM EDC, 72 mM lysine for 4 hours. Only small fraction of the product passes through the column and shows a shadow peak at 34 minute in profile (A). The product passes through the column and shows a major peak at 34 minute for monomer and a minor peak at 31 minute for dimmer in profiles (B), (C) and (D).

Activation Reaction in the Presence of Lysine, Arginine, Histidine, Glycine, Serine, Threonine and Amino Acid Mixture of Lysine, Arginine, Histidine, Glycine, Serine, Threonine, Glutamic Acid and Cysteine Reaction of tetanus toxoid (4 mg/mL) with 0.36 M hydrazine and ADH catalyzed by 12 and 24 mM EDC in the presence of 36, 72 and 144 mM of amino acid lysine, arginine, threonine, serine, glycine, histidine, or an amino acid mixture composed of equal molarity of lysine, arginine, threonine, serine, glycine, histidine, glutamic acid and cysteine was carried out for 1, 2, 4 and 24 hours. The degree of activation (DA) of the reaction products without precipitation was determined and listed in Table 4. The HPLC profiles of some of these products are shown in FIG. 2.

TABLE 4

Degree of activation (Da; number of hydrazide group per TT molecule) for activated tetanus toxoid resulted from various activation conditions in the presence of amino acid lysine, arginine, threonine, serine, glycine, histidine or amino acid mixture.

| [EDC] | | Reaction time for hydrazine (hours) | | | | Reaction time for ADH (hours) | | | |
|---|---|---|---|---|---|---|---|---|---|
| (mM) | (mM) | 1 | 2 | 4 | 24 | 1 | 2 | 4 | 24 |
| | [Lys] | | | | | | | | |
| 12 | 36 | —[a] | — | — | — | 47 | — | — | — |
| | 72 | — | — | — | — | 39 | 40 | 57 | — |
| | 144 | 32 | — | — | — | 34 | 43 | 43 | 58 |
| 24 | 36 | — | (95)[b] | (88) | (93) | — | — | (92) | (90) |
| | 72 | — | — | (103) | (106) | — | — | — | — |
| | 144 | — | — | — | — | — | — | — | — |
| | [Arg] | | | | | | | | |
| 12 | 36 | — | — | — | — | 48 | — | — | — |
| | 72 | — | — | — | — | 40 | 46 | 56 | — |
| | 144 | 36 | — | — | — | 36 | 42 | 48 | 57 |

TABLE 4-continued

Degree of activation (Da; number of hydrazide group per TT molecule) for activated tetanus toxoid resulted from various activation conditions in the presence of amino acid lysine, arginine, threonine, serine, glycine, histidine or amino acid mixture.

| [EDC] (mM) | (mM) | Reaction time for hydrazine (hours) | | | | Reaction time for ADH (hours) | | | |
|---|---|---|---|---|---|---|---|---|---|
| | | 1 | 2 | 4 | 24 | 1 | 2 | 4 | 24 |
| 24 | 36 | — | (86) | (83) | (92) | — | — | (87) | (93) |
| | 72 | — | — | (105) | (101) | — | — | — | — |
| | 144 | — | — | — | — | — | — | — | — |
| | [Thr] | | | | | | | | |
| 12 | 36 | — | — | — | — | 47 | — | — | — |
| | 72 | — | — | — | — | 38 | 46 | 52 | — |
| | 144 | 35 | — | — | — | 32 | 42 | 46 | 48 |
| 24 | 36 | — | (112) | (88) | (96) | — | — | (87) | (88) |
| | 72 | — | — | — | — | — | — | — | — |
| | 144 | — | — | — | — | — | — | — | — |
| | [Ser] | | | | | | | | |
| 12 | 36 | — | — | — | — | 47 | — | — | — |
| | 72 | 32 | — | — | — | 39 | 43 | 51 | 57 |
| | 144 | 35 | — | — | — | 41 | 40 | 44 | 47 |
| 24 | 36 | — | (114) | (82) | (91) | — | — | (91) | (93) |
| | 72 | — | — | — | — | — | — | — | — |
| | 144 | — | — | — | — | — | — | — | — |
| | [Gly] | | | | | | | | |
| 12 | 36 | — | — | — | — | 49 | — | — | — |
| | 72 | 35 | — | — | — | 37 | 45 | 47 | 54 |
| | 144 | 32 | 32 | 32 | 33 | 35 | 40 | 39 | 47 |
| 24 | 36 | — | — | — | — | — | — | — | (82) |
| | 72 | — | — | — | — | — | — | — | — |
| | 144 | — | — | — | — | — | — | — | — |
| | [His] | | | | | | | | |
| 12 | 36 | 41 | — | — | — | 44 | 46 | 58 | — |
| | 72 | 28 | 36 | 46 | — | 27 | 35 | 41 | 46 |
| | 144 | 21 | 27 | 30 | 39 | 24 | 30 | 33 | 40 |
| 24 | 36 | — | (85) | — | — | — | — | — | — |
| | 72 | — | — | — | — | 22 | — | — | — |
| | 144 | 65 | — | 48 | — | 40 | 44 | 58 | — |
| | [Mix] | | | | | | | | |
| 12 | 36 | 40 | — | — | — | 45 | 51 | 62 | — |
| | 72 | 12 | 12 | 13 | 17 | 19 | 17 | 18 | 22 |
| | 144 | 10 | 8 | 9 | 13 | 13 | 13 | 14 | 17 |
| 24 | 36 | — | — | — | — | 48 | — | — | — |
| | 72 | — | — | — | — | — | — | — | — |
| | 144 | 26 | 29 | 27 | — | 50 | 58 | 64 | 80 |

[a]DA is not determined for sample showing precipitate.

[b]The number in parenthesis is the DA value of the sample without precipitation but showing substantial reduction of protein signal in HPLC profile (FIG. 2, Profile A).

Activation Reaction in the Presence of Glutamic Acid (and Aspartic Acid)

Figure 3:
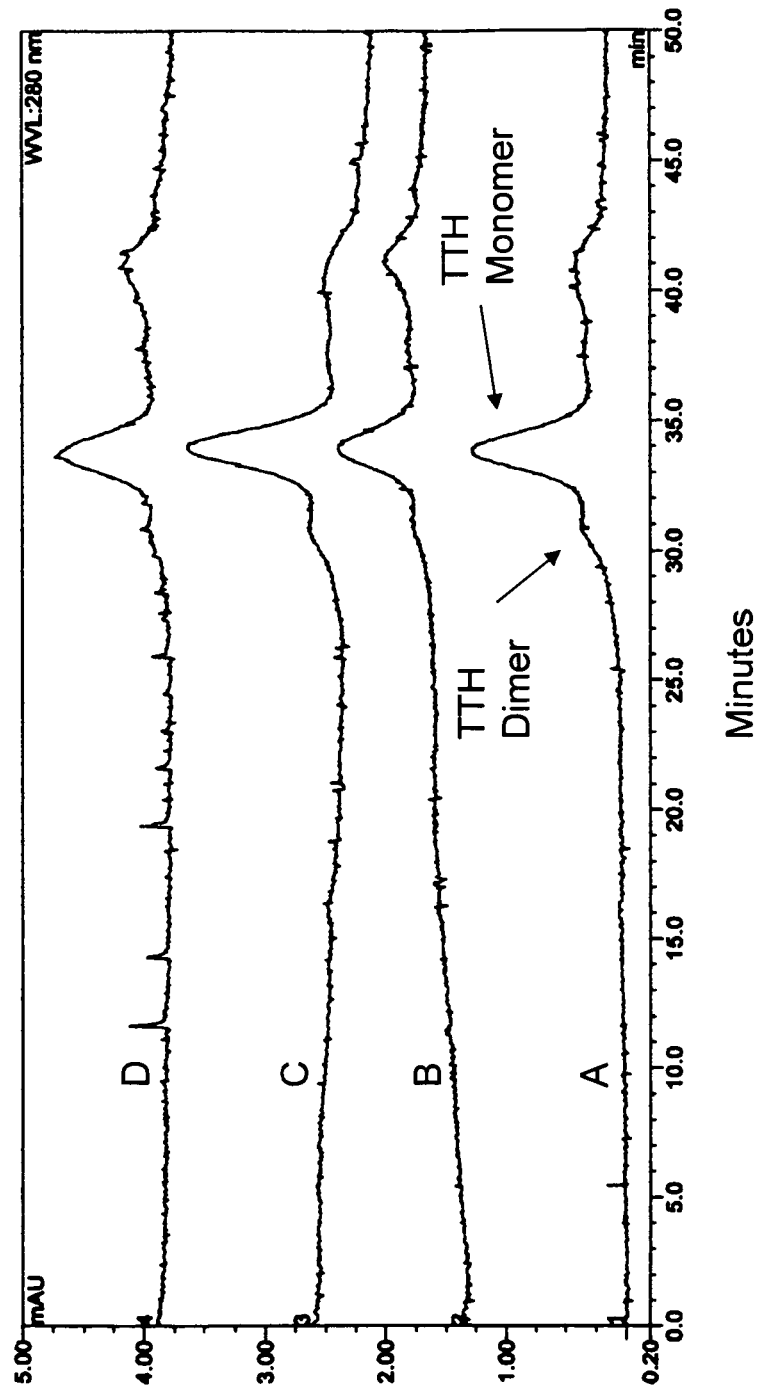
FIG. 3 HPLC profiles (280 nm, by a Superose 6 column) of tetanus toxoid activation product (TTH) with hydrazine or adipic acid dihydrazide (ADH) catalyzed by various EDC concentrations in the presence of 72 mM glutamic acid for various reaction times. The other reaction conditions are: (A) hydrazine, 24 mM EDC for 1 hour; (B) hydrazine, 48 mM EDC for 1 hour; (C) ADH, 24 mM EDC for 1 hour; and (D) ADH, 48 mM EDC for 2 hours. The product passes through the column and shows a major peak at 34 minute for monomer and a minor peak at 31 minute for dimer.

Reaction of tetanus toxoid (4 mg/mL) with 0.36 M hydrazine and ADH catalyzed by 12, 24, 48 and 72 mM EDC in the presence of 36, 72 and 144 mM of glutamic acid was carried out for 1, 2, 4 and 24 hours. The degree of activation (DA) of the reaction products without precipitation was determined and listed in Table 5. The HPLC profiles of some of these products are shown in FIG. 3.

TABLE 5

Degree of activation (DA; number of hydrazide group per TT molecule) foractivated tetanus toxoid resulted from various activation conditions in the presence ofglutamic acid.

| [EDC] (mM) | [Glu] (mM) | Reaction time for hydrazine (hours) | | | | Reaction time for ADH (hours) | | | |
|---|---|---|---|---|---|---|---|---|---|
| | | 1 | 2 | 4 | 24 | 1 | 2 | 4 | 24 |
| 12 | 36 | 19 | 21 | 26 | 27 | 35 | 35 | 35 | 39 |
| | 72 | 16 | 7 | 6 | 8 | 21 | 21 | 20 | 25 |
| | 144 | 5 | 5 | 12 | 15 | 16 | 17 | 18 | 21 |
| 24 | 36 | 33 | 35 | —[a] | — | 41 | 37 | 39 | 41 |
| | 72 | 23 | 23 | 25 | 30 | 36 | 37 | 36 | 41 |
| | 144 | 17 | 20 | 16 | 23 | 30 | 29 | 33 | 34 |
| 48 | 36 | — | — | — | — | — | — | — | — |
| | 72 | 49 | — | — | — | — | 54 | 49 | 59 |
| | 144 | 25 | 26 | 27 | 33 | 38 | 39 | 40 | 44 |
| 72 | 36 | — | (98)[b] | (80) | (92) | — | — | — | — |
| | 72 | — | — | — | — | — | — | — | — |
| | 144 | 34 | 35 | 37 | — | 46 | 46 | 46 | 53 |

[a]DA is not determined for sample showing precipitate.
[b]The number in parenthesis is the DA value of the sample without precipitation but showing substantial reduction of protein signal in HPLC profile.

Conjugation of Polysaccharide Mixtures to Proteins
Method A—Combined Synthesized Multivalent Meningococcal groups A, C, W135 and Y Polysaccharides-Tetanus Toxoid Conjugate Lot ACWY040228a1
Activation of TT to Contain Hydrazine Groups
 1. Tetanus toxoid (4.2 mg/mL) was activated with 0.42 M hydrazine in the presence of 20 mM EDC, 0.1 M MES, pH 6.5 at 20-24° C.
 2. After reacting for 4 hours, the pH of the reaction mixture was raised to 7.5-10 with 1 N NaOH to stop the reaction.
 3. The reaction mixture was buffer-exchanged with 30 mM NaCl, 3 mM $Na_2CO_3$, pH about 10.5 at 4° C. using a 12-14 KDa dialysis membrane.

Activation of Mn A, C, W135 and Y PS Mixture to Contain Aldehyde Groups
 1. Mn A, C, W135 and Y PS mixture (10 mg/mL, total PS; 2.5 mg/mL, each component PS) was reacted with 6 mM $NaIO_4$ at 20-24° C. for 4 hours.
 2. The sample was dialyzed against 10 mM HEPES, pH 7.5 at 4° C. using a 12-14 KDa dialysis membrane.

Conjugation of Activated Mn A, C, W135 and Y PS Mixture to Activated TT
 1. Aliquot of hydrazide-containing TT (0.4 mg) was adjusted to 10 mg/mL by lyophilization and dissolution in 0.04 mL water.
 2. Aliquot of aldehyde-containing Mn A, C, W135 and Y PS mixture was adjusted to 10 mg/mL by lyophilization and dissolution in 0.04 mL 0.2 M HEPES, pH 7.5, 30 mM EDTA.
 3. Added the activated TT solution to equal volume of the activated Mn PS mixture and vortex.
 4. Incubated the reaction mixture at 20-24° C. overnight.
 5. The reaction mixture was treated with 6 uL 1 M $NaBH_4$ (10-fold molar equivalent to initial aldehyde concentration in the activated PS) for 6 hours.
 6. The solution was buffer-exchanged with saline, 10 mM HEPES, pH 7.5, 1 mM EDTA, 4° C. using a 12-14 KDa molecular weight cut-off membrane.
 7. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot ACWY040228a1

Figure 4:
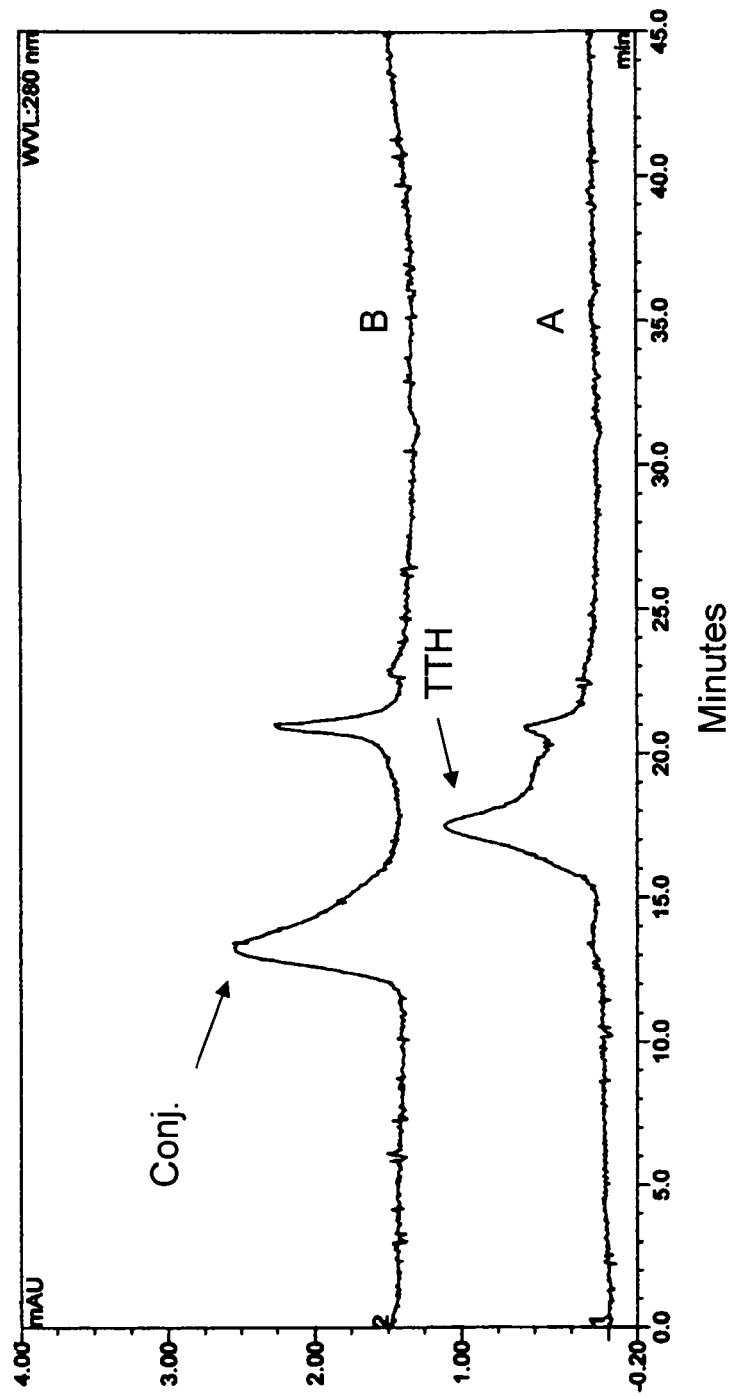
FIG. 4 HPLC profiles (280 nm, by a Waters Ultrahydrogel Linear column) of (A) activated tetanus toxoid (TTH), and (B) combined synthesized multi-valent polysaccharide-tetanus toxoid conjugate (Conj.) prepared by conjugation method A. Upon conjugation to activated polysaccharide mixture, the protein signal shifts from low molecular weight (17.5 minute) to high molecular weight (13.5 minute).
Figure 5:
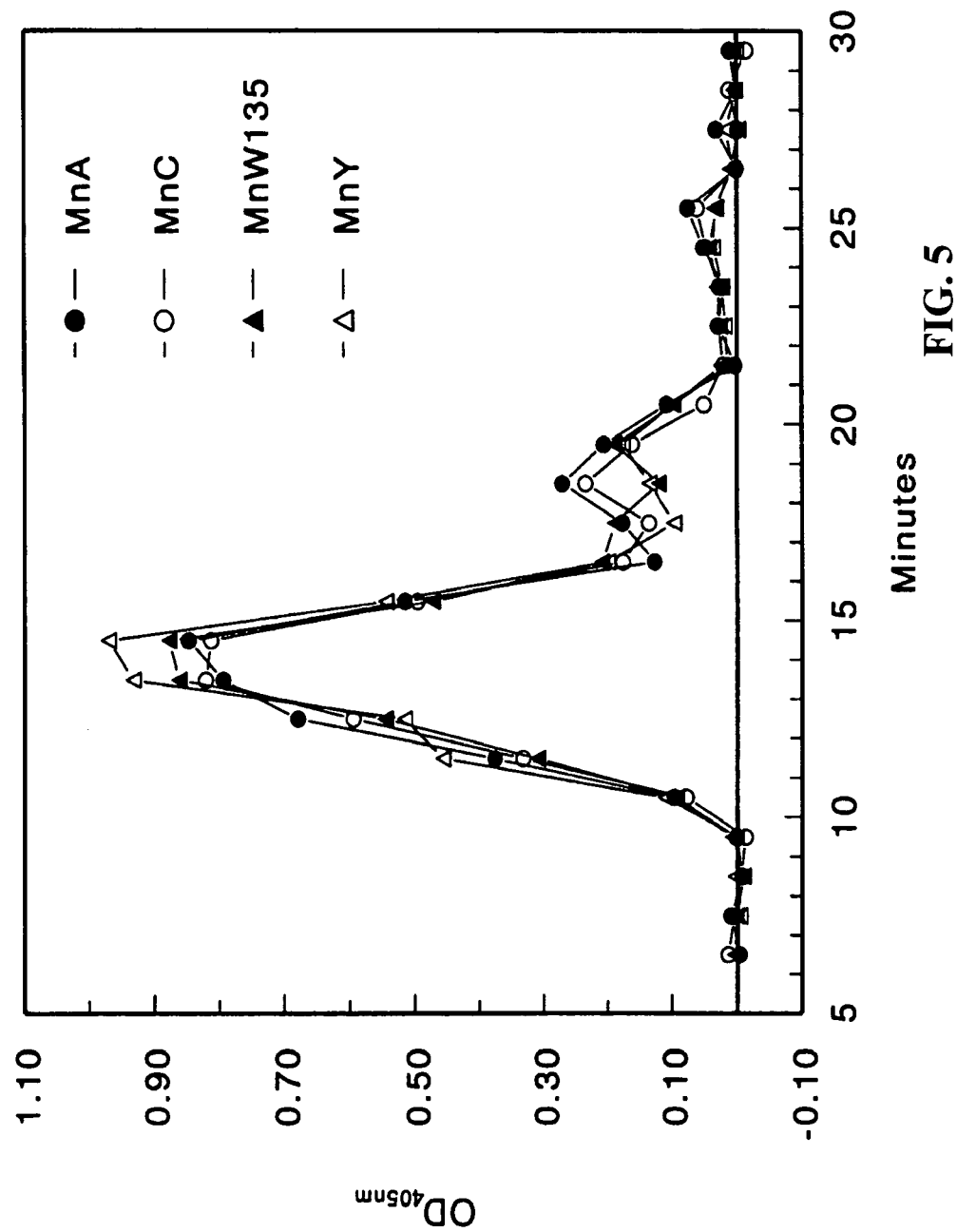
FIG. 5 ELISA detection of conjugated component polysaccharide contained in the combined synthesized multi-valent conjugate vaccine (B) in FIG. 4. Only protein-containing species (i.e. conjugates and free TTH) in the HPLC fractions adhered to the ELISA plate during coating. The conjugated polysaccharides were subsequently detected by antisera specific to each respective PS but not cross-reacting to tetanus toxoid. A major peak was detected at 12-15 minute superimposing the protein signal of (B) in FIG. 4 for all four polysaccharides. MnA is Meningococcal group A, MnC is Meningococcal group C, MnW135 is Meningococcal group W135, and MnY is Meningococcal group Y.

FIG. 4 shows the HPSEC elution profile (monitored at 280 nm) of conjugate lot ACWY040228a1. Shift of the protein signal from 17.5 to 13 minute was observed upon conjugation, and little un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 5).

Immunogenicity of Combined Synthesized Multi-Valent Conjugate Lot ACWY040228a1

The conjugate was used to immunize groups of 10 mice with native polysaccharide as a control at 1 μg polysaccharide/dose on days 0, 14 and 28. The geometric means of the induced antibody levels (units/mL) two weeks post $3^{rd}$ injection determined by ELISA are Mn A, 11 (1, 195; 1 SD confidence interval), MnC, 672 (328, 1379); Mn W135, 72 (32, 162); and Mn Y, 298 (105, 844) for control group and Mn A, 9291 (3535, 24421), Mn C, 4080 (1694, 9824); Mn W135, 17450 (9502, 32050); and Mn Y, 114429 (60462, 216566) for the conjugate batches, assuming 3200 units/mL for the reference serum of each serogroup PS (Table 6). The conjugates induced 6-845 folds more anti-Mn PS specific antibody in mice as compared to the native Mn PS control. The geometric means of the induced bactericidal titer two weeks post $3^{rd}$ injection determined by bactericidal assay are Mn A, 329 (113, 598; 1 SD confidence interval), MnC, 329 (163, 668); Mn W135, 2743 (1851, 4066); and Mn Y, 12958 (10197, 16559) for control group and Mn A, 9699 (3373, 27895), Mn C, 1657 (854, 3214); Mn W135, 6625 (2076, 21143); and Mn Y, 77262 (32824, 181863) for the conjugate batch (Table 6b). The conjugates induced 2.4-29 folds more bactericidal titer in mice as compared to the native Mn PS control.

TABLE 6a

The geometric mean anti-Mn PS antibody levels[a] with 1 SD confidence interval of mouse groups (10 mice per group) two weeks post $3^{rd}$ immunization with 1 μg/dose each of Mn PS in multi-valent conjugate lot ACWY040228a1

| Polysaccharide | Native PS mixture | Lot ACWY040228a1 | Fold increase |
|---|---|---|---|
| A | 11 (1, 195) | 9291 (3535, 24421) | 845 |
| C | 672 (328, 1379) | 4080 (1694, 9824) | 6 |
| W135 | 72 (32, 162) | 17450 (9502, 32050) | 242 |
| Y | 298 (105, 844) | 114429 (60462, 216566) | 384 |

[a]Compared to a reference serum of each PS with an assigned anti-Mn PS antibody level of 3200 units/mL.

TABLE 6b

The geometric mean bactericidal titer with 1 SD confidence interval of mouse groups (10 mice per group) two weeks post 3$^{rd}$ immunization with 1 μg/dose each of Mn PS in multi-valent conjugate lot ACWY040228a1

| Polysaccharide | Native PS mixture | Lot ACWY040228a1 | Fold increase |
|---|---|---|---|
| A | 329 (113, 958) | 9699 (3373, 27895) | 29 |
| C | 329 (163, 668) | 1657 (854, 3214) | 5 |
| W135 | 2743 (1851, 4066) | 6625 (2076, 21143) | 2.4 |
| Y | 12995 (10197, 16559) | 77262 (32824, 181863) | 6 |

Method B—Combined Synthesized Multivalent Meningococcal Groups A, C, W135 and Y Polysaccharides-Tetanus Toxoid Conjugate Lot ACWY040723B5
Activation of TT to Contain Hydrazide Groups
1. Tetanus toxoid (4.2 mg/mL) was activated with 0.42 M hydrazine in the presence of 20 mM EDC, 0.1 M MES, pH 6.5 at 20-24° C.
2. After reacting for 4 hours, the pH of the reaction mixture was raised to 7.5-10 with 1 N NaOH to stop the reaction.
3. The reaction mixture was buffer-exchanged with 30 mM NaCl, 3 mM Na$_2$CO$_3$, pH about 10.5 at 4° C. using a 12-14 KDa dialysis membrane.

Activation of Mn A, C, W135 and Y PS Mixture to Contain Cyanate Groups
1. Mn A, C, W135 and Y PS mixture (0.04 mL, 10 mg/mL, total PS; 2.5 mg/mL, each component PS) was activated with 5 uL CDAP (100 mg/mL in acetonitrile) for 2-2.5 minutes at 20-24° C. in the presence of 5 uL 0.2 M triethylamine.
2. The activated polysaccharide was mixed with 0.625 mL ice-cold 0.2 M HEPES, pH 7.5, 30 mM EDTA, and immediately used for conjugation.

Conjugation of Activated Mn A, C, W135 and Y PS Mixture to Activated TT
1. The activated polysaccharide was added to 0.25 mg activated TT (ice-cold, 0.0.065 mL, 3.84 mg/mL); vortex.
2. Incubated the reaction mixture at 4° C. with gentle shaking for 3 overnights. (The prolonged incubation is to ensure decomposition of the residual left over unreacted cyanate groups.)
3. The solution was buffer-exchanged with saline, 10 mM HEPES, pH 7.5, 1 mM EDTA using a 12-14 KDa molecular weight cut-off membrane.
4. Volume of the dialyzed conjugate was determined, and the concentrations of the protein (TT) and each polysaccharide (Mn A, C, W135 and Y) were calculated from the input masses.

Figure 6:
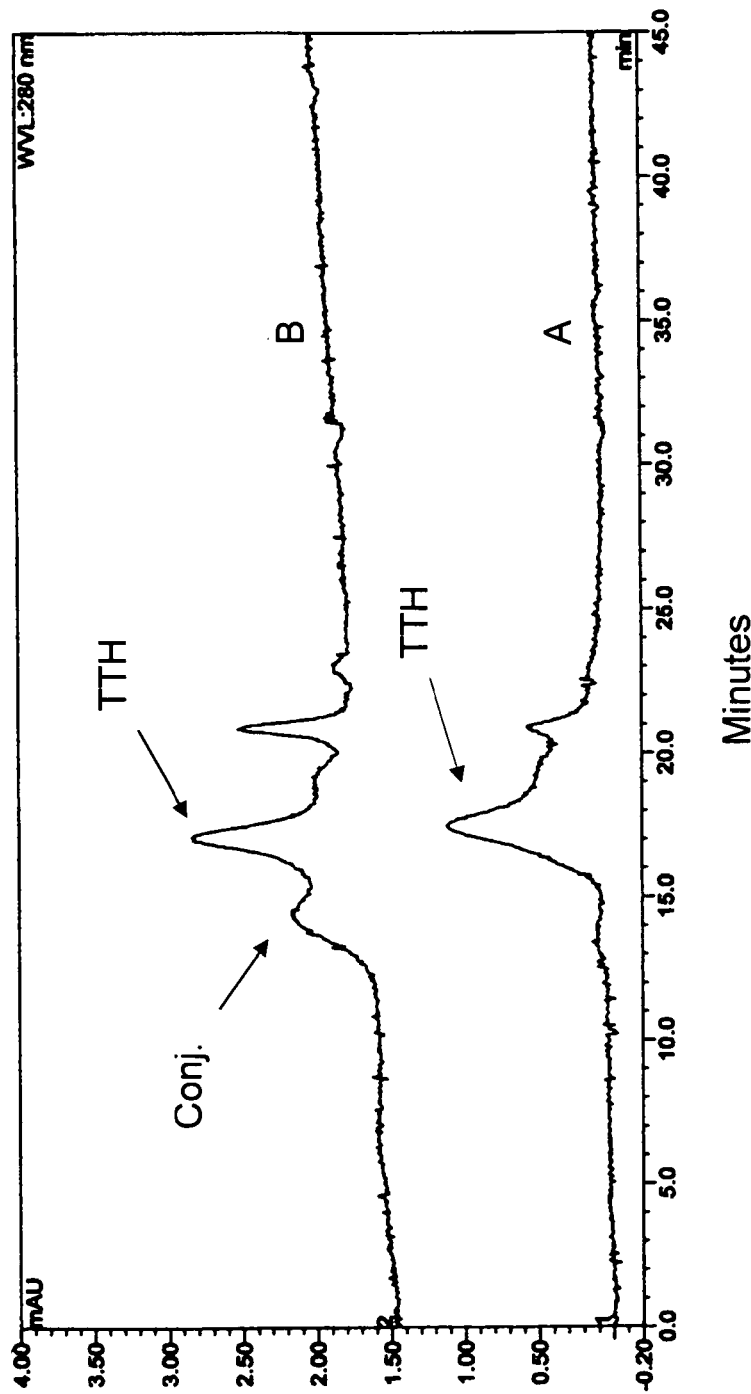
FIG. 6 HPLC profiles (280 nm, by a Waters Ultrahydrogel Linear column) of (A) activated tetanus toxoid (TTH), and (B) combined synthesized multi-valent polysaccharide-tetanus toxoid conjugate (Conj.) prepared by conjugation method B. Upon conjugation to activated polysaccharide mixture, the protein signal shifts from low molecular weight (17.5 minute) to high molecular weight (13.5 minute). There was some free unconjugated TTH left in the product mixture.
Figure 7:
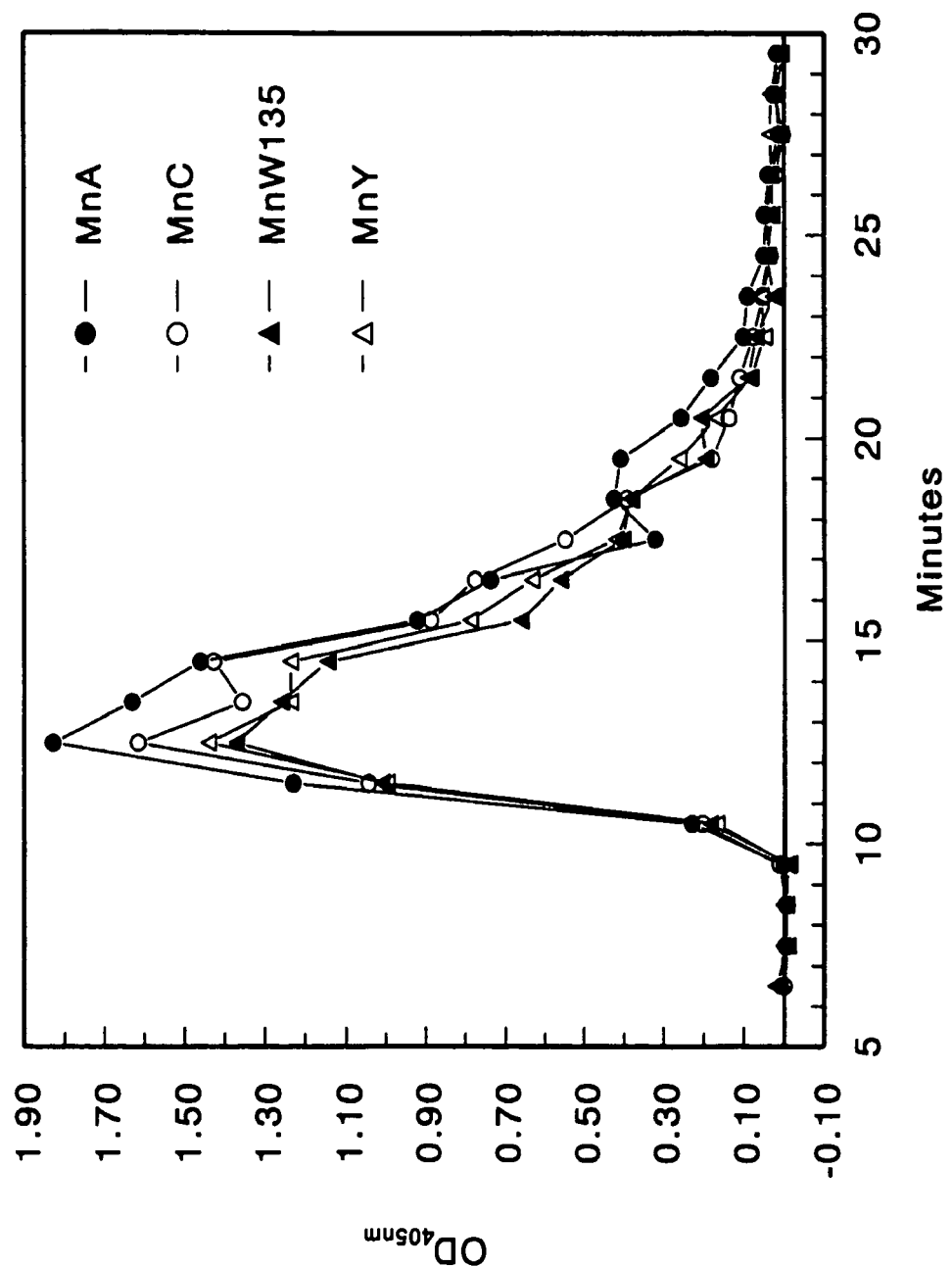
FIG. 7 ELISA detection of conjugated component polysaccharide in the combined synthesized multi-valent conjugate vaccine of (B) in FIG. 6. Only protein-containing species (i.e. conjugates and free TTH) of the HPLC fractions adhered to the ELISA plate during coating, and the conjugated polysaccharides were subsequently detected by antisera specific to each respective PS but not cross-reacting to tetanus toxoid. A major peak was detected at 12-15 minute superimposing the protein signal of (B) in FIG. 6 for all four polysaccharides. MnA is Meningococcal group A, MnC is Meningococcal group C, MnW135 is Meningococcal group W135, and MnY is Meningococcal group Y.

Characterization of Combined Synthesized Multi-Valent Conjugate Lot ACWY040723B5
FIG. 6 shows the HPSEC elution profiles (monitored at 280 nm) of conjugate lot ACWY040723B5. Shift of the protein signal from 17.5 to 14.5 minute was observed upon conjugation, and significant un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 7).

Immunogenicity of Combined Synthesized Multi-Valent Conjugate Lot ACWY040423B5
The conjugate was used to immunize groups of 10 mice with native polysaccharide as a control at 1 μg polysaccharide/dose on days 0, 14 and 28. The geometric means of the induced antibody levels (units/mL) two weeks post 3$^{rd}$ injection determined by ELISA are Mn A, 11 (1, 195; 1 SD confidence interval), MnC, 672 (328, 1379); Mn W135, 72 (32, 162); and Mn Y, 298 (105, 844) for control group and Mn A, 5214 (2532, 10739), Mn C, 6430 (1797, 23008); Mn W135, 8211 (490, 137609); and Mn Y, 81833 (26489, 252808) for the conjugate batches, assuming 3200 units/mL for the reference serum of each serogroup PS (Table 7). The conjugates induced 10-474 folds more anti-Mn PS specific antibody in mice as compared to the native Mn PS control. The geometric means of the induced bactericidal titer two weeks post 3$^{rd}$ injection determined by bactericidal assay are Mn A, 329 (113, 598; 1 SD confidence interval), MnC, 329 (163, 668); Mn W135, 2743 (1851, 4066); and Mn Y, 12958 (10197, 16559) for control group and Mn A, 1255 (696, 2263), Mn C, 3203 (1536, 6679); Mn W135, 33774 (9346, 122041); and Mn Y, 171471 (93450, 314632) for the conjugate batch (Table 7b). The conjugates induced 4-13 folds more bactericidal titer in mice as compared to the native Mn PS control.

TABLE 7a

The geometric mean anti-Mn PS antibody levels[a] with 1 SD confidence interval of mouse groups (10 mice per group) two weeks post 3$^{rd}$ immunization with 1 μg/dose each of Mn PS in multi-valent conjugate lot ACWY040723B5

| Polysaccharide | Native PS mixture | Lot ACWY040723B5 | Fold increase |
|---|---|---|---|
| A | 11 (1, 195) | 5214 (2532, 10739) | 474 |
| C | 672 (328, 1379) | 6430 (1797, 23008) | 10 |
| W135 | 72 (32, 162) | 8211 (490, 137609) | 114 |
| Y | 298 (105, 844) | 81833 (26489, 252808) | 275 |

[a]Compared to a reference serum of each PS with an assigned anti-Mn PS antibody level of 3200 units/mL.

TABLE 7b

The geometric mean bactericidal titer with 1 SD confidence interval of mouse groups (10 mice per group) two weeks post 3$^{rd}$ immunization with 1 μg/dose each of Mn PS in multi-valent conjugate lot ACWY040723B5

| Polysaccharide | Native PS mixture | Lot ACWY040723B5 | Fold increase |
|---|---|---|---|
| A | 329 (113, 958) | 1255 (696, 2263) | 4 |
| C | 329 (163, 668) | 3203 (1536, 6679) | 10 |
| W135 | 2743 (1851, 4066) | 33774 (9346, 122041) | 12 |
| Y | 12995 (10197, 16559) | 171471 (93450, 314632) | 13 |

Method C—Combined Synthesized Multivalent Meningococcal Groups A, C, W135 and Y Polysaccharides-Tetanus Toxoid Conjugate Lot ACWY040723C5
Activation of TT to Contain Aldehyde Groups
1. Tetanus toxoid (4.2 mg/mL) was activated with 0.42 M 1-amino-2,3-propanediol (APDO) in the presence of 20 mM EDC, 0.1 M MES, pH 6.5 at 20-24° C.
2. After reacting for 4 hours, the pH of the reaction mixture was raised to 7.5-10 with 1 N NaOH to stop the reaction.
3. The reaction mixture was buffer-exchanged with 30 mM NaCl, 3 mM Na$_2$CO$_3$, pH about 10.5 at 4° C. using a 12-14 KDa dialysis membrane.
4. The degree of TT modification with APDO was determined by purpald assay [31] and Lowry assay [26].
5. Aliquot of TT-APDO was reacted with 6 mM NaIO$_4$ for 3 hour and then buffer exchanged with 30 mM NaCl, 3 mM Na$_2$CO$_3$, pH about 10.5.

Activation of Mn A, C, W135 and Y PS Mixture to Contain Hydrazide Groups
1. Mn A, C, W135 and Y PS mixture (0.04 mL, 10 mg/mL, total PS; 2.5 mg/mL, each component PS) was activated with 5 uL CDAP (100 mg/mL in acetonitrile) for 2-2.5 minutes at 20-24° C. in the presence of 5 uL 0.2 M triethylamine.
2. At the end of activation, 0.01 mL 5 M hydrazine, pH 7 was added and mixed.
3. The reaction mixture was incubated 4 hours at 20-24° C.
4. The sample was dialyzed against 10 mM HEPES, pH 7.5 at 4° C. using a 12-14 KDa dialysis membrane.
5. The volume of the activated PS mixture was determined (0.12 mL).

Conjugation of Activated Mn A, C, W135 and Y PS Mixture to Activated TT
1. Hydrazide-containing Mn A, C, W135 and Y PS mixture (0.5 mg in 0.12 mL) was mixed with 0.03 mL 1 M HEPES, pH 7.5.
2. Aliquot of aldehyde-containing TT (0.5 mg; 0.148 mL 3.38 mg/mL) was added to the activated Mn A, C, W135 and Y PS mixture. (Total volume, 0.298 mL)
3. Incubate the reaction mixture at 20-24° C. for 18 hours.
4. The reaction mixture was treated with 5 uL 1 M NaBH$_4$ for 6 hours.
5. The solution was buffer-exchanged with saline, 10 mM HEPES, pH 7.5, 1 mM EDTA using a 12-14 KDa molecular weight cut-off membrane.
6. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot ACWY040723C5

Figure 8:
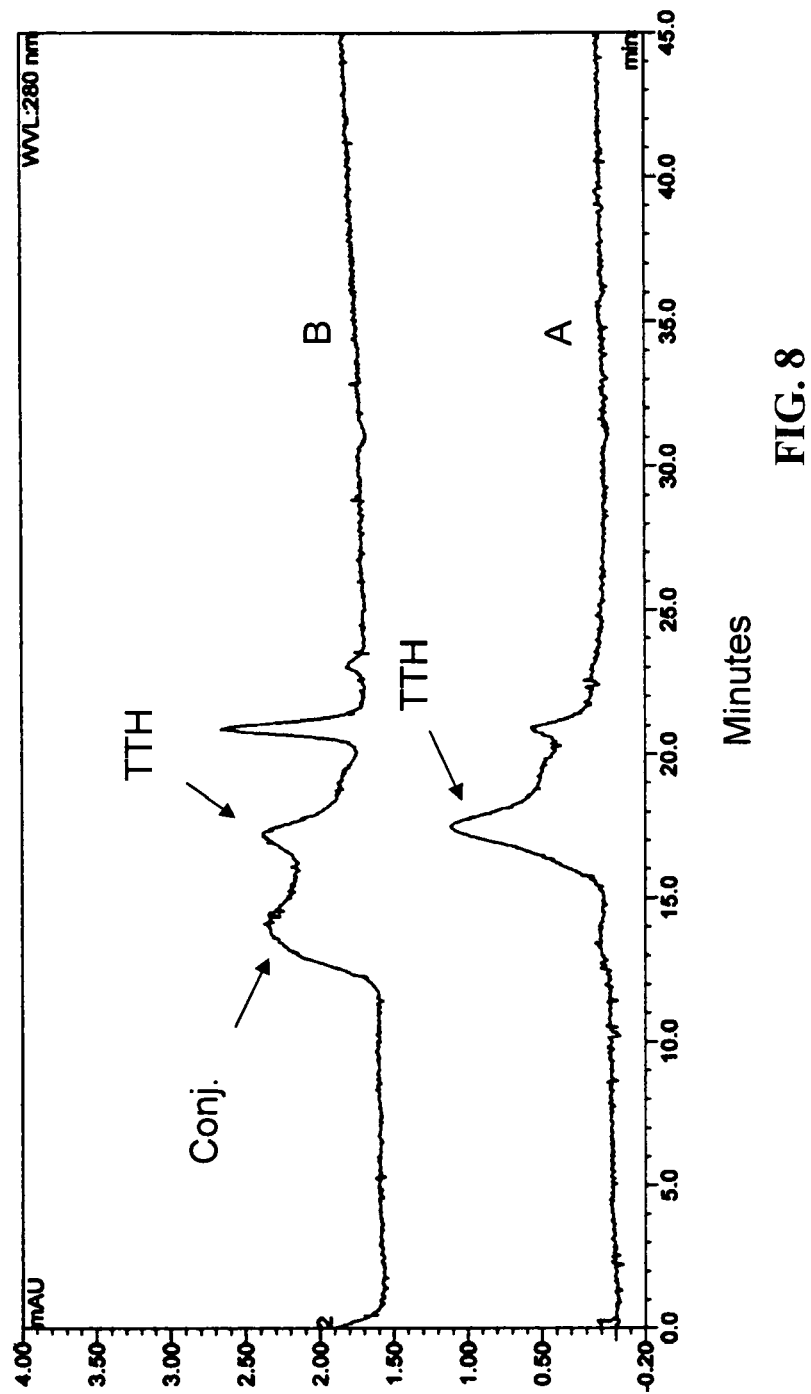
FIG. 8 HPLC profiles (280 nm, by a Waters Ultrahydrogel Linear column) of (A) activated tetanus toxoid (TTH), and (B) combined synthesized multi-valent polysaccharide-tetanus toxoid conjugate (Conj.) prepared by conjugation method C. Upon conjugation to activated polysaccharide mixture, the protein signal shifts from low molecular weight (17.5 minute) to high molecular weight (13.5 minute). There was some free unconjugated TTH left in the product mixture.
Figure 9:
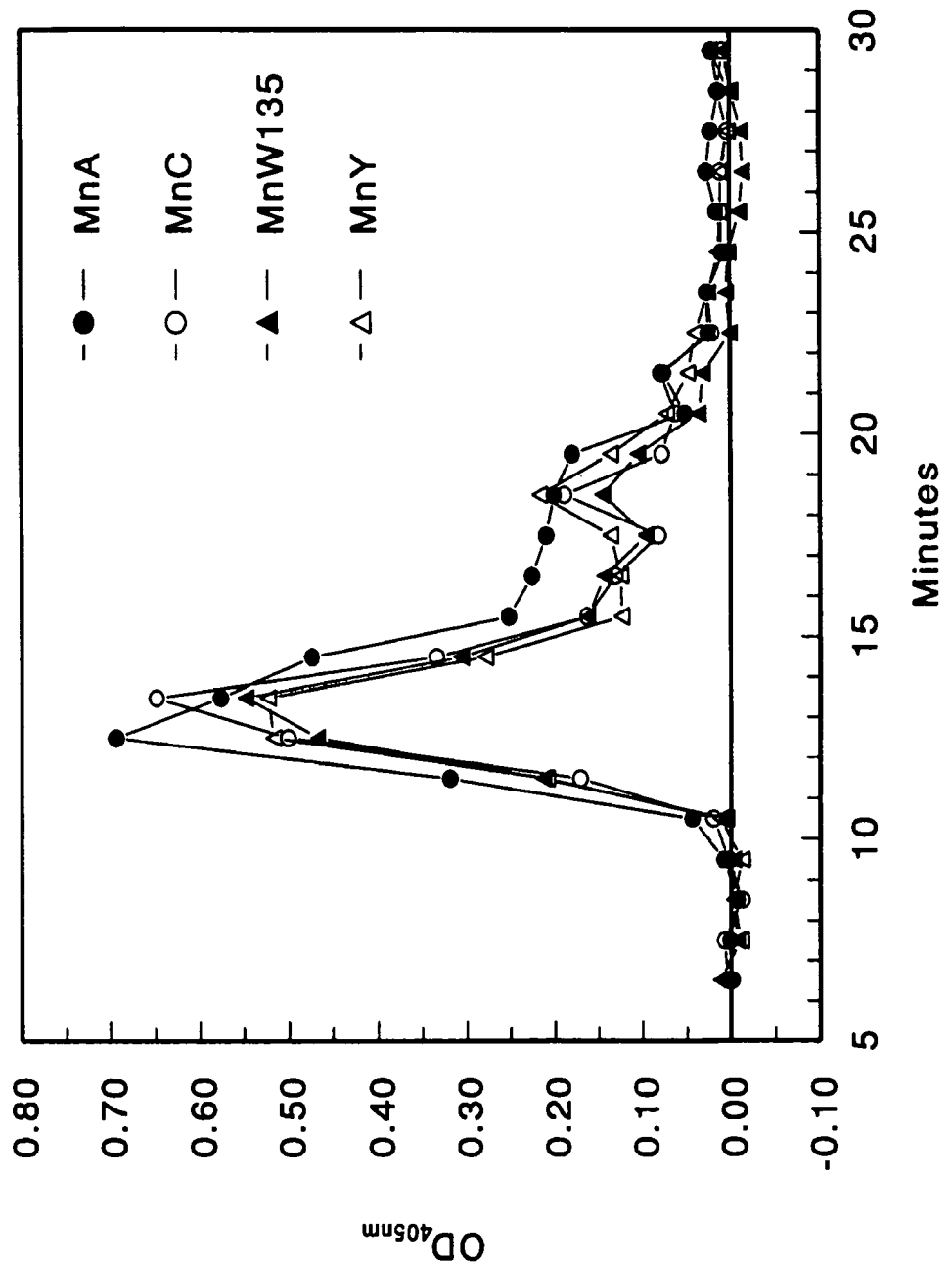
FIG. 9 ELISA detection of conjugated component polysaccharide in the combined synthesized multi-valent conjugate vaccine of (B) in FIG. 8. Only protein-containing species (i.e. conjugates and free TTH) of the HPLC fractions adhered to the ELISA plate during coating, and the conjugated polysaccharides were subsequently detected by antisera specific to each respective PS but not cross-reacting to tetanus toxoid. A major peak was detected at 12-15 minute superimposing the protein signal of (B) in FIG. 8 for all four polysaccharides. MnA is Meningococcal group A, MnC is Meningococcal group C, MnW135 is Meningococcal group W135, and MnY is Meningococcal group Y.

FIG. 8 shows the HPSEC elution profiles (monitored at 280 nm) of conjugate lot ACWY040723C5. Shift of the protein signal from 17.5 to 14 minute was observed upon conjugation, and residual un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 9).

Immunogenicity of Combined Synthesized Multi-Valent Conjugate Lot ACWY040423C5

The conjugate was used to immunize groups of 10 mice with native polysaccharide as a control at 1 μg polysaccharide/dose on days 0, 14 and 28. The geometric means of the induced antibody levels (units/mL) two weeks post 3$^{rd}$ injection determined by ELISA are Mn A, 11 (1, 195; 1 SD confidence interval), MnC, 672 (328, 1379); Mn W135, 72 (32, 162); and Mn Y, 298 (105, 844) for control group and Mn A, 17250 (6786, 43847), Mn C, 11035 (5996, 20309); Mn W135, 8321 (3505, 19755); and Mn Y, 84643 (46669, 153517) for the conjugate batches, assuming 3200 units/mL for the reference serum of each serogroup PS (Table 8). The conjugates induced 16-1568 folds more anti-Mn PS specific antibody in mice as compared to the native Mn PS control. The geometric means of the induced bactericidal titer two weeks post 3$^{rd}$ injection determined by bactericidal assay are Mn A, 329 (113, 598; 1 SD confidence interval), MnC, 329 (163, 668); Mn W135, 2743 (1851, 4066); and Mn Y, 12958 (10197, 16559) for control group and Mn A, 3941 (921, 16862), Mn C, 6860 (2812, 16733); Mn W135, 72403 (39288, 133431); and Mn Y, 82832 (43591, 157400) for the conjugate batch (Table 8b). The conjugates induced 6-26 folds more bactericidal titer in mice as compared to the native Mn PS control.

TABLE 8a

The geometric mean anti-Mn PS antibody levels[a] with 1 SD confidence interval of mouse groups (10 mice per group) two weeks post 3$^{rd}$ immunization with 1 μg/dose each of Mn PS in multi-valent conjugate lot ACWY040723C5

| Polysaccharide | Native PS mixture | Lot ACWY040723C5 | Fold increase |
|---|---|---|---|
| A | 11 (1, 195) | 17250 (6786, 43847) | 1568 |
| C | 672 (328, 1379) | 11035 (5996, 20309) | 16 |
| W135 | 72 (32, 162) | 8321 (3505, 19755) | 116 |
| Y | 298 (105, 844) | 84643 (46669, 153517) | 284 |

[a]Compared to a reference serum of each PS with an assigned anti-Mn PS antibody level of 3200 units/mL.

TABLE 8b

The geometric mean bactericidal titer with 1 SD confidence interval of mouse groups (10 mice per group) two weeks post 3$^{rd}$ immunization with 1 μg/dose each of Mn PS in multi-valent conjugate lot ACWY040723C5

| Polysaccharide | Native PS mixture | Lot ACWY040723C5 | Fold increase |
|---|---|---|---|
| A | 329 (113, 958) | 3941 (921, 16862) | 12 |
| C | 329 (163, 668) | 6860 (2812, 16733) | 21 |
| W135 | 2743 (1851, 4066) | 72403 (39288, 133431) | 26 |
| Y | 12995 (10197, 16559) | 82832 (43591, 157400) | 6 |

Method A—Combined Synthesized Multivalent Meningococcal Groups A, C, W135 and Y Polysaccharides-Tetanus Toxoid Conjugate Lot MnACWYTTD(K72)050131A6

Activation of TT to Contain Hydrazide Groups
1. Tetanus toxoid (4.2 mg/mL) was activated with 0.36 M adipic acid dihydrazide in the presence of 72 mM lysine, 12 mM EDC, 0.1 M MES, pH 5.5 at 20-24° C.
2. After reacting for 2 hours, the reaction mixture was buffer-exchanged with 30 mM NaCl, 10 mM HEPES, pH about 7.5 at 4° C. using a 12-14 KDa dialysis membrane.
3. The volume of the sample was determined, and the concentration of the activated TT was calculated (3.48 mg/mL).

Activation of Mn A, C, W135 and Y PS Mixture to Contain Aldehyde Groups
1. Mn A, C, W135 and Y PS mixture (10 mg/mL, total PS; 2.5 mg/mL, each component PS) was reacted with 6 mM NaIO$_4$ at 4° C. overnight.
2. The sample was dialyzed against 10 mM HEPES, pH 7.5 at 4° C. using a 12-14 KDa dialysis membrane.
3. The volume of the sample was determined, and the concentration of the activated PS mixture was calculated (7.25 mg/mL total PS).

Conjugation of Activated Mn A, C, W135 and Y PS Mixture to Activated TT
1. Aliquot of aldehyde-containing Mn A, C, W135 and Y PS mixture (1 mg; 0.138 mL, 7.25 mg/mL) was added with 0.0284 mL 1 M HEPES, pH 7.5 and 0.0189 mL 0.5 M EDTA.
2. The mixture was kept on ice.
3. Aliquot of hydrazide-containing TT (1 mg; 0.288 mL, 3.475 mg/mL) was added to the activated PS mixture on ice and mixed.
4. Incubated the reaction mixture at 4° C. overnight.
5. The reaction mixture was treated with 10 uL 1 M NaBH$_4$ for 6 hours.

6. The solution was buffer-exchanged with saline, 10 mM HEPES, pH 7.5, 1 mM EDTA, 4° C. using a 12-14 KDa molecular weight cut-off membrane.
7. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot MnACWYTTD(K72)050131A6

Figure 10:
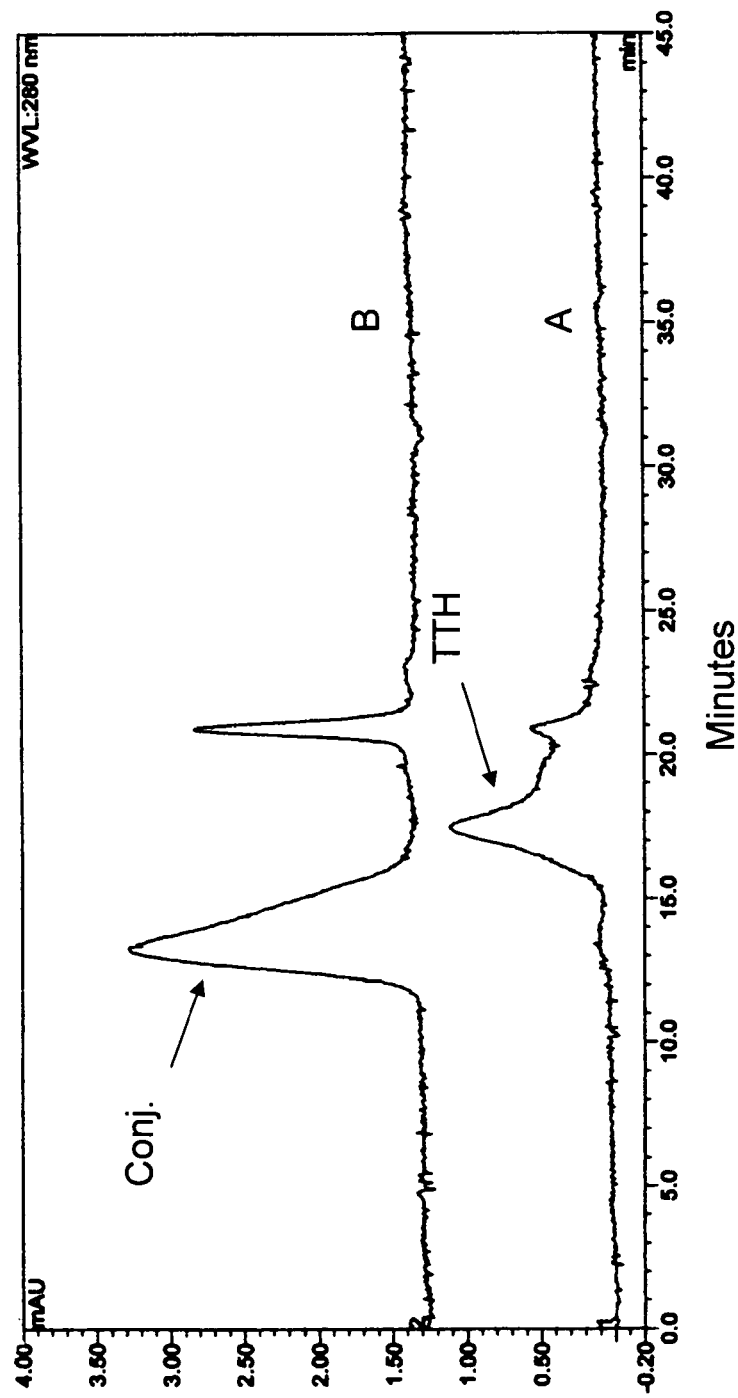
FIG. 10 HPLC profiles (280 nm, by a Waters Ultrahydrogel Linear column) of (A) activated tetanus toxoid (TTH), and (B) combined synthesized multi-valent polysaccharide-tetanus toxoid conjugate (Conj.) prepared by conjugation method A. Upon conjugation to activated polysaccharide mixture, the protein signal shifts from low molecular weight (17.5 minute) to high molecular weight (13.5 minute).
Figure 11:
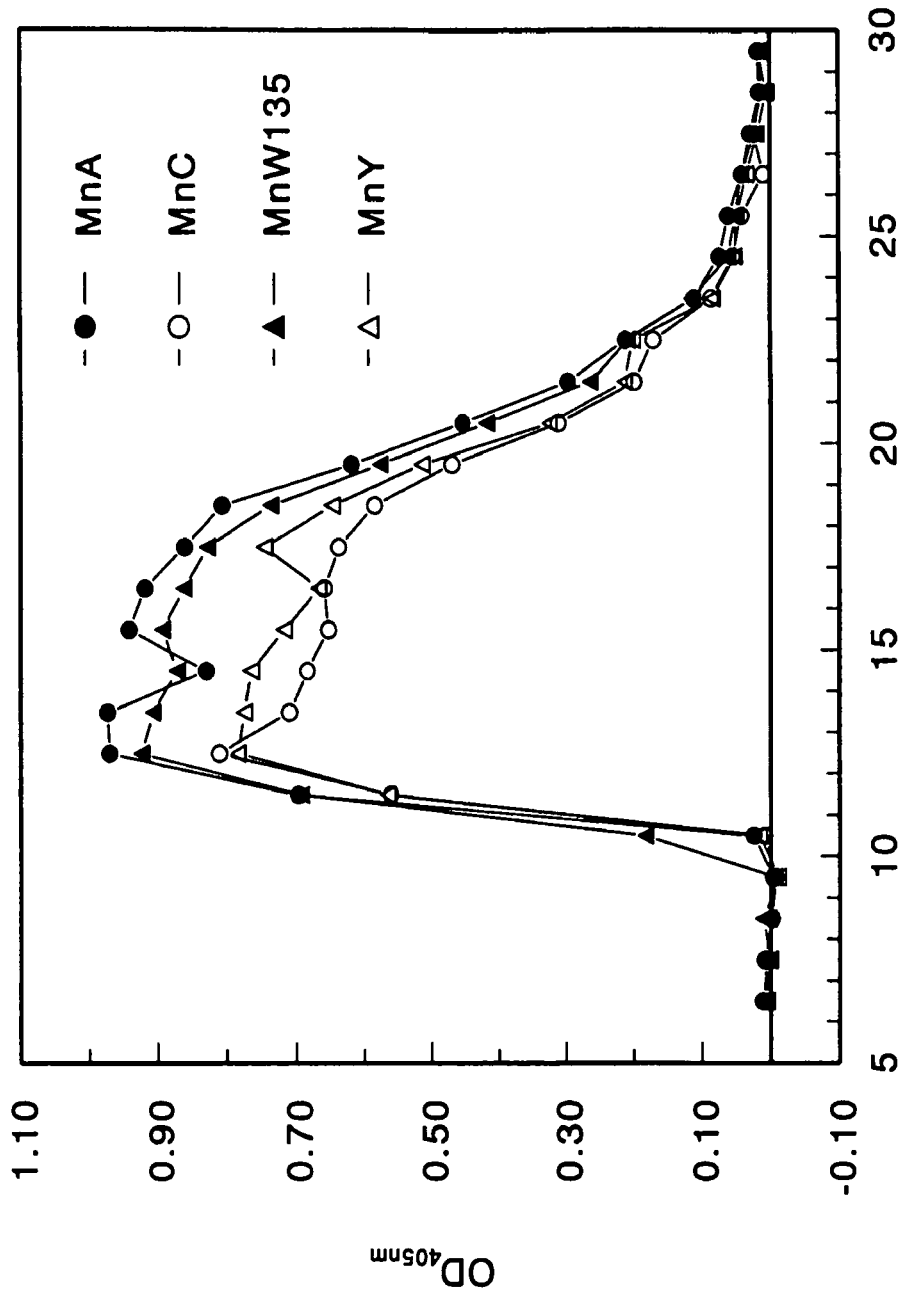
FIG. 11 ELISA detection of conjugated component polysaccharide in the combined synthesized multi-valent conjugate vaccine of (B) in FIG. 10. Only protein-containing species (i.e. conjugates and free TTH) of the HPLC fractions adhered to the ELISA plate during coating, and the conjugated polysaccharides were subsequently detected by antisera specific to each respective PS but not cross-reacting to tetanus toxoid. High ELISA signal was detected at 12-19 minute for all four polysaccharides. The high ELISA signal at 12-15 minute superimposed the protein signal of (B) in FIG. 10, while the high ELISA signal at 15-19 minute was due to residual conjugates of small molecular weight. MnA is Meningococcal group A, MnC is Meningococcal group C, MnW135 is Meningococcal group W135, and MnY is Meningococcal group Y.

FIG. 10 shows the HPSEC elution profile (monitored at 280 nm) of conjugate lot MnACWYTTD(K72)050131A6. Shift of the protein signal from 17.5 to 13 minute was observed upon conjugation, and little un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 11).

Immunogenicity of Combined Synthesized Multi-Valent Conjugate Lot MnACWYTTD(K72)050131A6

The conjugate was used to immunize a group of 5 mice with native polysaccharide mixture (10 mice) as a control at 1 µg each polysaccharide/dose on days 0, 14 and 28. The geometric means of the induced antibody levels (units/mL) two weeks post $3^{rd}$ injection determined by ELISA are Mn A, 11 (1, 195; 1 SD confidence interval); MnC, 672 (328, 1379); Mn W135, 72 (32, 162); and Mn Y, 298 (105, 844) for control group and Mn A, 8308 (5282, 13071); Mn C, 4090 (1424, 11746); Mn W135, 11314 (5981, 21403); and Mn Y, 90779 (63135, 130528) for the conjugate, assuming 3200 units/mL for the reference serum of each PS (Table 9). The conjugates induced 6-305 folds more anti-Mn PS specific antibody in mice as compared to the native Mn PS control.

TABLE 9

The geometric mean anti-Mn PS antibody levels$^a$ with 1 SD confidence interval of mouse groups (10 mice for native PS mixture control and 5 mice for experiment) two weeks post $3^{rd}$ immunization with 1 µg/dose each of Mn PS in multi-valent conjugate lot MnACWYTTD(K72)050131A6.

| Polysaccharide | Native PS mixture | Lot MnACWYTTD(K72)050131A6 | Fold increase |
|---|---|---|---|
| A | 11 (1, 195) | 8308 (5282, 13071) | 755 |
| C | 672 (328, 1379) | 4090 (1424, 11746) | 6 |
| W135 | 72 (32, 162) | 11314 (5981, 21403) | 157 |
| Y | 298 (105, 844) | 90779 (63135, 130528) | 305 |

$^a$Compared to a reference serum of each PS with an assigned anti-Mn PS antibody level of 3200 units/mL.

Method B—Combined Synthesized Multivalent Meningococcal Groups A, C, W135 and Y Polysaccharides-Tetanus Toxoid Conjugate Lot MnACWYTTD(K72)050201B6

Activation of TT to Contain Hydrazide Groups
1. Tetanus toxoid (4.2 mg/mL) was activated with 0.36 M adipic acid dihydrazide in the presence of 72 mM lysine, 12 mM EDC, 0.1 M MES, pH 5.5 at 20-24° C.
2. After reacting for 2 hours, the reaction mixture was buffer-exchanged with 30 mM NaCl, 10 mM HEPES, pH about 7.5 at 4° C. using a 12-14 KDa dialysis membrane.
3. The volume of the sample was determined, and the concentration of the activated TT was calculated (3.48 mg/mL).

Activation of Mn A, C, W135 and Y PS Mixture to Contain Cyanate Groups
1. Mn A, C, W135 and Y PS mixture (0.1 mL, 10 mg/mL, total PS; 2.5 mg/mL, each component PS) was activated with 6 uL CDAP (100 mg/mL in acetonitrile) for 2-2.5 minutes at 20-24° C. in the presence of 6 uL 0.2 M triethylamine.
2. The activated polysaccharide was mixed with 1.25 mL ice-cold 0.2 M HEPES, pH 7.5, 30 mM EDTA, and immediately used for conjugation.

Conjugation of Activated Mn A, C, W135 and Y PS Mixture to Activated TT
1. The activated polysaccharide was added to 0.5 mg activated TT (ice-cold, 0.144 mL, 3.48 mg/mL); vortex.
2. Incubated the reaction mixture at 4° C. with gentle shaking for 3 overnights. (The prolonged incubation is to ensure decomposition of the residual left over unreacted cyanate groups.)
3. The solution was buffer-exchanged with saline, 10 mM HEPES, pH 7.5, 1 mM EDTA using a 12-14 KDa molecular weight cut-off membrane.
4. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot MnACWYTTD(K72)050201B6

Figure 12:
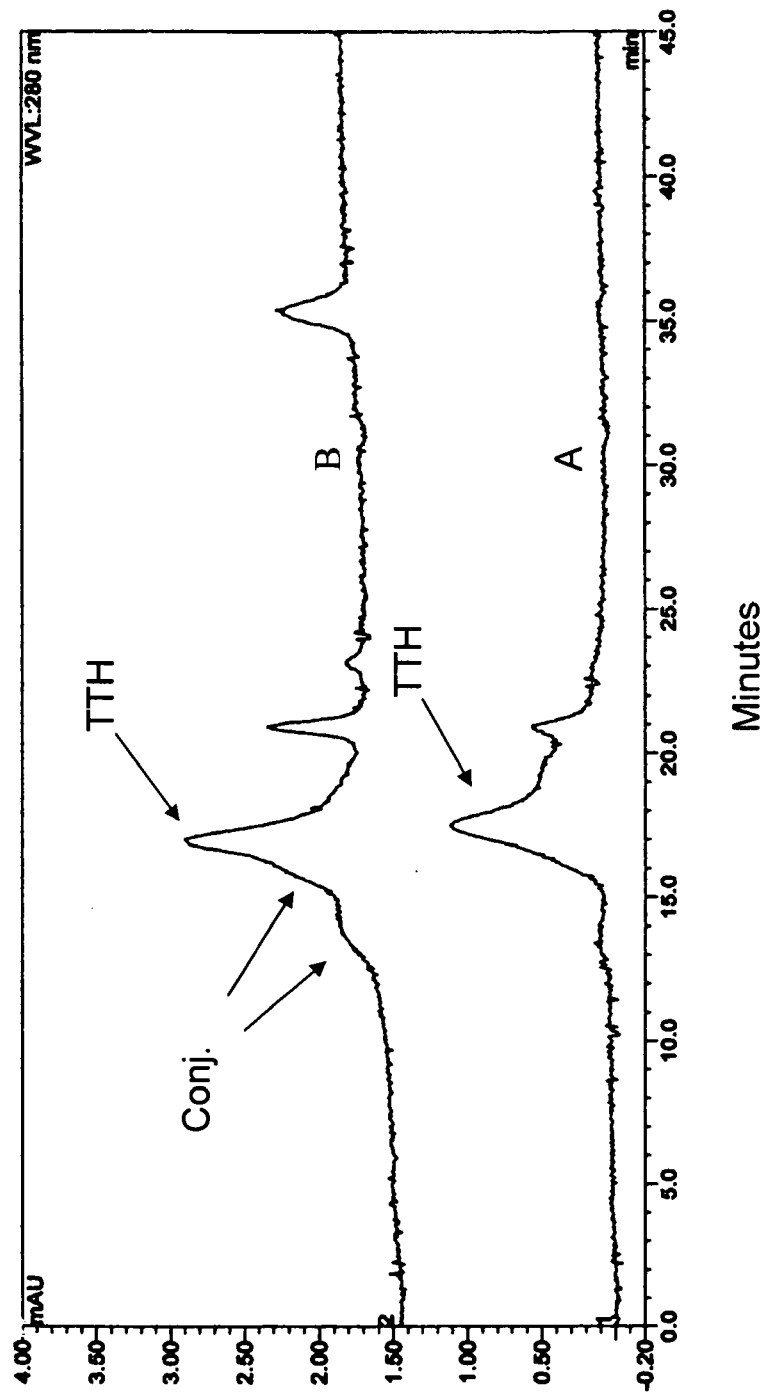
FIG. 12 HPLC profiles (280 nm, by a Waters Ultrahydrogel Linear column) of (A) activated tetanus toxoid (TTH), and (B) combined synthesized multi-valent polysaccharide-tetanus toxoid conjugate (Conj.) prepared by conjugation method B. Upon conjugation to activated polysaccharide mixture, the protein signal shifts from low molecular weight (17.5 minute) to high molecular weight (13.5 minute). There was substantial free unconjugated TTH left in the product mixture.
Figure 13:
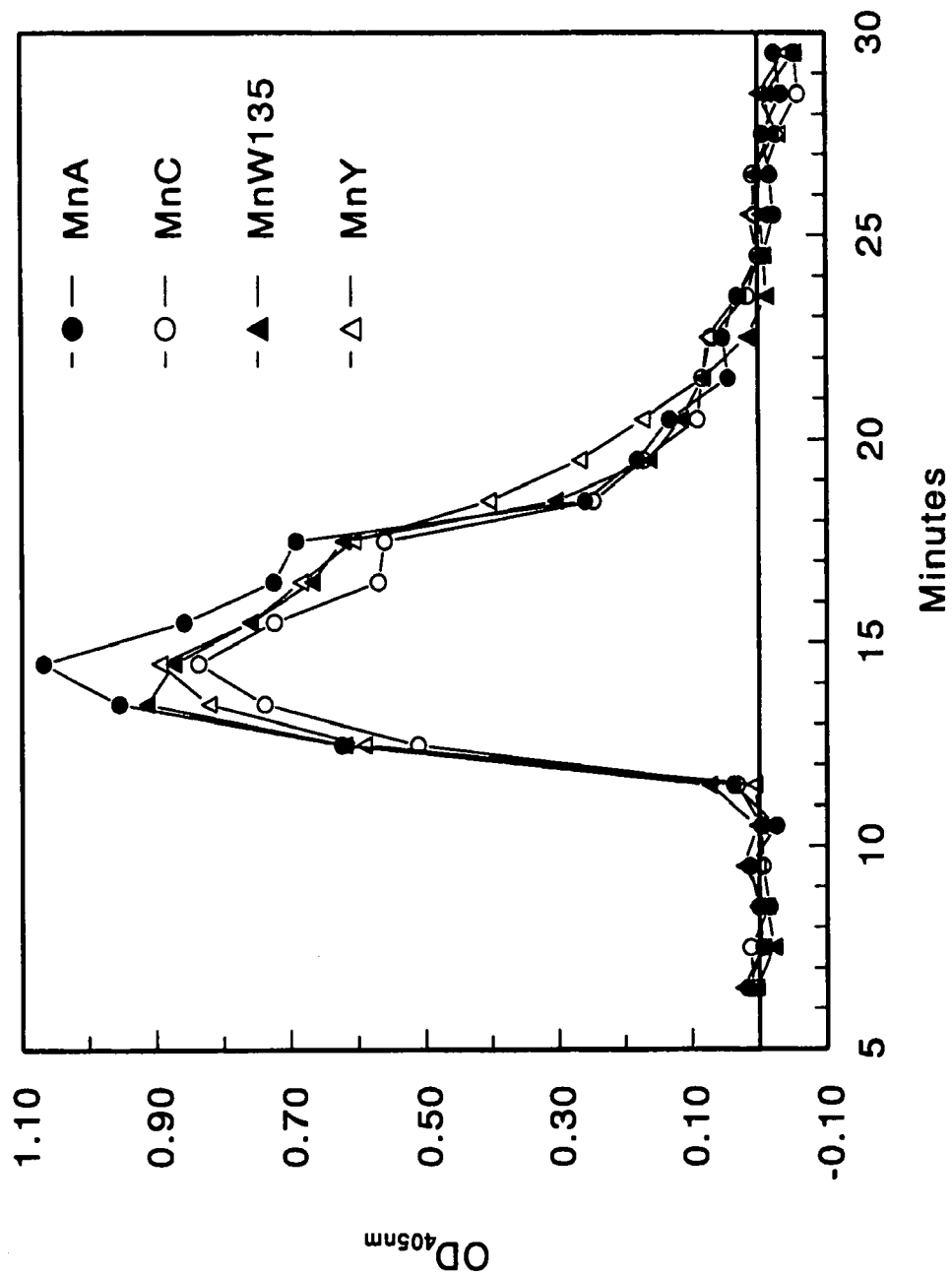
FIG. 13 ELISA detection of conjugated component polysaccharide in the combined synthesized multi-valent conjugate vaccine of (B) in FIG. 12. Only protein-containing species (i.e. conjugates and free TTH) of the HPLC fractions adhered to the ELISA plate during coating, and the conjugated polysaccharides were subsequently detected by antisera specific to each respective PS but not cross-reacting to tetanus toxoid. High ELISA signal was detected at 12-18 minute for all four polysaccharides. The high ELISA signal at 12-15 minute superimposed the protein signal of (B) in FIG. 12, while the high ELISA signal at 15-18 minute was due to residual conjugates of small molecular weight. MnA is Meningococcal group A, MnC is Meningococcal group C, MnW135 is Meningococcal group W135, and MnY is Meningococcal group Y.

FIG. 12 shows the HPSEC elution profiles (monitored at 280 nm) of conjugate lot MnACWYTTD(K72)050201B6. Shift of the protein signal from 17.5 to 14 and 16 minute was observed upon conjugation, and substantial amount of un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 13).

Immunogenicity of Combined Synthesized Multi-Valent Conjugate Lot MnACWYTTD(K72)050201B6

The conjugate was used to immunize a group of 5 mice with native polysaccharide as a control (10 mice) at 1 µg each polysaccharide/dose on days 0, 14 and 28. The geometric means of the induced antibody levels (units/mL) two weeks post $3^{rd}$ injection determined by ELISA are Mn A, 11 (1, 195; 1 SD confidence interval); MnC, 672 (328, 1379); Mn W135, 72 (32, 162); and Mn Y, 298 (105, 844) for the control and Mn A, 2752 (1355, 5589); Mn C, 2930 (1190, 7212); Mn W135, 4755 (1455, 15542); and Mn Y, 22494 (10466, 48347) for the conjugate group, assuming 3200 units/mL for the reference serum of each PS (Table 10). The conjugates induced 4-250 folds more anti-Mn PS specific antibody in mice as compared to the native Mn PS control.

TABLE 10

The geometric mean anti-Mn PS antibody levels$^a$ with 1 SD confidence interval of mouse groups (10 mice for native PS mixture control and 5 mice for experiment) two weeks post $3^{rd}$ immunization with 1 µg/dose each of Mn PS in multi-valent conjugate lot MnACWYTTD(K72)050201B6.

| Polysaccharide | Native PS mixture | Lot MnACWYTTD(K72)050201B6 | Fold increase |
|---|---|---|---|
| A | 11 (1, 195) | 2752 (1355, 5589) | 250 |
| C | 672 (328, 1379) | 2930 (1190, 7212) | 4 |
| W135 | 72 (32, 162) | 4755 (1455, 15542) | 66 |
| Y | 298 (105, 844) | 22494 (10466, 48347) | 75 |

$^a$Compared to a reference serum of each PS with an assigned anti-Mn PS antibody level of 3200 units/mL.

Method A—Combined Synthesized Multivalent Meningococcal Groups A, C, W135 and Y Polysaccharides-Tetanus Toxoid Conjugate Lot TTHACWY061126

Activation of TT to Contain Hydrazide Groups
1. Tetanus toxoid (4.2 mg/mL) was activated with 0.42 M hydrazine in the presence of 20 mM EDC, 0.1 M MES, pH 5.5 at 20-24° C.
2. After reacting for 4 hours, the pH of the reaction mixture was raised to 7.5-10 with 1 N NaOH to stop the reaction.
3. The reaction mixture was buffer-exchanged with 30 mM NaCl, 3 mM $Na_2CO_3$, pH about 10.5 at 4° C. using a 12-14 KDa dialysis membrane.

Activation of Individual Mn A, C, W135 and Y PS by $NaIO_4$ to Contain Aldehyde Groups
1. Mn A PS (10 mg/mL) was activated with 15 mM $NaIO_4$ at 4° C. for 72 hrs, quenched with 25 mM glycerol and dialyzed against $H_2O$ at 4° C.
2. Mn C PS (10 mg/mL) was activated with 6 mM $NaIO_4$ at room temperature for 4 hrs, quenched with 25 mM glycerol and dialyzed against $H_2O$ at 4° C.
3. Mn W135 PS (10 mg/mL) was activated with 3 mM $NaIO_4$ at 4° C. overnight, quenched with 25 mM glycerol and dialyzed against $H_2O$ at 4° C.
4. Mn Y PS (10 mg/mL) was activated with 3 mM $NaIO_4$ at 4° C. overnight, quenched with 25 mM glycerol and dialyzed against $H_2O$ at 4° C.

Conjugation of Activated Mn A, C, W135 and Y PS Mixture to Activated TT
1. Aliquot of activated aldehyde-containing Mn A, C, W135 and Y PS was mixed at 1:1:1:1 ratio (W/W; total PS=0.1 mg).
2. The PS mixture was kept on ice and mixed with 1 uL 1M MES, pH 6.
3. Total volume of the PS was brought up to 36.8 uL with ice-cold water.
4. Aliquot of hydrazide-containing TT (0.1 mg; 29.9 uL, 3.41 mg/mL) was added to the activated PS mixture on ice and mixed.
5. Incubated the reaction mixture at 4° C. for two overnights.
6. Added 1 uL 1 M MES, pH 6.5.
7. The reaction mixture was treated with 2 uL 1 M $NaBH_4$ at 4° C. overnight.
8. The solution was buffer-exchanged with saline, 10 mM HEPES, pH 7.5, 1 mM EDTA, 4° C. using a 12-14 KDa molecular weight cut-off membrane.
9. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot TTHACWY061126

Figure 14:
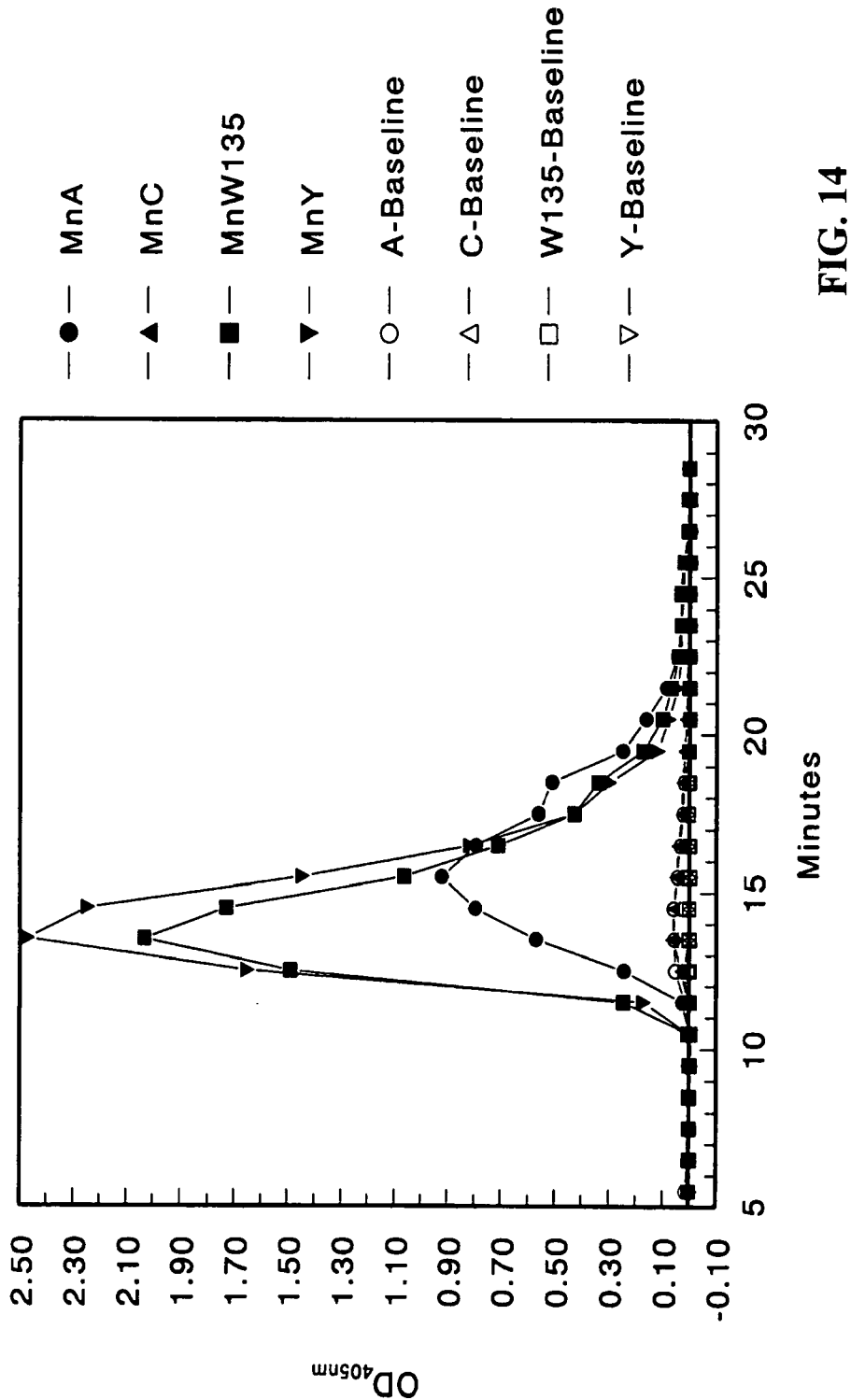
FIG. 14 ELISA detection of conjugated component polysaccharide in the combined synthesized multi-valent conjugate vaccine of lot TTHACWY061126. A 25 uL conjugate sample containing 0.05 mg/mL protein (tetanus toxoid) and 0.0125 mg/mL each of Mn A, C, W135 and Y PS was analyzed by HPLC. Only protein-containing species (i.e. conjugates and free TTH) of the HPLC fractions adhered to the ELISA plate during coating, and the conjugated polysaccharides were subsequently detected by antisera specific to each respective PS but not cross-reacting to tetanus toxoid (solid symbols). Significant incorporation of Mn A, W135 and Y PS into the conjugate is indicated by their respective ELISA signals as compared to Mn C PS of weak ELISA signal. This is attributed to the weaker reactivity of activated Mn C PS in conjugating to TTH as compared to activated Mn A, W135 and Y PS. This observation is consistent with the immunogenicity data of the conjugate showing lower efficacy for Mn C. A sample of native polysaccharide mixture was also analyzed in parallel (open symbols). Only native Mn A PS shows weak signal compared to the conjugate in this ELISA detection.

Conjugate lot TTHACWY061126 was analyzed by HPSEC elution profiles (monitored at 280 nm). Shift of the protein signal from 17.5 to 14 minute was observed upon conjugation, and little un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 14).

Immunogenicity of Combined Synthesized Multi-Valent Conjugate Lot TTHACWY061126

The conjugate was used to immunize a group of 15 mice with native polysaccharide mixture (5 mice) as a control at 1 μg each polysaccharide/dose on days 0, 14 and 28. The geometric means of the induced antibody levels (units/mL) two weeks post $3^{rd}$ injection determined by ELISA are Mn A, 108 (39, 296; 1 SD confidence interval); Mn C, 416 (221, 784); Mn W135, 52 (29, 96); and Mn Y, 386 (232, 644) for control group and Mn A, 29819 (18049, 49266); Mn C, 1319 (372, 4674); Mn W135, 11075 (4610, 26607); and Mn Y, 39901 (24295, 65530) for the conjugate, assuming 3200 units/mL for the reference serum of each PS (Table 11a). The conjugates induced 3-268 folds more anti-Mn PS specific antibody in mice as compared to the native Mn PS control. The geometric means of the induced bactericidal titer two weeks post $3^{rd}$ injection determined by bactericidal assay are Mn A, 394 (114, 1358; 1 SD confidence interval), MnC, 226 (97, 529); Mn W135, 10396 (6146, 17585); and Mn Y, 9050 (9050, 9050) for control group and Mn A, 12125 (3800, 38689), Mn C, 1811 (621, 5282); Mn W135, 89595 (28643, 280251); and Mn Y, 128062 (25097, 653452) for the conjugate batch (Table 11b). The conjugates induced 8-31 folds more bactericidal titer in mice as compared to the native Mn PS control.

TABLE 11a

The geometric mean anti-Mn PS antibody levels[a] with 1 SD confidence interval of mouse groups (5 mice for native PS mixture control and 15 mice for experiment) two weeks post $3^{rd}$ immunization with 1 μg/dose each of Mn PS in multi-valent conjugate lot TTHACWY061126.

| Polysaccharide | Native PS mixture | Lot TTHACWY061126 | Fold increase |
|---|---|---|---|
| A | 108 (39, 296) | 29819 (18049, 49266) | 268 |
| C | 416 (221, 784) | 1319 (372, 4674) | 3 |
| W135 | 52 (29, 96) | 11075 (4610, 26607) | 213 |
| Y | 386 (232, 644) | 39901 (24295, 65530) | 103 |

[a]Compared to a reference serum of each PS with an assigned anti-Mn PS antibody level of 3200 units/mL.

TABLE 11b

The geometric mean bactericidal titer with 1 SD confidence interval of mouse groups (5 mice for native PS mixture control and 15 mice for experiment) two weeks post $3^{rd}$ immunization with 1 μg/dose each of Mn PS in multi-valent conjugate lot TTHACWY061126.

| Polysaccharide | Native PS mixture | Lot TTHACWY061126 | Fold increase |
|---|---|---|---|
| A | 394 (114, 1358) | 12125 (3800, 38689) | 31 |
| C | 226 (97, 529) | 1811 (621, 5282) | 8 |
| W135 | 10396 (6146, 17585) | 89595 (28643, 280251) | 9 |
| Y | 9050 (9050, 9050) | 128062 (25097, 653452) | 14 |

Method B—Combined Synthesized Multivalent Meningococcal Groups A, C, W135 and Y Polysaccharides-Tetanus Toxoid Conjugate Lot TTHVIIACWYa060922B(2:2)

Activation of TT to Contain Hydrazide Groups
1. Tetanus toxoid (4.2 mg/mL) was activated with 0.42 M hydrazine in the presence of 30 mM EDC, 0.1 M MES, pH 5.5 at 20-24° C.
2. After reacting for 1 hours, the pH of the reaction mixture was raised to 7.5-10 with 1 N NaOH to stop the reaction.
3. The reaction mixture was buffer-exchanged with 30 mM NaCl, 3 mM $Na_2CO_3$, pH about 10.5 at 4° C. using a 12-14 KDa dialysis membrane.

Activation of Mn A, C, W135 and Y PS Mixture to Contain Cyanate Groups
Mn A, C, W135 and Y PS mixture (1:1:1:1, W/W; 0.0125 mL, 10 mg/mL) was activated with 0.75 uL CDAP (100 mg/mL in acetonitrile) for 2-2.5 minutes at 20-24° C. in the presence of 0.5 uL 0.2 M triethylamine.

Conjugation of Activated Mn A, C, W135 and Y PS Mixture to Activated TT
1. The activated polysaccharide was mixed with 50 uL ice-cold 2×PBS, pH 7.4 followed by addition of 0.125 mg TTH (32.3 uL, 3.87 mg/mL, ice-cold).
2. Incubated the reaction mixture at 4° C. with gentle shaking for 3 overnights. (The prolonged incubation is to ensure complete conjugation as well as decomposition of the residual left-over unreacted cyanate groups.)
3. The solution was buffer-exchanged at 4° C. with saline, 10 mM HEPES, pH 7.5, 1 mM EDTA using a 12-14 KDa molecular weight cut-off membrane.
4. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot TTHVIIACWYa060922B(2:2)

Conjugate lot TTHVIIACWYa060922B(2:2) was analyzed by HPSEC elution profiles (monitored at 280 nm). Shift of the protein signal from 17.5 to 14 minute was observed upon conjugation, and little un-conjugated free protein was left after conjugation. The conjugated polysaccharide of each meningococcal serogroup A, C, W135 or Y in each fraction of the HPLC profile was detected by ELISA with respective antibodies specific to each polysaccharide.

Immunogenicity of Combined Synthesized Multi-Valent Conjugate Lot TTHVIIACWYa060922B(2:2)

The conjugate was used to immunize a group of 5 mice with native polysaccharide as a control at 1 μg each polysaccharide/dose on days 0, 14 and 28. The geometric means of the induced antibody levels (units/mL) two weeks post $3^{rd}$ injection determined by ELISA are Mn A, 108 (39, 296; 1 SD confidence interval); MnC, 416 (221, 784); Mn W135, 52 (29, 96); and Mn Y, 386 (232, 644) for the control and Mn A, 24828 (16738, 36829); Mn C, 10641 (6118, 18506); Mn W135, 15068 (7374, 30788); and Mn Y, 99827 (56810, 175416) for the conjugate group, assuming 3200 units/mL for the reference serum of each PS (Table 12a). The conjugates induced 26-290 folds more anti-Mn PS specific antibody in mice as compared to the native Mn PS control. The geometric means of the induced bactericidal titer two weeks post $3^{rd}$ injection determined by bactericidal assay are Mn A, 394 (114, 1358; 1 SD confidence interval), MnC, 226 (97, 529); Mn W135, 10396 (6146, 17585); and Mn Y, 9050 (9050, 9050) for control group and Mn A, 5970 (3212, 11099), Mn C, 19400 (8185, 45985); Mn W135, 68593 (19473, 241620); and Mn Y, 111431 (45134, 275106) for the conjugate batch (Table 12b). The conjugates induced 7-86 folds more bactericidal titer in mice as compared to the native Mn PS control.

TABLE 12a

The geometric mean anti-Mn PS antibody levels[a] with 1 SD confidence interval of mouse groups (5 mice for native PS mixture control and 5 mice for experiment) two weeks post $3^{rd}$ immunization with 1 μg/dose each of Mn PS in multi-valent conjugate lot TTHVIIACWYa060922B(2:2).

| Polysaccharide | Native PS mixture | Lot TTHVIIACWYa060922B (2:2) | Fold increase |
|---|---|---|---|
| A | 108 (39, 296) | 24828 (16738, 36829) | 230 |
| C | 416 (221, 784) | 10641 (6118, 18506) | 26 |
| W135 | 52 (29, 96) | 15068 (7374, 30788) | 290 |
| Y | 386 (232, 644) | 99827 (56810, 175416) | 259 |

[a]Compared to a reference serum of each PS with an assigned anti-Mn PS antibody level of 3200 units/mL.

TABLE 12b

The geometric mean bactericidal titer with 1 SD confidence interval of mouse groups (5 mice per group) two weeks post $3^{rd}$ immunization with 1 μg/dose each of Mn PS in multi-valent conjugate lot TTHVIIACWYa060922B(2:2).

| Polysaccharide | Native PS mixture | Lot TTHVIIACWYa060922B (2:2) | Fold increase |
|---|---|---|---|
| A | 394 (114, 1358) | 5971 (3212, 11099) | 15 |
| C | 226 (97, 529) | 19499 (8185, 45985) | 86 |
| W135 | 10396 (6146, 17585) | 68593 (19473, 241620) | 7 |
| Y | 9050 (9050, 9050) | 111431 (45134, 275106) | 12 |

Method A—Combined Synthesized Multivalent Meningococcal Groups A, C, W135 and Y Polysaccharides-Tetanus Toxoid Conjugate Lot TTH2C/A/WY070209

Activation of TT to Contain Hydrazide Groups
1. Tetanus toxoid (4.2 mg/mL) was activated with 0.42 M hydrazine in the presence of 20 mM EDC, 0.1 M MES, pH 5.5 at 20-24° C.
2. After reacting for 4 hours, the pH of the reaction mixture was raised to 7.5-10 with 1 N NaOH to stop the reaction.
3. The reaction mixture was buffer-exchanged with 30 mM NaCl, 3 mM $Na_2CO_3$, pH about 10.5 at 4° C. using a 12-14 KDa dialysis membrane.

Activation of Individual Mn A, C, W135 and Y PS by $NaIO_4$ to Contain Aldehyde Groups
1. Mn A PS (10 mg/mL) was activated with 15 mM $NaIO_4$ at 4° C. for 72 hrs, quenched with 25 mM glycerol and dialyzed against $H_2O$ at 4° C.
2. Mn C PS (10 mg/mL) was activated with 6 mM $NaIO_4$ at room temperature for 4 hrs, quenched with 25 mM glycerol and dialyzed against $H_2O$ at 4° C.
3. Mn W135 PS (10 mg/mL) was activated with 3 mM $NaIO_4$ at 4° C. overnight, quenched with 25 mM glycerol and dialyzed against $H_2O$ at 4° C.
4. Mn Y PS (10 mg/mL) was activated with 3 mM $NaIO_4$ at 4° C. overnight, quenched with 25 mM glycerol and dialyzed against $H_2O$ at 4° C.

Conjugation of Activated Mn A, C, W135 and Y PS Mixture to Activated TT
1. Aliquot (0.1 mg) of activated Mn C PS was lyophilized and re-dissolved in 1 uL 1M MES, pH 6.
2. Aliquot of hydrazide-containing TT (0.2 mg) was lyophilized and re-dissolved in 2 uL $H_2O$.
3. Add the protein solution to the activated Mn C PS solution at 4° C. on day 1; mix; and incubate overnight at 4° C.
4. At 4° C., add 0.05 mg of activated Mn A PS in 2-7 uL to the hydrazide-containing TT/activated Mn C PS reaction mixture on day 2; mix; and incubate overnight at 4° C.
5. At 4° C., add ice-cold saline and 0.05 mg each of activated Mn W135 and Y PS's to the reaction mixture from step (4) on day 3 to total volume of 200 uL; mix; and incubate overnight at 4° C.
6. Added 2 uL 1 M MES, pH 6.5.
7. The reaction mixture was treated with 3 uL 1 M $NaBH_4$ at 4° C. overnight.
8. The solution was buffer-exchanged with saline, 10 mM HEPES, pH 7.5, 1 mM EDTA, 4° C. using a 12-14 KDa molecular weight cut-off membrane.
9. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot TTH2C/A/WY070209

Conjugate lot TTH2C/A/WY070209 was analyzed by HPSEC elution profiles (monitored at 280 nm). Shift of the protein signal from 17.5 to 14 minute was observed upon conjugation, and little un-conjugated free protein was left after conjugation. The conjugated polysaccharide of each meningococcal serogroup A, C, W135 or Y in each fraction of the HPLC profile was detected by ELISA with respective antibodies specific to each polysaccharide (FIG. 15).

Immunogenicity of Combined Synthesized Multi-Valent Conjugate Lot TTH2C/A/WY070209

The conjugate was used to immunize a group of 15 mice with native polysaccharide mixture (5 mice) as a control at 0.1 µg each PS/dose for Mn A, W135 and Y and 0.2 µg/dose for Mn C on days 0, 7 and 14. The geometric means of the induced antibody levels (units/mL) one week post 3rd injection determined by ELISA are Mn A, 1 (1, 1; 1 SD confidence interval); Mn C, 34 (10µ, 109); Mn W135, 1 (1, 1); and Mn Y, 28 (5, 166) for control group and Mn A, 10303 (5480, 19371); Mn C, 12815 (7350, 22343); Mn W135, 3111 (1490, 6494); and Mn Y, 9457 (4280, 20894) for the conjugate, assuming 3200 units/mL for the reference serum of each PS (Table 13a). The conjugates induced 338-10303 folds more anti-Mn PS specific antibody in mice as compared to the native Mn PS control. The geometric means of the induced bactericidal titer one week post 3rd injection determined by bactericidal assay are Mn A, 260 (127, 533; 1 SD confidence interval), MnC, 92 (76, 111); Mn W135, 858 (587, 1254); and Mn Y, 462 (53, 3998) for control group and MnA, 4321 (2192, 8521), Mn C, 1755 (931, 3310); Mn W135, 20030 (4288, 93566); and Mn Y, 7728 (2811, 21244) for the conjugate batch (Table 13b). The conjugates induced 17-23 folds more bactericidal titer in mice as compared to the native Mn PS control.

TABLE 13a

The geometric mean anti-Mn PS antibody levels[a] with 1 SD confidence interval of mouse groups (5 mice for native PS mixture control and 15 mice for experiment) one weeks post 3rd immunization with 0.1 µg/dose each PS of Mn A, W135 and Y and 0.2 µg/dose for Mn C in multi-valent conjugate lot TTH2C/A/WY070209.

| Polysac-charide | Native PS mixture | Lot TTH2C/A/WY070209 | Fold increase |
|---|---|---|---|
| A | 1 (1, 1) | 10303 (5480, 19371) | 10303 |
| C | 34 (10, 109) | 12815 (7350, 22343) | 377 |
| W135 | 1 (1, 1) | 3111 (1490, 6494) | 3111 |
| Y | 28 (5, 166) | 9457 (4280, 20894) | 338 |

[a]Compared to a reference serum of each PS with an assigned anti-Mn PS antibody level of 3200 units/mL.

TABLE 13b

The geometric mean bactericidal titer with 1 SD confidence interval of mouse groups (5 mice for native PS mixture control and 15 mice for experiment) one week post 3rd immunization with 0.1 µg/dose each PS of Mn A, W135 and Y and 0.2 µg/dose for Mn C in multi-valent conjugate lot TTH2C/A/WY070209

| Polysac-charide | Native PS mixture | Lot TTH2C/A/WY070209 | Fold increase |
|---|---|---|---|
| A | 260 (127, 533) | 4321 (2192, 8521) | 17 |
| C | 92 (76, 111) | 1755 (931, 3310) | 19 |
| W135 | 858 (587, 1254) | 20030 (4288, 93566) | 23 |
| Y | 462 (53, 3998) | 7728 (2811, 21244) | 17 |

Method B—Combined Synthesized Multivalent Meningococcal Groups A, C, W135 and Y Polysaccharides-Tetanus Toxoid Conjugate Lot TTHIAC/WY070210B(2:2)

Activation of TT to Contain Hydrazide Groups
1. Tetanus toxoid (4.2 mg/mL) was activated with 0.42 M hydrazine in the presence of 30 mM EDC, 0.1 M MES, pH 5.5 at 20-24° C.
2. After reacting for 3 hours, the pH of the reaction mixture was raised to 7.5-10 with 1 N NaOH to stop the reaction.
3. The reaction mixture was buffer-exchanged with 30 mM NaCl, 3 mM Na$_2$CO$_3$, pH about 10.5 at 4° C. using a 12-14 KDa dialysis membrane.

Activation of Mn A and C PS Mixture to Contain Cyanate Groups
  Mn A and C PS mixture (1:1, W/W; 0.025 mL, 10 mg/mL) was activated with 1.5 uL CDAP (100 mg/mL in acetonitrile) for 2-2.5 minutes at 20-24° C. in the presence of 1 uL 0.2 M triethylamine.

Conjugation of Activated Mn A and C PS Mixture to Activated TT
1. The activated polysaccharide was mixed with 200 uL ice-cold 2×PBS, pH 7.4 followed by addition of 0.5 mg ice-cold TTH.
2. Incubated the reaction mixture at 4° C. with gentle shaking overnight.

Activation of Mn W135 and Y PS Mixture to Contain Cyanate Groups
  Mn W135 and Y PS mixture (1:1, W/W; 0.025 mL, 10 mg/mL) was activated with 1.5 uL CDAP (100 mg/mL in acetonitrile) for 2-2.5 minutes at 20-24° C. in the presence of 1 uL 0.2 M triethylamine.

Conjugation of Activated Mn W135 and Y PS Mixture to Activated TT in the TTH+Activated Mn A and C Reaction Mixture
1. The activated Mn W135 and Y mixture was mixed with the TTH+activated Mn A and C reaction mixture on ice.
2. Incubated the reaction mixture at 4° C. with gentle shaking for 3 overnights. (The prolonged incubation is to ensure complete conjugation as well as decomposition of the residual left-over unreacted cyanate groups.)
3. The solution was buffer-exchanged at 4° C. with saline, 10 mM HEPES, pH 7.5, 1 mM EDTA using a 12-14 KDa molecular weight cut-off membrane.
4. Volume of the dialyzed conjugate was determined, and the concentrations of the protein (TT) and each polysaccharide (Mn A, C, W135 and Y) were calculated from the input masses.

Characterization of Combined Synthesized Multi-Valent Conjugate Lot TTHIAC/WY070210B(2:2)

Conjugate lot TTHIAC/WY070210B(2:2) was analyzed by HPSEC elution profiles (monitored at 280 nm). Shift of the protein signal from 17.5 to 14 minute was observed upon conjugation, and little un-conjugated free protein was left after conjugation. The conjugated polysaccharide of each meningococcal serogroup A, C, W135 or Y in each fraction of the HPLC profile was detected by ELISA with respective antibodies specific to each polysaccharide.

Immunogenicity of Combined Synthesized Multi-Valent Conjugate Lot TTHIAC/WY070210B(2:2)

The conjugate was used to immunize a group of 5 mice with native polysaccharide as a control at 0.1 µg each polysaccharide/dose on days 0, 7 and 14. The geometric means of the induced antibody levels (units/mL) one week post 3rd injection determined by ELISA are Mn A, 1 (1, 1; 1 SD confidence interval); MnC, 34 (10, 109); Mn W135, 1 (1, 1); and Mn Y, 28 (5, 166) for the control and Mn A, 5873 (3966, 8699); Mn C, 3465 (2109, 5695); Mn W135, 3798 (2090, 6900); and Mn Y, 22423 (11933, 42133) for the conjugate group, assuming 3200 units/mL for the reference serum of each PS (Table 14a). The conjugates induced 102-5873 folds more anti-Mn PS specific antibody in mice as compared to the native Mn PS control. The geometric means of the induced bactericidal titer one weeks post 3rd injection determined by bactericidal assay are Mn A, 260 (127, 533; 1 SD confidence interval), MnC, 92 (76, 111); Mn W135, 858 (587, 1254); and Mn Y, 462 (53, 3998) for control group and Mn A, 4127 (2196, 7756), Mn C, 1331 (588, 3010); Mn W135, 38508 (17971, 82515); and Mn Y, 11506 (7700, 17194) for the conjugate batch (Table 14b). The conjugates induced 14-45 folds more bactericidal titer in mice as compared to the native Mn PS control.

TABLE 14a

The geometric mean anti-Mn PS antibody levels[a] with 1 SD confidence interval of mouse groups (5 mice for native PS mixture control and 5 mice for experiment) one week post 3rd immunization with 0.1 μg/dose each of Mn PS in multi-valent conjugate lot TTHIAC/WY070210B(2:2).

| Polysac-charide | Native PS mixture | Lot TTHIAC/WY070210B(2:2) | Fold increase |
|---|---|---|---|
| A | 1 (1, 1) | 5873 (3966, 8699) | 5873 |
| C | 34 (10, 109) | 3465 (2109, 5695) | 102 |
| W135 | 1 (1, 1) | 3798 (2090, 6900) | 3798 |
| Y | 28 (5, 166) | 22423 (11933, 42133) | 801 |

[a]Compared to a reference serum of each PS with an assigned anti-Mn PS antibody level of 3200 units/mL.

TABLE 14b

The geometric mean bactericidal titer with 1 SD confidence interval of mouse groups (5 mice per group) one week post 3rd immunization with 0.1 μg/dose each of Mn PS in multi-valent conjugate lot TTHIAC/WY070210B(2:2).

| Polysac-charide | Native PS mixture | Lot TTHIAC/WY070210B(2:2) | Fold increase |
|---|---|---|---|
| A | 260 (127, 533) | 4127 (2196, 7756) | 16 |
| C | 92 (76, 111) | 1331 (588, 3010) | 14 |
| W135 | 858 (587, 1254) | 38508 (17971, 82515) | 45 |
| Y | 462 (53, 3998) | 11506 (7700, 17194) | 25 |

Method B—Combined Synthesized Multivalent Pneumococcal Serotypes 4, 6B, 9V, 14, 18C, 19F and 23F Polysaccharides-Tetanus Toxoid Conjugate Lot 7-041111AIa
Activation of TT to Contain Hydrazide Groups
 4. Tetanus toxoid (4.2 mg/mL) was activated with 0.42 M hydrazine in the presence of 20 mM EDC, 0.1 M MES, pH 6.5 at 20-24° C.
 5. After reacting for 4 hours, the pH of the reaction mixture was raised to 7.5-10 with 1 N NaOH to stop the reaction.
 6. The reaction mixture was buffer-exchanged with 30 mM NaCl, 3 mM Na$_2$CO$_3$, pH about 10.5 at 4° C. using a 12-14 KDa dialysis membrane.
Activation of Pn 4, 6B, 9V, 14, 18C, 19F and 23F PS Mixture to Contain Cyanate Groups
 3. Pn 4, 6B, 9V, 14, 18C, 19F and 23F mixture (0.1 mL; 1.429 mg/mL each PS) was activated with 8 uL CDAP (100 mg/mL in acetonitrile) for 2-2.5 minutes at 20-24° C. in the presence of 8 uL 0.2 M triethylamine.
 4. The activated polysaccharide was mixed with 1.25 mL ice-cold 0.2 M HEPES, pH 7.5, 30 mM EDTA, and immediately used for conjugation.
Conjugation of Activated Pn 4, 6B, 9V, 14, 18C, 19F and 23F PS Mixture to Activated TT
 5. The activated polysaccharide was combined with 0.5 mg activated TT (ice-cold, 0.15 mL, 3.4 mg/mL); vortex.
 6. Incubated the reaction mixture at 4° C. with gentle shaking for 3 overnights. (The prolonged incubation is to ensure decomposition of the residual left over unreacted cyanate groups.)
 7. The solution was buffer-exchanged with saline, 10 mM HEPES, pH 7.5, 1 mM EDTA using a 12-14 KDa molecular weight cut-off membrane.
 8. Volume of the dialyzed conjugate was determined, and the concentrations of the protein (TT) and each polysaccharide (Pn 4, 6B, 9V, 14, 18C, 19F and 23F) were calculated from the input masses.
Immunogenicity of Combined Synthesized Multi-Valent Conjugates Lot 7-041111AIa The conjugates were used to immunize groups of 4-5 mice with native polysaccharide mixture as a control at 1 μg/dose each Pn PS on days 0, 14 and 28. The geometric means of the induced antibody levels (units/mL) two weeks post 3$^{rd}$ injection determined by ELISA are Pn 4, 15 (4, 65; 1 SD confidence interval), Pn 6B, 25 (22, 28); Pn 9V, 5 (2, 15); Pn 14, 6 (3, 11) and Pn 18C, 1 (1, 1) for control group and Pn 4, 9167 (3136, 16359), Pn 6B, 5828 (1581, 21490); Pn 9V, 14591 (5205, 40901); Pn 14, 2558 (1667, 3925) and Pn 18C, 2094 (818, 5362) for the conjugate Lot 7-041111AIa, assuming 3200 units/mL for the reference serum of each serogroup PS. The conjugates induced 234-2918 folds more anti-Pn PS specific antibody in mice as compared to the native Pn PS control (Table 15). The immunogenicity of Pn 19F and 23F PS conjugate components by ELISA was not determined.

TABLE 15

The geometric mean anti-Pn PS antibody levels[a] with 1 SD confidence interval of mouse groups (4-5 mice per group) two weeks post 3$^{rd}$ immunization with 1 μg/dose each Pn PS in multi-valent conjugate Lot 7-041111AIa

| Pn PS | Native PS mixture | Lot 7-041111AIa | Fold increase |
|---|---|---|---|
| 4 | 15 (4, 65) | 9167 (3136, 16359) | 611 |
| 6B | 25 (22, 28) | 5828 (1581, 21490) | 234 |
| 9V | 5 (2, 15) | 14591 (5205, 40901) | 2918 |
| 14 | 6 (3, 11) | 2558 (1667, 3925) | 426 |
| 18C | 1 (1, 1) | 2094 (818, 5362) | 2094 |

[a]Compared to a reference serum of each PS with an assigned anti-PS antibody level of 3200 units/mL.

Method B—Combined Synthesized Multivalent Pneumococcal Serotypes 4, 6B, 9V, 14, 18C, 19F and 23F Polysaccharides-(Tetanus Toxoid+Bovine Thyroglobulin+Ovalbumin+ Bovine Serum Albumin) Conjugate (Lot 7-041111AIb)
Activation of Mixture of Tetanus Toxoid, Bovine Thyroglobulin, Ovalbumin and Bovine Serum Albumin to Contain Hydrazide Groups
 7. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.
 8. After reacting for 4 hours, the pH of the reaction mixture was raised to 7.5-10 with 1 N NaOH to stop the reaction.
 9. The reaction mixture was buffer-exchanged with 30 mM NaCl, 3 mM Na$_2$CO$_3$, pH about 10.5 at 4° C. using a 12-14 KDa dialysis membrane.
Activation of Pn 4, 6B, 9V, 14, 18C, 19F and 23F PS Mixture to Contain Cyanate Groups
 5. Pn 4, 6B, 9V, 14, 18C, 19F and 23F mixture (0.1 mL; 1.429 mg/mL each PS) was activated with 8 uL CDAP (100 mg/mL in acetonitrile) for 2-2.5 minutes at 20-24° C. in the presence of 8 uL 0.2 M triethylamine.
 6. The activated polysaccharide was mixed with 1.25 mL ice-cold 0.2 M HEPES, pH 7.5, 30 mM EDTA, and immediately used for conjugation.
Conjugation of Activated Pn 4, 6B, 9V, 14, 18C, 19F and 23F PS Mixture to Activated Mixture of Tetanus Toxoid, Bovine Thyroglobulin, Ovalbumin and Bovine Serum Albumin 9. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.
10. Incubated the reaction mixture at 4° C. with gentle shaking for 3 overnights. (The prolonged incubation is to ensure decomposition of the residual left over unreacted cyanate groups.)
11. The solution was buffer-exchanged with saline, 10 mM HEPES, pH 7.5, 1 mM EDTA using a 12-14 KDa molecular weight cut-off membrane.
12. Volume of the dialyzed conjugate was determined, and the concentrations of the protein (TT+bovine thyroglobulin+ovalbumin+bovine serum albumin) and each polysaccharide (Pn 4, 6B, 9V, 14, 18C, 19F and 23F) were calculated from the input masses.

Immunogenicity of Combined Synthesized Multi-Valent Conjugates Lot 7-041111AIb

The conjugates were used to immunize groups of 4-5 mice with native polysaccharide mixture as a control at 1 μg/dose each Pn PS on days 0, 14 and 28. The geometric means of the induced antibody levels (units/mL) two weeks post $3^{rd}$ injection determined by ELISA are Pn 4, 15 (4, 65; 1 SD confidence interval), Pn 6B, 25 (22, 28); Pn 9V, 5 (2, 15); Pn 14, 6 (3, 11) and Pn 18C, 1 (1, 1) for control group and Pn 4, 9658 (5717, 16318), Pn 6B, 2194 (414, 11635); Pn 9V, 3839 (1365, 10793); Pn 14, 1148 (865, 1525) and Pn 18C, 233 (42, 1300) for the conjugate Lot 7-041111AIb, assuming 3200 units/mL for the reference serum of each serogroup PS. The conjugates induced 233-768 folds more anti-Pn PS specific antibody in mice as compared to the native Pn PS control (Table 16). The immunogenicity of Pn 19F and 23F PS conjugate components by ELISA was not determined.

TABLE 16

The geometric mean anti-Pn PS antibody levels[a] with 1 SD confidence interval of mouse groups (4-5 mice per group) two weeks post $3^{rd}$ immunization with 1 μg/dose each Pn PS in multi-valent conjugate Lot 7-041111AIb

| PnPS | Native PS mixture | Lot 7-041111AIb | Fold increase |
| --- | --- | --- | --- |
| 4 | 15 (4, 65) | 9658 (5717, 16318) | 644 |
| 6B | 25 (22, 28) | 2194 (414, 11635) | 88 |
| 9V | 5 (2, 15) | 3839 (1365, 10793) | 768 |
| 14 | 6 (3, 11) | 1148 (865, 1525) | 191 |
| 18C | 1 (1, 1) | 233 (42, 1300) | 233 |

[a]Compared to a reference serum of each PS with an assigned anti-PS antibody level of 3200 units/mL.

Method B—Combined Synthesized Multivalent Pneumococcal (Pn) Serotypes 4, 6B, 9V, 14, 18C, 19F and 23F, and *Haemophilus Influenzae* Type B (Hib) Polysaccharides-Tetanus Toxoid Conjugate Lot 8-041111AIIa Activation of TT to Contain Hydrazide Groups
10. Tetanus toxoid (4.2 mg/mL) was activated with 0.42 M hydrazine in the presence of 20 mM EDC, 0.1 M MES, pH 6.5 at 20-24° C.
11. After reacting for 4 hours, the pH of the reaction mixture was raised to 7.5-10 with 1 N NaOH to stop the reaction.
12. The reaction mixture was buffer-exchanged with 30 mM NaCl, 3 mM $Na_2CO_3$, pH about 10.5 at 4° C. using a 12-14 KDa dialysis membrane.

Activation of Pn 4, 6B, 9V, 14, 18C, 19F and 23F, and Hib PS Mixture to Contain Cyanate Groups
7. Pn 4, 6B, 9V, 14, 18C, 19F and 23F, and Hib PS mixture (0.1149 mL; 0.87 mg/mL for each Pn PS and 2.611 mg/mL for Hib PS) was activated with 8 uL CDAP (100 mg/mL in acetonitrile) for 2-2.5 minutes at 20-24° C. in the presence of 8 uL 0.2 M triethylamine.
8. The activated polysaccharide was mixed with 1.25 mL ice-cold 0.2 M HEPES, pH 7.5, 30 mM EDTA, and immediately used for conjugation.

Conjugation of Activated Pn 4, 6B, 9V, 14, 18C, 19F and 23F, and Hib PS Mixture to Activated TT
13. The activated polysaccharide was combined with 0.5 mg activated TT (ice-cold, 0.15 mL, 3.4 mg/mL); vortex.
14. Incubated the reaction mixture at 4° C. with gentle shaking for 3 overnights. (The prolonged incubation is to ensure decomposition of the residual left over unreacted cyanate groups.)
15. The solution was buffer-exchanged with saline, 10 mM HEPES, pH 7.5, 1 mM EDTA using a 12-14 KDa molecular weight cut-off membrane.
16. Volume of the dialyzed conjugate was determined, and the concentrations of the protein (TT) and each polysaccharide (Pn 4, 6B, 9V, 14, 18C, 19F and 23F, and Hib) were calculated from the input masses.

Immunogenicity of Combined Synthesized Multi-Valent Conjugates Lot 8-041111AIIa

The conjugates were used to immunize groups of 4-5 mice with native polysaccharide mixture as a control at 1 μg/dose each Pn PS and 3 μg/dose Hib PS on days 0, 14 and 28. The geometric means of the induced antibody levels (units/mL) two weeks post $3^{rd}$ injection determined by ELISA are Pn 4, 7 (2, 12; 1 SD confidence interval), Pn 6B, 5(3, 11); Pn 9V, 18 (9, 34); Pn 14, 5 (3, 11): Pn 18C, 13 (10μ, 16) and Hib, 26 (19, 35) for control group and Pn 4, 4134 (2318, 7374), Pn 6B, 232 (37, 1467); Pn 9V, 12679 (7337, 21911); Pn 14, 1479 (1185, 1845); Pn 18C, 2134 (305, 14924); and Hib 226 (53, 966) for the conjugate Lot 8-041111AIIa, assuming 3200 units/mL for the reference serum of each serogroup PS. The conjugates induced 9-704 folds more anti-PS specific antibody in mice as compared to the native PS control (Table 17). The immunogenicity of Pn 19F and 23F PS conjugate components by ELISA was not determined.

TABLE 17

The geometric mean anti-PS antibody levels[a] with 1 SD confidence interval of mouse groups (4-5 mice per group) two weeks post $3^{rd}$ immunization with 1 μg/dose each Pn PS and 3 μg/dose Hib PS in multi-valent conjugate Lot 8-041111AIIa

| PS | Native PS mixture | Lot 8-041111AIIa | Fold increase |
| --- | --- | --- | --- |
| 4 | 7 (2, 12) | 4134 (2318, 7374) | 591 |
| 6B | 5 (3, 11) | 232 (37, 1467) | 46 |
| 9V | 18 (9, 34) | 12679 (7337, 21911) | 704 |
| 14 | 5 (3, 11) | 1479 (1185, 1845) | 296 |
| 18C | 13 (10, 16) | 2134 (305, 14924) | 164 |
| Hib | 26 (19, 35) | 226 (53, 966) | 9 |

[a]Compared to a reference serum of each PS with an assigned anti-PS antibody level of 3200 units/mL.

Method B—Combined Synthesized Multivalent Pneumococcal (Pn) Serotypes 4, 6B, 9V, 14, 18C, 19F and 23F, and *Haemophilus Influenzae* Type B (Hib) Polysaccharides-(Tetanus Toxoid+Bovine Thyroglobulin+Ovalbumin+Bovine Serum Albumin) Conjugate (Lot 8-041111AIIb)

Activation of Mixture of Tetanus Toxoid, Bovine Thyroglobulin, Ovalbumin and Bovine Serum Albumin to Contain Hydrazide Groups
13. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.

14. After reacting for 4 hours, the pH of the reaction mixture was raised to 7.5-10 with 1 N NaOH to stop the reaction.

15. The reaction mixture was buffer-exchanged with 30 mM NaCl, 3 mM $Na_2CO_3$, pH about 10.5 at 4° C. using a 12-14 KDa dialysis membrane.

Activation of Pn 4, 6B, 9V, 14, 18C, 19F and 23F, and Hib PS Mixture to Contain Cyanate Groups 9. Pn 4, 6B, 9V, 14, 18C, 19F and 23F, and Hib PS mixture (0.1149 mL; 0.87 mg/mL for each Pn PS and 2.611 mg/mL for Hib PS) was activated with 8 uL CDAP (100 mg/mL in acetonitrile) for 2-2.5 minutes at 20-24° C. in the presence of 8 uL 0.2 M triethylamine.

10. The activated polysaccharide was mixed with 1.25 mL ice-cold 0.2 M HEPES, pH 7.5, 30 mM EDTA, and immediately used for conjugation.

Conjugation of Activated Pn 4, 6B, 9V, 14, 18C, 19F and 23F, and Hib PS Mixture to Activated Mixture of Tetanus Toxoid, Bovine Thyroglobulin, Ovalbumin and Bovine Serum Albumin 17. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.

18. Incubated the reaction mixture at 4° C. with gentle shaking for 3 overnights. (The prolonged incubation is to ensure decomposition of the residual left over unreacted cyanate groups.)

19. The solution was buffer-exchanged with saline, 10 mM HEPES, pH 7.5, 1 mM EDTA using a 12-14 KDa molecular weight cut-off membrane.

20. Volume of the dialyzed conjugate was determined, and the concentrations of the protein (TT+bovine thyroglobulin+ovalbumin+bovine serum albumin) and each polysaccharide (Pn 4, 6B, 9V, 14, 18C, 19F and 23F, and Hib) were calculated from the input masses.

Immunogenicity of Combined Synthesized Multi-Valent Conjugates Lot 8-041111AIIb

The conjugates were used to immunize groups of 4-5 mice with native polysaccharide mixture as a control at 1 μg/dose each Pn PS and 3 μg/dose Hib PS on days 0, 14 and 28. The geometric means of the induced antibody levels (units/mL) two weeks post $3^{rd}$ injection determined by ELISA are Pn 4, 7 (2, 12; 1 SD confidence interval), Pn 6B, 5(3, 11); Pn 9V, 18 (9, 34); Pn 14, 5 (3, 11): Pn 18C, 13 (10, 16) and Hib, 26 (19, 35) for control group and Pn 4, 7332 (4545, 11819), Pn 6B, 46 (32, 61); Pn 9V, 19560 (6371, 60050); Pn 14, 3385 (700, 3001); Pn 18C, 3010 (894, 10126); and Hib 272 (62, 1188) for the conjugate Lot 8-041111AIIb, assuming 3200 units/mL for the reference serum of each serogroup PS. The conjugates induced 233-768 folds more anti-PS specific antibody in mice as compared to the native PS control (Table 18). The immunogenicity of Pn 19F and 23F PS conjugate components by ELISA was not determined.

TABLE 18

The geometric mean anti-PS antibody levels[a] with 1 SD confidence interval of mouse groups (4-5 mice per group) two weeks post $3^{rd}$ immunization with 1 μg/dose each Pn PS and 3 μg/dose Hib PS in multi-valent conjugate Lot 8-041111AIIb

| PS | Native PS mixture | Lot 8-041111AIIb | Fold increase |
|---|---|---|---|
| 4 | 7 (2, 12) | 7332 (4545, 11831) | 1047 |
| 6B | 5 (3, 11) | 46 (32, 61) | 9 |
| 9V | 18 (9, 34) | 19560 (6371, 60050) | 1087 |
| 14 | 5 (3, 11) | 3385 (700, 3001) | 677 |
| 18C | 13 (10, 16) | 3010 (894, 10126) | 232 |
| Hib | 26 (19, 35) | 272 (62, 1188) | 10 |

[a]Compared to a reference serum of each PS with an assigned anti-PS antibody level of 3200 units/mL.

Method B—Combined Synthesized Multivalent Pneumococcal (Pn) Serotypes 4, 6B, 9V, 14, 18C, 19F and 23F, and Meningococcal (Mn) Serogroups A, C, W135 and Y Polysaccharides-Tetanus Toxoid Conjugate Lot 11-041111BIa Activation of TT to Contain Hydrazide Groups 16. Tetanus toxoid (4.2 mg/mL) was activated with 0.42 M hydrazine in the presence of 20 mM EDC, 0.1 M MES, pH 6.5 at 20-24° C.

17. After reacting for 4 hours, the pH of the reaction mixture was raised to 7.5-10 with 1 N NaOH to stop the reaction.

18. The reaction mixture was buffer-exchanged with 30 mM NaCl, 3 mM $Na_2CO_3$, pH about 10.5 at 4° C. using a 12-14 KDa dialysis membrane.

Activation of Pn 4, 6B, 9V, 14, 18C, 19F and 23F, and Mn A, C, W135 and Y PS Mixture to Contain Cyanate Groups 11. Pn 4, 6B, 9V, 14, 18C, 19F and 23F, and Mn A, C, W135 and Y PS mixture (0.1 mL; 0.909 mg/mL each PS) was activated with 8 uL CDAP (100 mg/mL in acetonitrile) for 2-2.5 minutes at 20-24° C. in the presence of 8 uL 0.2 M triethylamine.

12. The activated polysaccharide was mixed with 1.25 mL ice-cold 0.2 M HEPES, pH 7.5, 30 mM EDTA, and immediately used for conjugation.

Conjugation of Activated Pn 4, 6B, 9V, 14, 18C, 19F and 23F, and Mn A, C, W135 and Y PS Mixture to Activated TT 21. The activated polysaccharide mixture was combined with 0.5 mg activated TT (ice-cold, 0.15 mL, 3.4 mg/mL); vortex.

22. Incubated the reaction mixture at 4° C. with gentle shaking for 3 overnights. (The prolonged incubation is to ensure decomposition of the residual left over unreacted cyanate groups.)

23. The solution was buffer-exchanged with saline, 10 mM HEPES, pH 7.5, 1 mM EDTA using a 12-14 KDa molecular weight cut-off membrane.

24. Volume of the dialyzed conjugate was determined, and the concentrations of the protein (TT) and each polysaccharide (Pn 4, 6B, 9V, 14, 18C, 19F and 23F, and Mn A, C, W135 and Y) were calculated from the input masses.

Immunogenicity of Combined Synthesized Multi-Valent Conjugates Lot 11-041111BIa

The conjugates were used to immunize groups of 4-5 mice with native polysaccharide mixture as a control at 1 μg/dose each Pn and Mn PS on days 0, 14 and 28. The geometric means of the induced antibody levels (units/mL) two weeks post $3^{rd}$ injection determined by ELISA are Pn 4, 1 (1, 2; 1 SD confidence interval), Pn 6B, 17 (7, 40); Pn 9V, 54 (13, 229); Pn 14, 7 (2, 14); Pn 18C, 2 (1, 3); Mn A, 168 (111, 255); Mn C, 2321 (1009, 5337); Mn W135, 62 (16, 238); and Mn Y, 561 (125, 2514) for control group and Pn 4, 6982 (4336, 11245); Pn 6B, 45 (6, 367); Pn 9V, 13219 (8773, 19917); Pn 14, 1580

(1281, 1950); Pn 18C, 1335 (409, 4361); Mn A, 1323 (666, 2629); Mn C, 2941 (2348, 3683); Mn W135, 3375 (1246, 9144); and Mn Y, 17527 (5413, 56744) for the conjugate Lot 11-041111BIa, assuming 3200 units/mL for each reference serum of each component PS. The conjugates induced 1-6982 folds more anti-PS specific antibody in mice as compared to the native PS control (Table 19). The immunogenicity of Pn 19F and 23F PS conjugate components by ELISA was not determined.

TABLE 19

The geometric mean anti-PS antibody levels[a] with 1 SD confidence interval of mouse groups (4-5 mice per group) two weeks post $3^{rd}$ immunization with 1 μg/dose each Pn and Mn PS in multi-valent conjugate Lot 11-041111BIa

| PS | Native PS mixture | Lot 11-041111BIa | Fold increase |
|---|---|---|---|
| 4 | 1 (1, 2) | 6982 (4336, 11245) | 6982 |
| 6B | 17 (7, 40) | 45 (6, 367) | 3 |
| 9V | 54 (13, 229) | 13219 (8773, 19917) | 245 |
| 14 | 7 (2, 14) | 1580 (1281, 1950) | 226 |
| 18C | 2 (1, 3) | 1335 (409, 4361) | 668 |
| A | 168 (111, 255) | 1323 (666, 2629) | 8 |
| C | 2321 (1009, 5337) | 2941 (2348, 3683) | 1 |
| W135 | 62 (16, 238) | 3375 (1246, 9144) | 54 |
| Y | 561 (125, 2514) | 17527 (5413, 56744) | 31 |

[a]Compared to a reference serum of each PS with an assigned anti-PS antibody level of 3200 units/mL.

Method B—Combined Synthesized Multivalent Pneumococcal (Pn) Serotypes 4, 6B, 9V, 14, 18C, 19F and 23F, and Meningococcal (Mn) Serogroups A, C, W135 and Y Polysaccharides-(Tetanus Toxoid+Bovine Thyroglobulin+Ovalbumin+Bovine Serum Albumin) Conjugate (Lot 11-041111BIb)

Activation of Mixture of Tetanus Toxoid, Bovine Thyroglobulin, Ovalbumin and Bovine Serum Albumin to Contain Hydrazide Groups 19. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.
20. After reacting for 4 hours, the pH of the reaction mixture was raised to 7.5-10 with 1 N NaOH to stop the reaction.
21. The reaction mixture was buffer-exchanged with 30 mM NaCl, 3 mM $Na_2CO_3$, pH about 10.5 at 4° C. using a 12-14 KDa dialysis membrane.

Activation of Pn 4, 6B, 9V, 14, 18C, 19F and 23F, and Mn A, C, W135 and Y PS Mixture to Contain Cyanate Groups 13. Pn 4, 6B, 9V, 14, 18C, 19F and 23F, and Mn A, C, W135 and Y PS mixture (0.1 mL; 0.909 mg/mL each PS) was activated with 8 uL CDAP (100 mg/mL in acetonitrile) for 2-2.5 minutes at 20-24° C. in the presence of 8 uL 0.2 M triethylamine.
14. The activated polysaccharide was mixed with 1.25 mL ice-cold 0.2 M HEPES, pH 7.5, 30 mM EDTA, and immediately used for conjugation.

Conjugation of Activated Pn 4, 6B, 9V, 14, 18C, 19F and 23F, and Mn A, C, W135 and Y PS Mixture to Activated Mixture of Tetanus Toxoid, Bovine Thyroglobulin, Ovalbumin and Bovine Serum Albumin 25. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.
26. Incubated the reaction mixture at 4° C. with gentle shaking for 3 overnights. (The prolonged incubation is to ensure decomposition of the residual left over unreacted cyanate groups.)
27. The solution was buffer-exchanged with saline, 10 mM HEPES, pH 7.5, 1 mM EDTA using a 12-14 KDa molecular weight cut-off membrane.
28. Volume of the dialyzed conjugate was determined, and the concentrations of the protein (TT+bovine thyroglobulin+ovalbumin+bovine serum albumin) and each polysaccharide (Pn 4, 6B, 9V, 14, 18C, 19F and 23F, and Mn A, C, W135 and Y) were calculated from the input masses.

Immunogenicity of Combined Synthesized Multi-Valent Conjugates Lots 11-041111BIb The conjugates were used to immunize groups of 4-5 mice with native polysaccharide mixture as a control at 1 μg/dose each Pn and Mn PS on days 0, 14 and 28. The geometric means of the induced antibody levels (units/mL) two weeks post $3^{rd}$ injection determined by ELISA are Pn 4, 1 (1, 2; 1 SD confidence interval), Pn 6B, 17 (7, 40); Pn 9V, 54 (13, 229); Pn 14, 7 (2, 14); Pn 18C, 2 (1, 3); Mn A, 168 (111, 255); Mn C, 2321 (1009, 5337); Mn W135, 62 (16, 238); and Mn Y, 561 (125, 2514) for control group and Pn 4, 3638 (1555, 8513); Pn 6B, 58 (4, 740); Pn 9V, 6206 (1171, 32902); Pn 14, 1558 (1414, 1717); Pn 18C, 94 (13, 680); Mn A, 284 (163, 496); Mn C, 1479 (820, 2668); Mn W135, 1533 (550, 4275); and Mn Y, 11840 (4409, 31797) for the conjugate Lot 11-041111BIb, assuming 3200 units/mL for the reference serum of each serogroup PS. The conjugates induced 1-3638 folds more anti-PS specific antibody in mice as compared to the native PS control (Table 20). The immunogenicity of Pn 19F and 23F PS conjugate components by ELISA was not determined.

TABLE 20

The geometric mean anti-PS antibody levels[a] with 1 SD confidence interval of mouse groups (4-5 mice per group) two weeks post $3^{rd}$ immunization with 1 μg/dose each Pn and Mn PS in multi-valent conjugate Lot 11-041111BIb

| PS | Native PS mixture | Lot 11-041111BIb | Fold increase |
|---|---|---|---|
| 4 | 1 (1, 2) | 3638 (1555, 8513) | 3638 |
| 6B | 17 (7, 40) | 58 (4, 740) | 3 |
| 9V | 54 (13, 229) | 6206 (1171, 32902) | 115 |
| 14 | 7 (2, 14) | 1558 (1414, 1717) | 223 |
| 18C | 2 (1, 3) | 94 (13, 680) | 47 |
| A | 168 (111, 255) | 284 (163, 496) | 2 |
| C | 2321 (1009, 5337) | 1479 (820, 2668) | 1 |
| W135 | 62 (16, 238) | 1533 (550, 4275) | 25 |
| Y | 561 (125, 2514) | 11840 (4409, 31797) | 21 |

[a]Compared to a reference serum of each PS with an assigned anti-PS antibody level of 3200 units/mL.

Method B—Combined Synthesized Multivalent Pneumococcal (Pn) Serotypes 4, 6B, 9V, 14, 18C, 19F and 23F, and Meningococcal (Mn) Serogroups A, C, W135 and Y, and *Haemophilus Influenzae* Type B (Hib) Polysaccharides-Tetanus Toxoid Conjugate Lot 12-041111BIIa Activation of TT to Contain Hydrazide Groups 22. Tetanus toxoid (4.2 mg/mL) was activated with 0.42 M hydrazine in the presence of 20 mM EDC, 0.1 M MES, pH 6.5 at 20-24° C.
23. After reacting for 4 hours, the pH of the reaction mixture was raised to 7.5-10 with 1 N NaOH to stop the reaction.
24. The reaction mixture was buffer-exchanged with 30 mM NaCl, 3 mM $Na_2CO_3$, pH about 10.5 at 4° C. using a 12-14 KDa dialysis membrane.

Activation of Pn 4, 6B, 9V, 14, 18C, 19F and 23F, and Mn A, C, W135 and Y, and Hib PS Mixture to Contain Cyanate Groups 15. Pn 4, 6B, 9V, 14, 18C, 19F and 23F, and Mn A, C, W135 and Y, and Hib PS mixture (0.1107 mL; 0.645 mg/mL each Pn and Mn PS, 1.936 mg/mL for Hib PS) was activated with 8 uL CDAP (100 mg/mL in acetonitrile) for 2-2.5 minutes at 20-24° C. in the presence of 8 uL 0.2 M triethylamine.

16. The activated polysaccharide was mixed with 1.25 mL ice-cold 0.2 M HEPES, pH 7.5, 30 mM EDTA, and immediately used for conjugation.

Conjugation of Activated Pn 4, 6B, 9V, 14, 18C, 19F and 23F, and Mn A, C, W135 and Y, and Hib PS Mixture to Activated TT 29. The activated polysaccharide mixture was combined with 0.5 mg activated TT (ice-cold, 0.15 mL, 3.4 mg/mL); vortex.

30. Incubated the reaction mixture at 4° C. with gentle shaking for 3 overnights. (The prolonged incubation is to ensure decomposition of the residual left over unreacted cyanate groups.)

31. The solution was buffer-exchanged with saline, 10 mM HEPES, pH 7.5, 1 mM EDTA using a 12-14 KDa molecular weight cut-off membrane.

32. Volume of the dialyzed conjugate was determined, and the concentrations of the protein (TT) and each polysaccharide (Pn 4, 6B, 9V, 14, 18C, 19F and 23F, and Mn A, C, W135 and Y, and Hib) were calculated from the input masses.

Immunogenicity of Combined Synthesized Multi-Valent Conjugates Lot 12-041111BIIa The conjugates were used to immunize groups of 4-5 mice with native polysaccharide mixture as a control at 1 μg/dose each Pn and Mn PS and 3 μg/dose Hib PS on days 0, 14 and 28. The geometric means of the induced antibody levels (units/mL) two weeks post $3^{rd}$ injection determined by ELISA are Pn 4, 16 (14, 18; 1 SD confidence interval), Pn 6B, 20 (14, 29); Pn 9V, 2 (1, 4); Pn 14, 6 (5, 10); Pn 18C, 8 (5, 11); Mn A, 544 (275, 1074); Mn C, 1339 (1065, 1682); Mn W135, 70 (26, 187); Mn Y, 416 (188, 919); and Hib 16 (12, 21) for control group and Pn 4, 18628 (13044, 26601); Pn 6B, 69 (9, 519); Pn 9V, 22955 (9626, 54738); Pn 14, 3067 (1755, 5363); Pn 18C, 2056 (829, 5100); Mn A, 9167 (7142, 11765); Mn C, 3790 (2523, 5694); Mn W135, 5981 (3450, 10371); Mn Y, 24301 (17356, 34025); and Hib 2325 (1348, 4012) for the conjugate Lot 12-041111BIIa, assuming 3200 units/mL for each reference serum of each component PS. The conjugates induced 2-11477 folds more anti-PS specific antibody in mice as compared to the native PS control (Table 21). The immunogenicity of Pn 19F and 23F PS conjugate components by ELISA was not determined.

TABLE 21

The geometric mean anti-PS antibody levels[a] with 1 SD confidence interval of mouse groups (4-5 mice per group) two weeks post $3^{rd}$ immunization with 1 μg/dose each Pn and Mn PS and 3 μg/dose Hib PS in multi-valent conjugate Lot 12-041111BIIa

| PS | Native PS mixture | Lot 12-041111BIIa | Fold increase |
|---|---|---|---|
| 4 | 16 (14, 18) | 18628 (13044, 26601) | 1164 |
| 6B | 20 (14, 29) | 69 (9, 519) | 3 |
| 9V | 2 (1, 4) | 22955 (9626, 54738) | 11477 |
| 14 | 6 (5, 10) | 3067 (1755, 5363) | 511 |
| 18C | 8 (5, 11) | 2056 (829, 5100) | 257 |
| A | 544 (275, 1074) | 9167 (7142, 11765) | 2 |
| C | 1339 (1065, 1682) | 3790 (2523, 5694) | 13 |
| W135 | 70 (26, 187) | 5981 (3450, 10371) | 5485 |
| Y | 416 (188, 919) | 24301 (17356, 34025) | 58 |
| Hib | 16 (12, 21) | 2325 (1348, 4012) | 145 |

[a]Compared to a reference serum of each PS with an assigned anti-PS antibody level of 3200 units/mL.

Method B—Combined Synthesized Multivalent Pneumococcal (Pn) Serotypes 4, 6B, 9V, 14, 18C, 19F and 23F, and Meningococcal (Mn) Serogroups A, C, W135 and Y, and Haemophilus Influenzae Type B (Hib) Polysaccharides-(Tetanus Toxoid+Bovine Thyroglobulin+Ovalbumin+Bovine Serum Albumin) Conjugate (Lot 12-041111BIIb)

Activation of Mixture of Tetanus Toxoid, Bovine Thyroglobulin, Ovalbumin and Bovine Serum Albumin to Contain Hydrazide Groups 25. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.

26. After reacting for 4 hours, the pH of the reaction mixture was raised to 7.5-10 with 1 N NaOH to stop the reaction.

27. The reaction mixture was buffer-exchanged with 30 mM NaCl, 3 mM $Na_2CO_3$, pH about 10.5 at 4° C. using a 12-14 KDa dialysis membrane.

Activation of Pn 4, 6B, 9V, 14, 18C, 19F and 23F, and Mn A, C, W135 and Y, and Hib PS Mixture to Contain Cyanate Groups 17. Pn 4, 6B, 9V, 14, 18C, 19F and 23F, and Mn A, C, W135 and Y, and Hib PS mixture (0.1107 mL; 0.645 mg/mL each Pn and Mn PS, 1.936 mg/mL for Hib PS) was activated with 8 uL CDAP (100 mg/mL in acetonitrile) for 2-2.5 minutes at 20-24° C. in the presence of 8 uL 0.2 M triethylamine.

18. The activated polysaccharide was mixed with 1.25 mL ice-cold 0.2 M HEPES, pH 7.5, 30 mM EDTA, and immediately used for conjugation.

Conjugation of Activated Pn 4, 6B, 9V, 14, 18C, 19F and 23F, and Mn A, C, W135 and Y, and Hib PS Mixture to Activated Mixture of Tetanus Toxoid, Bovine Thyroglobulin, Ovalbumin and Bovine Serum Albumin 33. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.

34. Incubated the reaction mixture at 4° C. with gentle shaking for 3 overnights. (The prolonged incubation is to ensure decomposition of the residual left over unreacted cyanate groups.)

35. The solution was buffer-exchanged with saline, 10 mM HEPES, pH 7.5, 1 mM EDTA using a 12-14 KDa molecular weight cut-off membrane.

36. Volume of the dialyzed conjugate was determined, and the concentrations of the protein (TT+bovine thyroglobulin+ovalbumin+bovine serum albumin) and each polysaccharide (Pn 4, 6B, 9V, 14, 18C, 19F and 23F, and Mn A, C, W135 and Y, and Hib) were calculated from the input masses.

Immunogenicity of Combined Synthesized Multi-Valent Conjugates Lots 12-041111BIIb The conjugates were used to immunize groups of 4-5 mice with native polysaccharide mixture as a control at 1 µg/dose Pn and Mn PS and 3 µg/dose Hib PS on days 0, 14 and 28. The geometric means of the induced antibody levels (units/mL) two weeks post $3^{rd}$ injection determined by ELISA are Pn 4, 16 (14, 18; 1 SD confidence interval), Pn 6B, 20 (14, 29); Pn 9V, 2 (1, 4); Pn 14, 6 (5, 10); Pn 18C, 8 (5, 11); Mn A, 544 (275, 1074); Mn C, 1339 (1065, 1682); Mn W135, 70 (26, 187); Mn Y, 416 (188, 919); and Hib 16 (12, 21) for control group and Pn 4, 18076 (12769, 25588); Pn 6B, 93 (4, 1948); Pn 9V, 18343 (8389, 40112); Pn 14, 4026 (3049, 5318); Pn 18C, 1623 (873, 3019); Mn A, 5696 (3098, 10473); Mn C, 1996 (892, 4467); Mn W135, 1683 (414, 6845); Mn Y, 15663 (6633, 36986); and Hib 3071 (1389, 6791) for the conjugate Lot 12-041111BIIb, assuming 3200 units/mL for the reference serum of each serogroup PS. The conjugates induced 1-9172 folds more anti-PS specific antibody in mice as compared to the native PS control (Table 22). The immunogenicity of Pn 19F and 23F PS conjugate components by ELISA was not determined.

TABLE 22

The geometric mean anti-PS antibody levels[a] with 1 SD confidence interval of mouse groups (4-5 mice per group) two weeks post $3^{rd}$ immunization with 1 µg/dose each Pn and Mn PS and 3 µg/dose Hib PS in multi-valent conjugate Lot 12-041111BIIb

| PS | Native PS mixture | Lot 12-041111BIIb | Fold increase |
|---|---|---|---|
| 4 | 16 (14, 18) | 18076 (12769, 25588) | 1130 |
| 6B | 20 (14, 29) | 93 (4, 1948) | 4 |
| 9V | 2 (1, 4) | 18343 (8389, 40112) | 9172 |
| 14 | 6 (5, 10) | 4026 (3049, 5318) | 671 |
| 18C | 8 (5, 11) | 1623 (873, 3019) | 203 |
| A | 544 (275, 1074) | 5696 (3098, 10473) | 10 |
| C | 1339 (1065, 1682) | 1996 (892, 4467) | 1 |
| W135 | 70 (26, 187) | 1683 (414, 6845) | 24 |
| Y | 416 (188, 919) | 15663 (6633, 36986) | 38 |
| Hib | 16 (12, 21) | 3071 (1389, 6791) | 192 |

[a]Compared to a reference serum of each PS with an assigned anti-PS antibody level of 3200 units/mL.

Method B—Combined Synthesized Multivalent Pneumococcal Serotypes 1, 3, 4, 5, 6B, 7F, 9V, 14, 18C, 19F and 23F Polysaccharides-Tetanus Toxoid Conjugate Lot 11-041111CIa Activation of TT to Contain Hydrazide Groups 28. Tetanus toxoid (4.2 mg/mL) was activated with 0.42 M hydrazine in the presence of 20 mM EDC, 0.1 M MES, pH 6.5 at 20-24° C.
29. After reacting for 4 hours, the pH of the reaction mixture was raised to 7.5-10 with 1 N NaOH to stop the reaction.
30. The reaction mixture was buffer-exchanged with 30 mM NaCl, 3 mM $Na_2CO_3$, pH about 10.5 at 4° C. using a 12-14 KDa dialysis membrane.

Activation of Pn 1, 3, 4, 5, 6B, 7F, 9V, 14, 18C, 19F and 23F PS Mixture to Contain Cyanate Groups 19. Pn 1, 3, 4, 5, 6B, 7F, 9V, 14, 18C, 19F and 23F mixture (0.1 mL; 0.909 mg/mL each PS) was activated with 8 uL CDAP (100 mg/mL in acetonitrile) for 2-2.5 minutes at 20-24° C. in the presence of 8 uL 0.2 M triethylamine.
20. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F PS Mixture to Activated TT 37. The activated polysaccharide was combined with 0.5 mg activated TT (ice-cold, 0.15 mL, 3.4 mg/mL); vortex.
38. Incubated the reaction mixture at 4° C. with gentle shaking for 3 overnights. (The prolonged incubation is to ensure decomposition of the residual left over unreacted cyanate groups.)
39. The solution was buffer-exchanged with saline, 10 mM HEPES, pH 7.5, 1 mM EDTA using a 12-14 KDa molecular weight cut-off membrane.
40. Volume of the dialyzed conjugate was determined, and the concentrations of the protein (TT) and each polysaccharide (Pn 1, 3, 4, 5, 6B, 7F, 9V, 14, 18C, 19F and 23F) were calculated from the input masses.

Immunogenicity of Combined Synthesized Multi-Valent Conjugates Lot 11-041111CIa

The conjugates were used to immunize groups of 4-5 mice with native polysaccharide mixture as a control at 1 µg/dose each Pn PS on days 0, 14 and 28. The geometric means of the induced antibody levels (units/mL) two weeks post $3^{rd}$ injection determined by ELISA are Pn 1, 213 (77, 586; 1 SD confidence interval); Pn 3, 22 (4, 126); Pn 4, 7 (5, 9); Pn 5, 7 (5, 10); Pn 6B, 6 (4, 8); Pn 7F, 15 (10, 22); Pn 9V, 2 (1, 4); Pn 14, 2 (0, 9); and Pn 18C, 1 (1, 1) for control group and Pn 1, 287 (123, 670); Pn 3, 6364 (4293, 9435); Pn 4, 5139 (3056, 8639); Pn 5, 464 (95, 2256); Pn 6B, 113 (4, 3123); Pn 7F, 5685 (1653, 19554); Pn 9V, 3665 (957, 14038); Pn 14, 1265 (830, 1929); and Pn 18C, 537 (152, 1896) for the conjugate Lot 11-041111CIa, assuming 3200 units/mL for the reference serum of each serogroup PS. The conjugates induced 1-1833 folds more anti-PS specific antibody in mice as compared to the native Pn PS control (Table 23). The immunogenicity of Pn 19F and 23F PS conjugate components by ELISA was not determined.

TABLE 23

The geometric mean anti-Pn PS antibody levels[a] with 1 SD confidence interval of mouse groups (4-5 mice per group) two weeks post $3^{rd}$ immunization with 1 µg/dose each Pn PS in multi-valent conjugate Lot 11-041111CIa

| Pn PS | Native PS mixture | Lot 11-041111CIa | Fold increase |
|---|---|---|---|
| 1 | 213 (77, 586) | 287 (123, 670) | 1 |
| 3 | 22 (4, 126) | 6364 (4293, 9435) | 289 |
| 4 | 7 (5, 9) | 5139 (3056, 8639) | 734 |
| 5 | 7 (5, 10) | 464 (95, 2256) | 66 |
| 6B | 6 (4, 8) | 113 (4, 3123) | 20 |
| 7F | 15 (10, 22) | 5685 (1653, 19554) | 379 |
| 9V | 2 (1, 4) | 3665 (957, 14038) | 1833 |
| 14 | 2 (0, 9) | 1265 (830, 1929) | 633 |
| 18C | 1 (1, 1) | 537 (152, 1896) | 537 |

[a]Compared to a reference serum of each PS with an assigned anti-PS antibody level of 3200 units/mL.

Method B—Combined Synthesized Multivalent Pneumococcal Serotypes 1, 3, 4, 5, 6B, 7F, 9V, 14, 18C, 19F and 23F Polysaccharides-(Tetanus Toxoid+Bovine Thyroglobulin+Ovalbumin+Bovine Serum Albumin) Conjugate (Lot 11-041111CIb)

Activation of Mixture of Tetanus Toxoid, Bovine Thyroglobulin, Ovalbumin and Bovine Serum Albumin to Contain Hydrazide Groups 31. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.

32. After reacting for 4 hours, the pH of the reaction mixture was raised to 7.5-10 with 1 N NaOH to stop the reaction.

33. The reaction mixture was buffer-exchanged with 30 mM NaCl, 3 mM $Na_2CO_3$, pH about 10.5 at 4° C. using a 12-14 KDa dialysis membrane.

Activation of Pn 1, 3, 4, 5, 6B, 7F, 9V, 14, 18C, 19F and 23F PS Mixture to Contain Cyanate Groups 21. Pn 1, 3, 4, 5, 6B, 7F, 9V, 14, 18C, 19F and 23F mixture (0.1 mL; 0.0909 mg/mL each PS) was activated with 8 uL CDAP (100 mg/mL in acetonitrile) for 2-2.5 minutes at 20-24° C. in the presence of 8 uL 0.2 M triethylamine.

22. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F PS Mixture to Activated Mixture of Tetanus Toxoid, Bovine Thyroglobulin, Ovalbumin and Bovine Serum Albumin 41. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.

42. Incubated the reaction mixture at 4° C. with gentle shaking for 3 overnights. (The prolonged incubation is to ensure decomposition of the residual left over unreacted cyanate groups.)

43. The solution was buffer-exchanged with saline, 10 mM HEPES, pH 7.5, 1 mM EDTA using a 12-14 KDa molecular weight cut-off membrane.

44. Volume of the dialyzed conjugate was determined, and the concentrations of the protein (TT+bovine thyroglobulin+ovalbumin+bovine serum albumin) and each polysaccharide (Pn 1, 3, 4, 5, 6B, 7F, 9V, 14, 18C, 19F and 23F) were calculated from the input masses.

Immunogenicity of Combined Synthesized Multi-Valent Conjugates Lot 11-041111CIb

The conjugates were used to immunize groups of 4-5 mice with native polysaccharide mixture as a control at 1 μg/dose each Pn PS on days 0, 14 and 28. The geometric means of the induced antibody levels (units/mL) two weeks post $3^{rd}$ injection determined by ELISA are Pn 1, 213 (77, 586; 1 SD confidence interval); Pn 3, 22 (4, 126); Pn 4, 7 (5, 9); Pn 5, 7 (5, 10); Pn 6B, 6 (4, 8); Pn 7F, 15 (10, 22); Pn 9V, 2 (1, 4); Pn 14, 2 (0, 9); and Pn 18C, 1 (1, 1) for control group and Pn 1, 249 (156, 399); Pn 3, 3871 (2683, 5584); Pn 4, 2580 (1770, 3762); Pn 5, 159 (28, 906); Pn 6B, 119 (11, 1284); Pn 7F, 1605 (72, 35604); Pn 9V, 3280 (512, 21016); Pn 14, 1510 (1136, 2006); and Pn 18C, 494 (75, 3234) for the conjugate Lot 11-041111CIb, assuming 3200 units/mL for the reference serum of each serogroup PS. The conjugates induced 1-1640 folds more anti-Pn PS specific antibody in mice as compared to the native Pn PS control (Table 24). The immunogenicity of Pn 19F and 23F PS conjugate components by ELISA was not determined.

TABLE 24

The geometric mean anti-Pn PS antibody levels[a] with 1 SD confidence interval of mouse groups (4-5 mice per group) two weeks post $3^{rd}$ immunization with 1 μg/dose each Pn PS in multi-valent conjugate Lot 11-041111CIb

| Pn PS | Native PS mixture | Lot 11-041111CIb | Fold increase |
|---|---|---|---|
| 1 | 213 (77, 586) | 249 (156, 399) | 1 |
| 3 | 22 (4, 126) | 3871 (2683, 5584) | 176 |
| 4 | 7 (5, 9) | 2580 (1770, 3762) | 369 |
| 5 | 7 (5, 10) | 159 (28, 906) | 23 |
| 6B | 6 (4, 8) | 119 (11, 1284) | 20 |
| 7F | 15 (10, 22) | 1605 (72, 35604) | 11 |
| 9V | 2 (1, 4) | 3280 (512, 21016) | 1640 |
| 14 | 2 (0, 9) | 1510 (1136, 2006) | 755 |
| 18C | 1 (1, 1) | 494 (75, 3234) | 494 |

[a]Compared to a reference serum of each PS with an assigned anti-PS antibody level of 3200 units/mL.

Method B—Combined Synthesized Multivalent Pneumococcal (Pn) Serotypes 1, 3, 4, 5, 6B, 7F, 9V, 14, 18C, 19F and 23F, and *Haemophilus Influenzae* Type B (Hib) Polysaccharides-Tetanus Toxoid Conjugate Lot 12-041111CIIa Activation of TT to Contain Hydrazide Groups 34. Tetanus toxoid (4.2 mg/mL) was activated with 0.42 M hydrazine in the presence of 20 mM EDC, 0.1 M MES, pH 6.5 at 20-24° C.

35. After reacting for 4 hours, the pH of the reaction mixture was raised to 7.5-10 with 1 N NaOH to stop the reaction.

36. The reaction mixture was buffer-exchanged with 30 mM NaCl, 3 mM $Na_2CO_3$, pH about 10.5 at 4° C. using a 12-14 KDa dialysis membrane.

Activation of Pn 1, 3, 4, 5, 6B, 7F, 9V, 14, 18C, 19F and 23F, and Hib PS Mixture to Contain Cyanate Groups 23. Pn 1, 3, 4, 5, 6B, 7F, 9V, 14, 18C, 19F and 23F, and Hib PS mixture (0.1107 mL; 0.645 mg/mL for each Pn PS and 1.936 mg/mL for Hib PS) was activated with 8 uL CDAP (100 mg/mL in acetonitrile) for 2-2.5 minutes at 20-24° C. in the presence of 8 uL 0.2 M triethylamine.

24. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F, and Hib PS Mixture to Activated TT 45. The activated polysaccharide was combined with 0.5 mg activated TT (ice-cold, 0.15 mL, 3.4 mg/mL); vortex.

46. Incubated the reaction mixture at 4° C. with gentle shaking for 3 overnights. (The prolonged incubation is to ensure decomposition of the residual left over unreacted cyanate groups.)

47. The solution was buffer-exchanged with saline, 10 mM HEPES, pH 7.5, 1 mM EDTA using a 12-14 KDa molecular weight cut-off membrane.

48. Volume of the dialyzed conjugate was determined, and the concentrations of the protein (TT) and each polysaccharide (Pn 1, 3, 4, 5, 6B, 7F, 9V, 14, 18C, 19F and 23F, and Hib) were calculated from the input masses.

Immunogenicity of Combined Synthesized Multi-Valent Conjugates Lot 12-041111CIIa The conjugates were used to immunize groups of 4-5 mice with native polysaccharide mixture as a control at 1 μg/dose each Pn PS and 3 μg/dose Hib PS on days 0, 14 and 28. The geometric means of the induced antibody levels (units/mL) two weeks post $3^{rd}$ injection determined by ELISA are Pn 1, 105 (32, 340; 1 SD confidence interval); Pn 3, 6 (1, 27); Pn 4, 14 (10, 21); Pn 5, 1 (1, 1); Pn 6B, 6 (4, 8); Pn 7F, 3 (2, 6); Pn 9V, 3 (1, 5); Pn 14, 4 (2, 8); Pn 18C, 3 (2, 6); and Hib 33 (24, 45) for control group and Pn 1, 249 (115, 540); Pn 3, 3778 (2230, 6400); Pn 4, 3104 (16161); Pn 5, 253 (25, 2553); Pn 6B, 168 (9, 3143); Pn 7F, 3074 (737, 12816); Pn 9V, 9906 (5485, 17890); Pn 14, 917 (643, 1306); Pn 18C, 864 (445, 1677); and Hib 1468 (354, 6076) for the conjugate Lot 12-041111CIIa, assuming 3200 units/mL for the reference serum of each serogroup PS. The conjugates induced 2-3302 folds more anti-PS specific antibody in mice as compared to the native PS control (Table 25). The immunogenicity of Pn 19F and 23F PS conjugate components by ELISA was not determined.

TABLE 25

The geometric mean anti-PS antibody levels[a] with 1 SD confidence interval of mouse groups (4-5 mice per group) two weeks post 3$^{rd}$ immunization with 1 μg/dose each Pn PS and 3 μg/dose Hib PS in multi-valent conjugate Lot 12-041111CIIa

| PS | Native PS mixture | Lot 12-041111CIIa | Fold increase |
|---|---|---|---|
| 1 | 105 (32, 340) | 249 (115, 540) | 2 |
| 3 | 6 (1, 27) | 3778 (2230, 6400) | 630 |
| 4 | 14 (10, 21) | 3104 (16161) | 222 |
| 5 | 1 (1, 1) | 253 (25, 2553) | 253 |
| 6B | 6 (4, 8) | 168 (9, 3143) | 28 |
| 7F | 3 (2, 6) | 3074 (737, 12816) | 1025 |
| 9V | 3 (1, 5) | 9906 (5485, 17890) | 3302 |
| 14 | 4 (2, 8) | 917 (643, 1306) | 229 |
| 18C | 3 (2, 6) | 864 (445, 1677) | 288 |
| Hib | 33 (24, 45) | 1468 (354, 6076) | 44 |

[a]Compared to a reference serum of each PS with an assigned anti-PS antibody level of 3200 units/mL.

Method B—Combined Synthesized Multivalent Pneumococcal (Pn) Serotypes 1, 3, 4, 5, 6B, 7F, 9V, 14, 18C, 19F and 23F, and *Haemophilus Influenzae* Type B (Hib) Polysaccharides-(Tetanus Toxoid+Bovine Thyroglobulin+Ovalbumin+Bovine Serum Albumin) Conjugate (Lot 12-041111CIIb)
Activation of Mixture of Tetanus Toxoid, Bovine Thyroglobulin, Ovalbumin and Bovine Serum Albumin to Contain Hydrazide Groups
- 37. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.
- 38. After reacting for 4 hours, the pH of the reaction mixture was raised to 7.5-10 with 1 N NaOH to stop the reaction.
- 39. The reaction mixture was buffer-exchanged with 30 mM NaCl, 3 mM Na$_2$CO$_3$, pH about 10.5 at 4° C. using a 12-14 KDa dialysis membrane.

Activation of Pn 1, 3, 4, 5, 6B, 7F, 9V, 14, 18C, 19F and 23F, and Hib PS Mixture to Contain Cyanate Groups
- 25. Pn 1, 3, 4, 5, 6B, 7F, 9V, 14, 18C, 19F and 23F, and Hib PS mixture (0.1107 mL; 0.645 mg/mL for each Pn PS and 1.936 mg/mL for Hib PS) was activated with 8 uL CDAP (100 mg/mL in acetonitrile) for 2-2.5 minutes at 20-24° C. in the presence of 8 uL 0.2 M triethylamine.
- 26. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F, and Hib PS Mixture to Activated Mixture of Tetanus Toxoid, Bovine Thyroglobulin, Ovalbumin and Bovine Serum Albumin
- 49. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.
- 50. Incubated the reaction mixture at 4° C. with gentle shaking for 3 overnights. (The prolonged incubation is to ensure decomposition of the residual left over unreacted cyanate groups.)
- 51. The solution was buffer-exchanged with saline, 10 mM HEPES, pH 7.5, 1 mM EDTA using a 12-14 KDa molecular weight cut-off membrane.
- 52. Volume of the dialyzed conjugate was determined, and the concentrations of the protein (TT+bovine thyroglobulin+ovalbumin+bovine serum albumin) and each polysaccharide (Pn 1, 3, 4, 5, 6B, 7F, 9V, 14, 18C, 19F and 23F, and Hib) were calculated from the input masses.

Immunogenicity of Combined Synthesized Multi-Valent Conjugates Lot 12-0411110CIIb The conjugates were used to immunize groups of 4-5 mice with native polysaccharide mixture as a control at 1 μg/dose each Pn PS and 3 μg/dose Hib PS on days 0, 14 and 28. The geometric means of the induced antibody levels (units/mL) two weeks post 3$^{rd}$ injection determined by ELISA are Pn 1, 105 (32, 340; 1 SD confidence interval); Pn 3, 6 (1, 27); Pn 4, 14 (10, 21); Pn 5, 1 (1, 1); Pn 6B, 6 (4, 8); Pn 7F, 3 (2, 6); Pn 9V, 3 (1, 5); Pn 14, 4 (2, 8); Pn 18C, 3 (2, 6); and Hib 33 (24, 45) for control group and Pn 1, 41 (10, 162); Pn 3, 3601 (1493, 8692); Pn 4, 7562 (4658, 12279); Pn 5, 175 (21, 1455); Pn 6B, 1269 (129, 12246); Pn 7F, 1269 (129, 12246); Pn 9V, 6469 (1816, 23050); Pn 14, 1009 (613, 1660); Pn 18C, 578 (123, 2707); and Hib 57 (1, 2364) for the conjugate Lot 12-0411110CIIb, assuming 3200 units/mL for the reference serum of each serogroup PS. The conjugates induced 1-2156 folds more anti-PS specific antibody in mice as compared to the native PS control (Table 26). The immunogenicity of Pn 19F and 23F PS conjugate components by ELISA was not determined.

TABLE 26

The geometric mean anti-PS antibody levels[a] with 1 SD confidence interval of mouse groups (4-5 mice per group) two weeks post 3$^{rd}$ immunization with 1 μg/dose each of Pn PS and 3 μg/dose of Hib PS in multi-valent conjugate Lot 12-041111CIIb

| PS | Native PS mixture | Lot 12-041111CIIb | Fold increase |
|---|---|---|---|
| 1 | 105 (32, 340) | 41 (10, 162) | 1 |
| 3 | 6 (1, 27) | 3601 (1493, 8692) | 300 |
| 4 | 14 (10, 21) | 7562 (4658, 12279) | 540 |
| 5 | 1 (1, 1) | 175 (21, 1455) | 175 |
| 6B | 6 (4, 8) | 47 (5, 426) | 8 |
| 7F | 3 (2, 6) | 1269 (129, 12246) | 423 |
| 9V | 3 (1, 5) | 6469 (1816, 23050) | 2156 |
| 14 | 4 (2, 8) | 1009 (613, 1660) | 252 |
| 18C | 3 (2, 6) | 578 (123, 2707) | 193 |
| Hib | 33 (24, 45) | 57 (1, 2364) | 2 |

[a]Compared to a reference serum of each PS with an assigned anti-PS antibody level of 3200 units/mL.

Method B—Combined Synthesized Multivalent Pneumococcal (Pn) Serotypes 1, 3, 4, 5, 6B, 7F, 9V, 14, 18C, 19F and 23F, and Meningococcal (Mn) Serogroups A, C, W135 and Y Polysaccharides-Tetanus Toxoid Conjugate Lot 15-041111DIa
Activation of TT to Contain Hydrazide Groups
- 40. Tetanus toxoid (4.2 mg/mL) was activated with 0.42 M hydrazine in the presence of 20 mM EDC, 0.1 M MES, pH 6.5 at 20-24° C.
- 41. After reacting for 4 hours, the pH of the reaction mixture was raised to 7.5-10 with 1 N NaOH to stop the reaction.

42. The reaction mixture was buffer-exchanged with 30 mM NaCl, 3 mM Na$_2$CO$_3$, pH about 10.5 at 4° C. using a 12-14 KDa dialysis membrane.

Activation of Pn 1, 3, 4, 5, 6B, 7F, 9V, 14, 18C, 19F and 23F, and Mn A, C, W135 and Y PS Mixture to Contain Cyanate Groups 27. Pn 1, 3, 4, 5, 6B, 7F, 9V, 14, 18C, 19F and 23F, and Mn A, C, W135 and Y PS mixture (0.1 mL; 0.667 mg/mL each PS) was activated with 8 uL CDAP (100 mg/mL in acetonitrile) for 2-2.5 minutes at 20-24° C. in the presence of 8 uL 0.2 M triethylamine.
28. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F, and Mn A, C, W135 and Y PS Mixture to Activated TT 53. The activated polysaccharide mixture was combined with 0.5 mg activated TT (ice-cold, 0.15 mL, 3.4 mg/mL); vortex.
54. Incubated the reaction mixture at 4° C. with gentle shaking for 3 overnights. (The prolonged incubation is to ensure decomposition of the residual left over unreacted cyanate groups.)
55. The solution was buffer-exchanged with saline, 10 mM HEPES, pH 7.5, 1 mM EDTA using a 12-14 KDa molecular weight cut-off membrane.
56. Volume of the dialyzed conjugate was determined, and the concentrations of the protein (TT) and each polysaccharide (Pn 1, 3, 4, 5, 6B, 7F, 9V, 14, 18C, 19F and 23F, and Mn A, C, W135 and Y) were calculated from the input masses.

Immunogenicity of Combined Synthesized Multi-Valent Conjugates Lot 15-041111DIa

The conjugates were used to immunize groups of 4-5 mice with native polysaccharide mixture as a control at 1 μg/dose each Pn and Mn PS on days 0, 14 and 28. The geometric means of the induced antibody levels (units/mL) two weeks post 3$^{rd}$ injection determined by ELISA are Pn 1, 58 (16, 213; 1 SD confidence interval); Pn 3, 8 (1, 53); Pn 4, 8 (3, 25); Pn 5, 7 (5, 9); Pn 6B, 4 (2, 8); Pn 7F, 4 (2, 8); Pn 9V, 5 (3, 10); Pn 14, 4 (2, 7); Pn 18C, 5 (4, 6); Mn A, 113 (35, 367); Mn C, 72 (17, 308); Mn W135, 30 (20, 47); and Mn Y, 253 (144, 445) for control group and Pn 1, 460 (314, 673); Pn 3, 5024 (3090, 8166); Pn 4, 10476 (6406, 17132); Pn 5, 86 (8, 917); Pn 6B, 361 (17, 7649); Pn 7F, 9276 (2953, 29133); Pn 9V, 8285 (3834, 17901); Pn 14, 1551 (1005, 2394); Pn 18C, 1895 (549, 6540); Mn A, 10625 (5635, 20037); Mn C, 3077 (1749, 5416); Mn W135, 13082 (8671, 19736); and Mn Y, 55308 (34432, 88842) for the conjugate Lot 15-041111DIa, assuming 3200 units/mL for each reference serum of each component PS. The conjugates induced 8-2319 folds more anti-PS specific antibody in mice as compared to the native PS control (Table 27). The immunogenicity of Pn 19F and 23F PS conjugate components by ELISA was not determined.

TABLE 27

The geometric mean anti-PS antibody levels[a] with 1 SD confidence interval of mouse groups (4-5 mice per group) two weeks post 3$^{rd}$ immunization with 1 μg/dose each Pn and Mn PS in multi-valent conjugate Lot 15-041111DIa

| PS | Native PS mixture | Lot 11-041111BIa | Fold increase |
| --- | --- | --- | --- |
| 1 | 58 (16, 213) | 460 (314, 673) | 8 |
| 3 | 8 (1, 53) | 5024 (3090, 8166) | 628 |
| 4 | 8 (3, 25) | 10476 (6406, 17132) | 1310 |
| 5 | 7 (5, 9) | 86 (8, 917) | 12 |
| 6B | 4 (2, 8) | 361 (17, 7649) | 90 |
| 7F | 4 (2, 8) | 9276 (2953, 29133) | 2319 |
| 9V | 5 (3, 10) | 8285 (3834, 17901) | 1657 |
| 14 | 4 (2, 7) | 1551 (1005, 2394) | 388 |
| 18C | 5 (4, 6) | 1895 (549, 6540) | 379 |
| A | 113 (35, 367) | 10625 (5635, 20037) | 94 |
| C | 72 (17, 308) | 3077 (1749, 5416) | 43 |
| W135 | 30 (20, 47) | 13082 (8671, 19736) | 436 |
| Y | 253 (144, 445) | 55308 (34432, 88842) | 219 |

[a]Compared to a reference serum of each PS with an assigned anti-PS antibody level of 3200 units/mL.

Method B—Combined Synthesized Multivalent Pneumococcal (Pn) Serotypes 1, 3, 4, 5, 6B, 7F, 9V, 14, 18C, 19F and 23F, and Meningococcal (Mn) Serogroups A, C, W135 and Y Polysaccharides-(Tetanus Toxoid+Bovine Thyroglobulin+Ovalbumin+Bovine Serum Albumin) Conjugate (Lot 15-041111DIb)

Activation of Mixture of Tetanus Toxoid, Bovine Thyroglobulin, Ovalbumin and Bovine Serum Albumin to Contain Hydrazide Groups 43. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.
44. After reacting for 4 hours, the pH of the reaction mixture was raised to 7.5-10 with 1 N NaOH to stop the reaction.
45. The reaction mixture was buffer-exchanged with 30 mM NaCl, 3 mM Na$_2$CO$_3$, pH about 10.5 at 4° C. using a 12-14 KDa dialysis membrane.

Activation of Pn 1, 3, 4, 5, 6B, 7F, 9V, 14, 18C, 19F and 23F, and Mn A, C, W135 and Y PS Mixture to Contain Cyanate Groups 29. Pn 1, 3, 4, 5, 6B, 7F, 9V, 14, 18C, 19F and 23F, and Mn A, C, W135 and Y PS mixture (0.1 mL; 0.667 mg/mL each PS) was activated with 8 uL CDAP (100 mg/mL in acetonitrile) for 2-2.5 minutes at 20-24° C. in the presence of 8 uL 0.2 M triethylamine.
30. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F, and Mn A, C, W135 and Y PS Mixture to Activated Mixture of Tetanus Toxoid, Bovine Thyroglobulin, Ovalbumin and Bovine Serum Albumin 57. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.
58. Incubated the reaction mixture at 4° C. with gentle shaking for 3 overnights. (The prolonged incubation is to ensure decomposition of the residual left over unreacted cyanate groups.)
59. The solution was buffer-exchanged with saline, 10 mM HEPES, pH 7.5, 1 mM EDTA using a 12-14 KDa molecular weight cut-off membrane.
60. Volume of the dialyzed conjugate was determined, and the concentrations of the protein (TT+bovine thyroglobulin+ovalbumin+bovine serum albumin) and each polysaccharide (Pn 1, 3, 4, 5, 6B, 7F, 9V, 14, 18C, 19F and 23F, and Mn A, C, W135 and Y) were calculated from the input masses.

Immunogenicity of Combined Synthesized Multi-Valent Conjugates Lots 15-041111DIb The conjugates were used to immunize groups of 4-5 mice with native polysaccharide mixture as a control at 1 µg/dose each Pn and Mn PS on days 0, 14 and 28. The geometric means of the induced antibody levels (units/mL) two weeks post $3^{rd}$ injection determined by ELISA are Pn 1, 58 (16, 213; 1 SD confidence interval); Pn 3, 8 (1, 53); Pn 4, 8 (3, 25); Pn 5, 7 (5, 9); Pn 6B, 4 (2, 8); Pn 7F, 4 (2, 8); Pn 9V, 5 (3, 10); Pn 14, 4 (2, 7); Pn 18C, 5 (4, 6); Mn A, 113 (35, 367); Mn C, 72 (17, 308); Mn W135, 30 (20, 47); and Mn Y, 253 (144, 445) for control group and Pn 1, 203 (114, 362); Pn 3, 1847 (1297, 2629); Pn 4, 5564 (2407, 12858); Pn 5, 29 (10, 82); Pn 6B, 25 (3, 199); Pn 7F, 1951 (598, 6359); Pn 9V, 1308 (665, 2574); Pn 14, 793 (605, 1041); Pn 18C, 121 (9, 1681); Mn A, 556 (159, 1946); Mn C, 549 (51, 5966); Mn W135, 86 (6, 1142); and Mn Y, 36690 (16621, 17843) for the conjugate Lot 15-041111DIb, assuming 3200 units/mL for the reference serum of each serogroup PS. The conjugates induced 3-696 folds more anti-PS specific antibody in mice as compared to the native PS control (Table 28). The immunogenicity of Pn 19F and 23F PS conjugate components by ELISA was not determined.

TABLE 28

The geometric mean anti-PS antibody levels[a] with 1 SD confidence interval of mouse groups (4-5 mice per group) two weeks post $3^{rd}$ immunization with 1 µg/dose each Pn and Mn PS in multi-valent conjugate Lot 15-041111DIb

| PS | Native PS mixture | Lot 15-041111DIb | Fold increase |
|---|---|---|---|
| 1 | 58 (16, 213) | 203 (114, 362) | 4 |
| 3 | 8 (1, 53) | 1847 (1297, 2629) | 231 |
| 4 | 8 (3, 25) | 5564 (2407, 12858) | 696 |
| 5 | 7 (5, 9) | 29 (10, 82) | 4 |
| 6B | 4 (2, 8) | 25 (3, 199) | 6 |
| 7F | 4 (2, 8) | 1951 (598, 6359) | 488 |
| 9V | 5 (3, 10) | 1308 (665, 2574) | 262 |
| 14 | 4 (2, 7) | 793 (605, 1041) | 198 |
| 18C | 5 (4, 6) | 121 (9, 1681) | 24 |
| A | 113 (35, 367) | 556 (159, 1946) | 5 |
| C | 72 (17, 308) | 549 (51, 5966) | 8 |
| W135 | 30 (20, 47) | 86 (6, 1142) | 3 |
| Y | 253 (144, 445) | 36690 (16621, 17843) | 145 |

[a]Compared to a reference serum of each PS with an assigned anti-PS antibody level of 3200 units/mL.

Method B—Combined Synthesized Multivalent Pneumococcal (Pn) Serotypes 1, 3, 4, 5, 6B, 7F, 9V, 14, 18C, 19F and 23F, and Meningococcal (Mn) Serogroups A, C, W135 and Y, and *Haemophilus Influenzae* Type B (Hib) Polysaccharides-Tetanus Toxoid Conjugate Lot 16-041111DIIa Activation of TT to Contain Hydrazide Groups
46. Tetanus toxoid (4.2 mg/mL) was activated with 0.42 M hydrazine in the presence of 20 mM EDC, 0.1 M MES, pH 6.5 at 20-24° C.
47. After reacting for 4 hours, the pH of the reaction mixture was raised to 7.5-10 with 1 N NaOH to stop the reaction.
48. The reaction mixture was buffer-exchanged with 30 mM NaCl, 3 mM $Na_2CO_3$, pH about 10.5 at 4° C. using a 12-14 KDa dialysis membrane.

Activation of Pn 1, 3, 4, 5, 6B, 7F, 9V, 14, 18C, 19F and 23F, and Mn A, C, W135 and Y, and Hib PS Mixture to Contain Cyanate Groups 31. Pn 1, 3, 4, 5, 6B, 7F, 9V, 14, 18C, 19F and 23F, and Mn A, C, W135 and Y, and Hib PS mixture (0.1219 mL; 0.513 mg/mL each Pn and Mn PS, 1.538 mg/mL for Hib PS) was activated with 8 uL CDAP (100 mg/mL in acetonitrile) for 2-2.5 minutes at 20-24° C. in the presence of 8 uL 0.2 M triethylamine.
32. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F, and Mn A, C, W135 and Y, and Hib PS Mixture to Activated TT
61. The activated polysaccharide mixture was combined with 0.5 mg activated TT (ice-cold, 0.15 mL, 3.4 mg/mL); vortex.
62. Incubated the reaction mixture at 4° C. with gentle shaking for 3 overnights. (The prolonged incubation is to ensure decomposition of the residual left over unreacted cyanate groups.)
63. The solution was buffer-exchanged with saline, 10 mM HEPES, pH 7.5, 1 mM EDTA using a 12-14 KDa molecular weight cut-off membrane.
64. Volume of the dialyzed conjugate was determined, and the concentrations of the protein (TT) and each polysaccharide (Pn 1, 3, 4, 5, 6B, 7F, 9V, 14, 18C, 19F and 23F, and Mn A, C, W135 and Y, and Hib) were calculated from the input masses.

Immunogenicity of Combined Synthesized Multi-Valent Conjugates Lot 16-041111DIIa The conjugates were used to immunize groups of 4-5 mice with native polysaccharide mixture as a control at 1 µg/dose each Pn and Mn PS and 3 µg/dose Hib PS on days 0, 14 and 28. The geometric means of the induced antibody levels (units/mL) two weeks post $3^{rd}$ injection determined by ELISA are Pn 1, 188 (67, 527; 1 SD confidence interval); Pn 3, 9 (3, 27); Pn 4, 19 (13, 27); Pn 5, 12 (9, 15); Pn 6B, 1 (1, 1); Pn 7F, 14 (10, 20); Pn 9V, 4 (3, 6); Pn 14, 3 (2, 4); Pn 18C, 5 (3, 9); Mn A, 114 (27, 474); Mn C, 278 (145, 536); Mn W135, 60 (35, 105); Mn Y, 157 (40, 617); and Hib 25 (25, 25) for control group and Pn 1, 386 (229, 651); Pn 3, 2003 (1089, 3685); Pn 4, 8000 (5741, 11147); Pn 5, 119 (41, 351); Pn 6B, 7 (0, 279); Pn 7F, 3810 (710, 20443); 9V, 2455 (855, 7050); Pn 14, 2833 (2149, 3734); Pn 18C, 1045 (272, 4024); Mn A, 5285 (2209, 12643); Mn C, 2210 (1091, 4479); Mn W135, 6146 (2165, 17446); Mn Y, 45788 (27363, 76619); and Hib 866 (247, 3036) for the conjugate Lot 16-041111DIIa, assuming 3200 units/mL for each reference serum of each component PS. The conjugates induced 2-944 folds more anti-PS specific antibody in mice as compared to the native PS control (Table 29). The immunogenicity of Pn 19F and 23F PS conjugate components by ELISA was not determined.

TABLE 29

The geometric mean anti-PS antibody levels[a] with 1 SD confidence interval of mouse groups (4-5 mice per group) two weeks post $3^{rd}$ immunization with 1 µg/dose each Pn and Mn PS and 3 µg/dose Hib PS in multi-valent conjugate Lot 16-041111DIIa

| PS | Native PS mixture | Lot 12-041111BIIa | Fold increase |
|---|---|---|---|
| 1 | 188 (67, 527) | 386 (229, 651) | 2 |
| 3 | 9 (3, 27) | 2003 (1089, 3685) | 223 |
| 4 | 19 (13, 27) | 8000 (5741, 11147) | 421 |
| 5 | 12 (9, 15) | 119 (41, 351) | 10 |
| 6B | 1 (1, 1) | 7 (0, 279) | 7 |
| 7F | 14 (10, 20) | 3810 (710, 20443) | 272 |
| 9V | 4 (3, 6) | 2455 (855, 7050) | 614 |
| 14 | 3 (2, 4) | 2833 (2149, 3734) | 944 |

TABLE 29-continued

The geometric mean anti-PS antibody levels[a] with 1 SD confidence interval of mouse groups (4-5 mice per group) two weeks post 3rd immunization with 1 μg/dose each Pn and Mn PS and 3 μg/dose Hib PS in multi-valent conjugate Lot 16-041111DIIa

| PS | Native PS mixture | Lot 12-041111BIIa | Fold increase |
|---|---|---|---|
| 18C | 5 (3, 9) | 1045 (272, 4024) | 209 |
| A | 114 (27, 474) | 5285 (2209, 12643) | 46 |
| C | 278 (145, 536) | 2210 (1091, 4479) | 8 |
| W135 | 60 (35, 105) | 6146 (2165, 17446) | 102 |
| Y | 157 (40, 617) | 45788 (27363, 76619) | 292 |
| Hib | 25 (25, 25) | 866 (247, 3036) | 35 |

[a]Compared to a reference serum of each PS with an assigned anti-PS antibody level of 3200 units/mL.

Method B—Combined Synthesized Multivalent Pneumococcal (Pn) Serotypes 1, 3, 4, 5, 6B, 7F, 9V, 14, 18C, 19F and 23F, and Meningococcal (Mn) Serogroups A, C, W135 and Y, and *Haemophilus Influenzae* Type B (Hib) Polysaccharides-(Tetanus Toxoid+Bovine Thyroglobulin+Ovalbumin+Bovine Serum Albumin) Conjugate (Lot 16-041111DIIb)

Activation of Mixture of Tetanus Toxoid, Bovine Thyroglobulin, Ovalbumin and Bovine Serum Albumin to Contain Hydrazide Groups 49. Mixture of (tetanus toxoid+bovine thyroglobulin+ovalbumin+bovine serum albumin, 1:1:1:1) (4.2 mg/mL) was activated with 0.42 M hydrazine in the presence of 20 mM EDC, 0.1 M MES, pH 6.5 at 20-24° C.

50. After reacting for 4 hours, the pH of the reaction mixture was raised to 7.5-10 with 1 N NaOH to stop the reaction.

51. The reaction mixture was buffer-exchanged with 30 mM NaCl, 3 mM $Na_2CO_3$, pH about 10.5 at 4° C. using a 12-14 KDa dialysis membrane.

Activation of Pn 1, 3, 4, 5, 6B, 7F, 9V, 14, 18C, 19F and 23F, and Mn A, C, W135 and Y, and Hib PS Mixture to Contain Cyanate Groups 33. Pn 1, 3, 4, 5, 6B, 7F, 9V, 14, 18C, 19F and 23F, and Mn A, C, W135 and Y, and Hib PS mixture (0.1219 mL; 0.513 mg/mL each Pn and Mn PS, 1.538 mg/mL for Hib PS) was activated with 8 uL CDAP (100 mg/mL in acetonitrile) for 2-2.5 minutes at 20-24° C. in the presence of 8 uL 0.2 M triethylamine.

34. The activated polysaccharide was mixed with 1.25 mL ice-cold 0.2 M HEPES, pH 7.5, 30 mM EDTA, and immediately used for conjugation.

Conjugation of Activated Pn 1, 3, 4, 5, 6B, 7F, 9V, 14, 18C, 19F and 23F, and Mn A, C, W135 and Y, and Hib PS Mixture to Activated Mixture of Tetanus Toxoid, Bovine Thyroglobulin, Ovalbumin and Bovine Serum Albumin 65. The activated polysaccharide was combined with 0.5 mg activated mixture of tetanus toxoid, bovine thyroglobulin, ovalbumin and bovine serum albumin (ice-cold, 0.15 mL, 3.4 mg/mL); vortex.

66. Incubated the reaction mixture at 4° C. with gentle shaking for 3 overnights. (The prolonged incubation is to ensure decomposition of the residual left over unreacted cyanate groups.)

67. The solution was buffer-exchanged with saline, 10 mM HEPES, pH 7.5, 1 mM EDTA using a 12-14 KDa molecular weight cut-off membrane.

68. Volume of the dialyzed conjugate was determined, and the concentrations of the protein (TT+bovine thyroglobulin+ovalbumin+bovine serum albumin) and each polysaccharide (Pn 1, 3, 4, 5, 6B, 7F, 9V, 14, 18C, 19F and 23F, and Mn A, C, W135 and Y, and Hib) were calculated from the input masses.

Immunogenicity of Combined Synthesized Multi-Valent Conjugates Lots 16-041111DIIb The conjugates were used to immunize groups of 4-5 mice with native polysaccharide mixture as a control at 1 μg/dose Pn and Mn PS and 3 μg/dose Hib PS on days 0, 14 and 28. The geometric means of the induced antibody levels (units/mL) two weeks post 3rd injection determined by ELISA are Pn 1, 188 (67, 527; 1 SD confidence interval); Pn 3, 9 (3, 27); Pn 4, 19 (13, 27); Pn 5, 12 (9, 15); Pn 6B, 1 (1, 1); Pn 7F, 14 (10, 20); Pn 9V, 4 (3, 6); Pn 14, 3 (2, 4); Pn 18C, 5 (3, 9); Mn A, 114 (27, 474); Mn C, 278 (145, 536); Mn W135, 60 (35, 105); Mn Y, 157 (40, 617); and Hib 25 (25, 25) for control group and Pn 1, 118 (25, 550); Pn 3, 2789 (1687, 4612); Pn 4, 6351 (3199, 12607); Pn 5, 91 (35, 237); Pn 6B, 10 (9, 19); Pn 7F, 3984 (1128, 14074); 9V, 2167 (755, 6229); Pn 14, 1471 (1054, 2051); Pn 18C, 207 (37, 1158); Mn A, 3501 (768, 15965); Mn C, 1679 (980, 2877); Mn W135, 923 (242, 3515); Mn Y, 17844 (8811, 36137); and Hib 823 (253, 2680) for the conjugate Lot 16-041111DIIb, assuming 3200 units/mL for the reference serum of each serogroup PS. The conjugates induced 1-542 folds more anti-Pn PS specific antibody in mice as compared to the native PS control (Table 30). The immunogenicity of Pn 19F and 23F PS conjugate components by ELISA was not determined.

TABLE 30

The geometric mean anti-PS antibody levels[a] with 1 SD confidence interval of mouse groups (4-5 mice per group) two weeks post 3rd immunization with 1 μg/dose each Pn and Mn PS and 3 μg/dose Hib PS in multi-valent conjugate Lot 16-041111DIIb

| PS | Native PS mixture | Lot 16-041111DIIb | Fold increase |
|---|---|---|---|
| 1 | 188 (67, 527) | 118 (25, 550) | 1 |
| 3 | 9 (3, 27) | 2789 (1687, 4612) | 310 |
| 4 | 19 (13, 27) | 6351 (3199, 12607) | 334 |
| 5 | 12 (9, 15) | 91 (35, 237) | 8 |
| 6B | 1 (1, 1) | 10 (9, 19) | 10 |
| 7F | 14 (10, 20) | 3984 (1128, 14074) | 285 |
| 9V | 4 (3, 6) | 2167 (755, 6229) | 542 |
| 14 | 3 (2, 4) | 1471 (1054, 2051) | 490 |
| 18C | 5 (3, 9) | 207 (37, 1158) | 41 |
| A | 114 (27, 474) | 3501 (768, 15965) | 31 |
| C | 278 (145, 536) | 1679 (980, 2877) | 6 |
| W135 | 60 (35, 105) | 923 (242, 3515) | 15 |
| Y | 157 (40, 617) | 17844 (8811, 36137) | 114 |
| Hib | 25 (25, 25) | 823 (253, 2680) | 33 |

[a]Compared to a reference serum of each PS with an assigned anti-PS antibody level of 3200 units/mL.

Method C—Combined Synthesized Multivalent Meningococcal (Mn) Groups A, C, W135 and Y, and *Haemophilus Influenzae* Type B (Hib) Polysaccharides-Tetanus Toxoid Conjugate Lot 7HM040716C3

Activation of TT to Contain Aldehyde Groups

6. Tetanus toxoid (4.2 mg/mL) was activated with 0.42 M 1-amino-2,3-propanediol (APDO) in the presence of 20 mM EDC, 0.1 M MES, pH 6.5 at 20-24° C.

7. After reacting for 4 hours, the pH of the reaction mixture was raised to 7.5-10 with 1 N NaOH to stop the reaction.

8. The reaction mixture was buffer-exchanged with 30 mM NaCl, 3 mM $Na_2CO_3$, pH about 10.5 at 4° C. using a 12-14 KDa dialysis membrane.

9. The degree of TT modification with APDO was determined by purpald assay [31] and Lowry assay [26].

10. Aliquot of TT-APDO was reacted with 6 mM $NaIO_4$ for 3 hour and then buffer exchanged with 30 mM NaCl, 3 mM $Na_2CO_3$, pH about 10.5.

Activation of Mn A, C, W135 and Y and Hib PS Mixture to Contain Hydrazide Groups 6. Mn A, C, W135 and Y PS mixture (0.05 mL; 1.429 mg/mL for each Mn PS and 4.286 mg/mL for Hib PS) was activated with 3 uL CDAP (100 mg/mL in acetonitrile) for 2-2.5 minutes at 20-24° C. in the presence of 5 uL 0.2 M triethylamine.
7. At the end of activation, 0.01 mL 5 M hydrazine, pH 7 was added and mixed.
8. The reaction mixture was incubated 4 hours at 20-24° C.
9. The sample was dialyzed against 10 mM HEPES, pH 7.5 at 4° C. using a 12-14 KDa dialysis membrane.
10. The volume of the activated PS mixture was determined (approximately 0.15 mL).

Conjugation of Activated Mn A, C, W135 and Y PS Mixture to Activated TT

7. Hydrazide-containing Mn A, C, W135 and Y, and Hib PS mixture (0.5 mg in 0.12 mL) was mixed with 0.03 mL 1 M HEPES, pH 7.5.
8. Aliquot of aldehyde-containing TT (0.5 mg; 0.137 mL 3.65 mg/mL) was added to the activated Mn A, C, W135 and Y PS mixture.
9. Incubate the reaction mixture at 20-24° C. for 18 hours.
10. The reaction mixture was treated with 5 uL 1 M $NaBH_4$ for 6 hours.
11. The solution was buffer-exchanged with saline, 10 mM HEPES, pH 7.5, 1 mM EDTA using a 12-14 KDa molecular weight cut-off membrane.
12. Volume of the dialyzed conjugate was determined, and the concentrations of the protein (TT) and each polysaccharide (Mn A, C, W135 and Y, and Hib) were calculated from the starting masses.

Immunogenicity of Combined Synthesized Multi-Valent Conjugate Lot 7HM040716C3

The conjugate was used to immunize groups of 10 mice with native polysaccharide as a control at 1 μg/dose each Mn PS and 3 μg/dose Hib PS on days 0, 14 and 28. The geometric means of the induced antibody levels (units/mL) two weeks post $3^{rd}$ injection determined by ELISA are Mn A, 24 (1, 442; 1 SD confidence interval), MnC, 711 (329, 1534); Mn W135, 2 (0, 14); Mn Y, 443 (216, 911); and Hib, 1 (1, 1) for control group and Mn A, 23277 (10031, 54011); Mn C, 20321 (12649, 32649); Mn W135, 25626 (16412, 40013); Mn Y, 83167 (37402, 184927); and Hib 173 (33, 896) for lot 7HM040716C3, assuming 3200 units/mL for the reference serum of each serogroup PS (Table 31). The conjugates induced 29-12813 folds more anti-PS specific antibody in mice as compared to the native PS control.

TABLE 31

The geometric mean anti-PS antibody levels[a] with 1 SD confidence interval of mouse groups (10 mice per group) two weeks post $3^{rd}$ immunization with 1 μg/dose each of Mn PS in multi-valent conjugate Lot 7HM040716C3

| PS | Native PS mixture | Lot 7HM040716C3 | Fold increase |
|---|---|---|---|
| A | 24 (1, 442) | 23277 (10031, 54011) | 970 |
| C | 711 (329, 1534) | 20321 (12649, 32649) | 29 |
| W135 | 2 (0, 14) | 25626 (16412, 40013) | 12813 |
| Y | 443 (216, 911) | 83167 (37402, 184927) | 188 |
| Hib | 1 (1, 1) | 173 (33, 896) | 173 |

[a]Compared to a reference serum of each PS with an assigned anti-PS antibody level of 3200 units/mL.

Method C—Combined Synthesized Multivalent Pneumococcal (Pn) Serotypes 1, 3, 4, 5, 6B, 7F, 9V, 14, 18C, 19F and 23F, and Meningococcal (Mn) Serogroups A, C, W135 and Y, and *Haemophilus Influenzae* Type B (Hib) Polysaccharides-Tetanus Toxoid Conjugate Lot 18HMP040716 C3

Activation of TT to Contain Aldehyde Groups

11. Tetanus toxoid (4.2 mg/mL) was activated with 0.42 M 1-amino-2,3-propanediol (APDO) in the presence of 20 mM EDC, 0.1 M MES, pH 6.5 at 20-24° C.
12. After reacting for 4 hours, the pH of the reaction mixture was raised to 7.5-10 with 1 N NaOH to stop the reaction.
13. The reaction mixture was buffer-exchanged with 30 mM NaCl, 3 mM $Na_2CO_3$, pH about 10.5 at 4° C. using a 12-14 KDa dialysis membrane.
14. The degree of TT modification with APDO was determined by purpald assay [31] and Lowry assay [26].
15. Aliquot of TT-APDO was reacted with 6 mM $NaIO_4$ for 3 hour and then buffer exchanged with 30 mM NaCl, 3 mM $Na_2CO_3$, pH about 10.5.

Activation of Pn 1, 3, 4, 6B, 7F, 9V, 14, 18C, 19F and 23F, and Mn A, C, W135 and Y, and Hib PS Mixture to Contain Hydrazide Groups 11. Pn 1, 3, 4, 6B, 7F, 9V, 14, 18C, 19F and 23F, and Mn A, C, W135 and Y, and Hib PS mixture (0.05 mL; 0.556 mg/mL for each Pn and Mn PS and 1.667 mg/mL for Hib PS) was activated with 3 uL CDAP (100 mg/mL in acetonitrile) for 2-2.5 minutes at 20-24° C. in the presence of 5 uL 0.2 M triethylamine.
12. At the end of activation, 0.01 mL 5 M hydrazine, pH 7 was added and mixed.
13. The reaction mixture was incubated 4 hours at 20-24° C.
14. The sample was dialyzed against 10 mM HEPES, pH 7.5 at 4° C. using a 12-14 KDa dialysis membrane.
15. The volume of the activated PS mixture was determined (approximately 0.15 mL).

Conjugation of Activated Pn 1, 3, 4, 5, 6B, 7F, 9V, 14, 18C, 19F and 23F, and Mn A, C, W135 and Y, and Hib PS Mixture to Activated TT 13. Hydrazide-containing Pn 1, 3, 4, 6B, 7F, 9V, 14, 18C, 19F and 23F, and Mn A, C, W135 and Y, and Hib PS mixture was mixed with 0.03 mL 1 M HEPES, pH 7.5.
14. Aliquot of aldehyde-containing TT (0.5 mg; 0.137 mL 3.65 mg/mL) was added to the activated Mn A, C, W135 and Y PS mixture.
15. Incubate the reaction mixture at 20-24° C. for 18 hours.
16. The reaction mixture was treated with 5 uL 1 M $NaBH_4$ for 6 hours.
17. An amount of 27.8 μg Pn 5 PS was added to the conjugate product.
18. The solution was buffer-exchanged with saline, 10 mM HEPES, pH 7.5, 1 mM EDTA using a 12-14 KDa molecular weight cut-off membrane.
19. Volume of the dialyzed conjugate was determined, and the concentrations of the protein (TT) and each polysaccharide (Pn 1, 3, 4, 5, 6B, 7F, 9V, 14, 18C, 19F and 23F, and Mn A, C, W135 and Y, and Hib) were calculated from the starting masses.

Immunogenicity of Combined Synthesized Multi-Valent Conjugates Lot 18HMP040716C3

The conjugates were used to immunize groups of 4-5 mice with native polysaccharide mixture as a control at 1 μg/dose each Pn and Mn PS and 3 μg/dose Hib PS on days 0, 14 and 28. The geometric means of the induced antibody levels (units/mL) two weeks post $3^{rd}$ injection determined by ELISA are Pn 1, 188 (67, 527; 1 SD confidence interval); Pn 3, 9 (3, 27); Pn 4, 19 (13, 27); Pn 5, 12 (9, 15); Pn 6B, 1 (1, 1); Pn 7F, 14 (10, 20); Pn 9V, 4 (3, 6); Pn 14, 3 (2, 4); Pn 18C, 5 (3, 9); Mn A, 114 (27, 474); Mn C, 278 (145, 536); Mn W135, 60 (35, 105); Mn Y, 157 (40, 617); and Hib 25 (25, 25) for control group and Pn 1, 3023 (1779, 5137); Pn 3, 3539 (721, 17360); Pn 4, 8030 (6742, 9565); Pn 5, 1 (1, 1); Pn 6B, 8199 (3038, 22126); Pn 7F, 1358 (91, 20235); 9V, 8344 (4480, 15541); Pn 14, 1682 (595, 4755); Pn 18C, 13002 (3102, 54501); Mn A, 27694 (14582, 52596); Mn C, 10525 (8544, 12965); Mn W135, 8966 (4502, 17855); Mn Y, 71435 (42736, 119408); and Hib 1446 (664, 3147) for the conjugate Lot 18HMP040716C3, assuming 3200 units/mL for each reference serum of each component PS. The conjugates induced 1-8199 folds more anti-PS specific antibody in mice as compared to the native PS control (Table 32). The immunogenicity of Pn 19F and 23F PS conjugate components by ELISA was not determined.

TABLE 32

The geometric mean anti-PS antibody levels$^a$ with 1 SD confidence interval of mouse groups (4-5 mice per group) two weeks post $3^{rd}$ immunization with 1 μg/dose each Pn and Mn PS and 3 μg/dose Hib PS in multi-valent conjugate Lot 18HMP040716C3

| PS | Native PS mixture | Lot 18HMP040716C3 | Fold increase |
|---|---|---|---|
| 1 | 188 (67, 527) | 3023 (1779, 5137) | 16 |
| 3 | 9 (3, 27) | 3539 (721, 17360) | 393 |
| 4 | 19 (13, 27) | 8030 (6742, 9565) | 423 |
| 5 | 12 (9, 15) | 1 (1, 1) | 1 |
| 6B | 1 (1, 1) | 8199 (3038, 22126) | 8199 |
| 7F | 14 (10, 20) | 1358 (91, 20235) | 100 |
| 9V | 4 (3, 6) | 8344 (4480, 15541) | 2086 |
| 14 | 3 (2, 4) | 1682 (595, 4755) | 561 |
| 18C | 5 (3, 9) | 13002 (3102, 54501) | 2600 |
| A | 114 (27, 474) | 27694 (14582, 52596) | 243 |
| C | 278 (145, 536) | 10525 (8544, 12965) | 38 |
| W135 | 60 (35, 105) | 8966 (4502, 17855) | 149 |
| Y | 157 (40, 617) | 71435 (42736, 119408) | 455 |
| Hib | 25 (25, 25) | 1446 (664, 3147) | 58 |

$^a$Compared to a reference serum of each PS with an assigned anti-PS antibody level of 3200 units/mL.

Method C—Combined Synthesized Multivalent Pneumococcal (Pn) Serotypes 1, 3, 4, 5, 6B, 7F, 9V, 14, 18C, 19F and 23F, and *Haemophilus Influenzae* Type B (Hib) Polysaccharides-Tetanus Toxoid Conjugate Lot 14HP040716C3

Activation of TT to Contain Aldehyde Groups
16. Tetanus toxoid (4.2 mg/mL) was activated with 0.42 M 1-amino-2,3-propanediol (APDO) in the presence of 20 mM EDC, 0.1 M MES, pH 6.5 at 20-24° C.
17. After reacting for 4 hours, the pH of the reaction mixture was raised to 7.5-10 with 1 N NaOH to stop the reaction.
18. The reaction mixture was buffer-exchanged with 30 mM NaCl, 3 mM Na$_2$CO$_3$, pH about 10.5 at 4° C. using a 12-14 KDa dialysis membrane.
19. The degree of TT modification with APDO was determined by purpald assay [31] and Lowry assay [26].
20. Aliquot of TT-APDO was reacted with 6 mM NaIO$_4$ for 3 hour and then buffer exchanged with 30 mM NaCl, 3 mM Na$_2$CO$_3$, pH about 10.5.

Activation of Pn 1, 3, 4, 6B, 7F, 9V, 14, 18C, 19F and 23F, and Hib PS Mixture to Contain Hydrazide Groups
16. Pn 1, 3, 4, 6B, 7F, 9V, 14, 18C, 19F and 23F, and Hib PS mixture (0.05 mL; 0.714 mg/mL for each Pn PS and 2.143 mg/mL for Hib PS) was activated with 3 uL CDAP (100 mg/mL in acetonitrile) for 2-2.5 minutes at 20-24° C. in the presence of 5 uL 0.2 M triethylamine.
17. At the end of activation, 0.01 mL 5 M hydrazine, pH 7 was added and mixed.
18. The reaction mixture was incubated 4 hours at 20-24° C.
19. The sample was dialyzed against 10 mM HEPES, pH 7.5 at 4° C. using a 12-14 KDa dialysis membrane.
20. The volume of the activated PS mixture was determined (approximately 0.15 mL).

Conjugation of Activated Pn 1, 3, 4, 5, 6B, 7F, 9V, 14, 18C, 19F and 23F, and Hib PS Mixture to Activated TT
20. Hydrazide-containing Pn 1, 3, 4, 6B, 7F, 9V, 14, 18C, 19F and 23F, and Hib PS mixture was mixed with 0.03 mL 1 M HEPES, pH 7.5.
21. Aliquot of aldehyde-containing TT (0.5 mg; 0.137 mL 3.65 mg/mL) was added to the activated Mn A, C, W135 and Y PS mixture.
22. Incubate the reaction mixture at 20-24° C. for 18 hours.
23. The reaction mixture was treated with 5 uL 1 M NaBH$_4$ for 6 hours.
24. An amount of 35.7 μg Pn 5 PS was added to the conjugate product.
25. The solution was buffer-exchanged with saline, 10 mM HEPES, pH 7.5, 1 mM EDTA using a 12-14 KDa molecular weight cut-off membrane.
26. Volume of the dialyzed conjugate was determined, and the concentrations of the protein (TT) and each polysaccharide (Pn 1, 3, 4, 5, 6B, 7F, 9V, 14, 18C, 19F and 23F, and Hib) were calculated from the starting masses.

Immunogenicity of Combined Synthesized Multi-Valent Conjugates Lot 14HP040716C3

The conjugates were used to immunize groups of 4-5 mice with native polysaccharide mixture as a control at 1 μg/dose each Pn PS and 3 μg/dose Hib PS on days 0, 14 and 28. The geometric means of the induced antibody levels (units/mL) two weeks post $3^{rd}$ injection determined by ELISA are Pn 1, 105 (32, 340; 1 SD confidence interval); Pn 3, 6 (1, 27); Pn 4, 14 (10, 21); Pn 5, 1 (1, 1); Pn 6B, 6 (4, 8); Pn 7F, 3 (2, 6); Pn 9V, 3 (1, 5); Pn 14, 4 (2, 8); Pn 18C, 3 (2, 6); and Hib 33 (24, 45) for control group and Pn 1, 6603 (2428, 17954); Pn 3, 5213 (3355, 8100); Pn 4, 8288 (5802, 11839); Pn 5, 10 (0, 231); Pn 6B, 5202 (520, 52067); Pn 7F, 7088 (1755, 28618); 9V, 6434 (2472, 16743); Pn 14, 1834 (912, 3686); Pn 18C, 3327 (11829); and Hib 333 (37, 3019) for the conjugate Lot 14HP040716C3, assuming 3200 units/mL for each reference serum of each component PS. The conjugates induced 10-2363 folds more anti-PS specific antibody in mice as compared to the native PS control (Table 33). The immunogenicity of Pn 19F and 23F PS conjugate components by ELISA was not determined.

TABLE 33

The geometric mean anti-PS antibody levels$^a$ with 1 SD confidence interval of mouse groups (4-5 mice per group) two weeks post $3^{rd}$ immunization with 1 μg/dose each Pn PS and 3 μg/dose Hib PS in multi-valent conjugate Lot 14HP040716C3

| PS | Native PS mixture | Lot 14HP040716C3 | Fold increase |
|---|---|---|---|
| 1 | 105 (32, 340) | 6603 (2428, 17954) | 63 |
| 3 | 6 (1, 27) | 5213 (3355, 8100) | 869 |
| 4 | 14 (10, 21) | 8288 (5802, 11839) | 592 |
| 5 | 1 (1, 1) | 10 (0, 231) | 10 |
| 6B | 6 (4, 8) | 5202 (520, 52067) | 867 |
| 7F | 3 (2, 6) | 7088 (1755, 28618) | 2363 |
| 9V | 3 (1, 5) | 6434 (2472, 16743) | 1609 |
| 14 | 4 (2, 8) | 1834 (912, 3686) | 459 |
| 18C | 3 (2, 6) | 3327 (11829) | 1109 |
| Hib | 33 (24, 45) | 333 (37, 3019) | 10 |

$^a$Compared to a reference serum of each PS with an assigned anti-PS antibody level of 3200 units/mL.

Method C—Combined Synthesized Multivalent Pneumococcal (Pn) Serotypes 1, 3, 4, 5, 6B, 7F, 9V, 14, 18C, 19F and 23F Polysaccharides-Tetanus Toxoid Conjugate Lot 11Pn040716C3

Activation of TT to Contain Aldehyde Groups
- 21. Tetanus toxoid (4.2 mg/mL) was activated with 0.42 M 1-amino-2,3-propanediol (APDO) in the presence of 20 mM EDC, 0.1 M MES, pH 6.5 at 20-24° C.
- 22. After reacting for 4 hours, the pH of the reaction mixture was raised to 7.5-10 with 1 N NaOH to stop the reaction.
- 23. The reaction mixture was buffer-exchanged with 30 mM NaCl, 3 mM $Na_2CO_3$, pH about 10.5 at 4° C. using a 12-14 KDa dialysis membrane.
- 24. The degree of TT modification with APDO was determined by purpald assay [31] and Lowry assay [26].
- 25. Aliquot of TT-APDO was reacted with 6 mM $NaIO_4$ for 3 hour and then buffer exchanged with 30 mM NaCl, 3 mM $Na_2CO_3$, pH about 10.5.

Activation of Pn 1, 3, 4, 6B, 7F, 9V, 14, 18C, 19F and 23F PS Mixture to Contain Hydrazide Groups
- 21. Pn 1, 3, 4, 6B, 7F, 9V, 14, 18C, 19F and 23F PS mixture (0.05 mL; 0.909 mg/mL for each PS) was activated with 3 uL CDAP (100 mg/mL in acetonitrile) for 2-2.5 minutes at 20-24° C. in the presence of 5 uL 0.2 M triethylamine.
- 22. At the end of activation, 0.01 mL 5 M hydrazine, pH 7 was added and mixed.
- 23. The reaction mixture was incubated 4 hours at 20-24° C.
- 24. The sample was dialyzed against 10 mM HEPES, pH 7.5 at 4° C. using a 12-14 KDa dialysis membrane.
- 25. The volume of the activated PS mixture was determined (approximately 0.15 mL).

Conjugation of Activated Pn 1, 3, 4, 5, 6B, 7F, 9V, 14, 18C, 19F and 23F PS Mixture to Activated TT
- 27. Hydrazide-containing Pn 1, 3, 4, 6B, 7F, 9V, 14, 18C, 19F and 23F PS mixture was mixed with 0.03 mL 1 M HEPES, pH 7.5.
- 28. Aliquot of aldehyde-containing TT (0.5 mg; 0.137 mL 3.65 mg/mL) was added to the activated MnA, C, W135 and Y PS mixture.
- 29. Incubate the reaction mixture at 20-24° C. for 18 hours.
- 30. The reaction mixture was treated with 5 uL 1 M $NaBH_4$ for 6 hours.
- 31. An amount of 45.5 μg Pn 5 PS was added to the conjugate product.
- 32. The solution was buffer-exchanged with saline, 10 mM HEPES, pH 7.5, 1 mM EDTA using a 12-14 KDa molecular weight cut-off membrane.
- 33. Volume of the dialyzed conjugate was determined, and the concentrations of the protein (TT) and each polysaccharide (Pn 1, 3, 4, 5, 6B, 7F, 9V, 14, 18C, 19F and 23F) were calculated from the starting masses.

Immunogenicity of Combined Synthesized Multi-Valent Conjugates Lot 11Pn040716C3

The conjugates were used to immunize groups of 4-5 mice with native polysaccharide mixture as a control at 1 μg/dose each Pn PS on days 0, 14 and 28. The geometric means of the induced antibody levels (units/mL) two weeks post $3^{rd}$ injection determined by ELISA are Pn 1, 213 (77, 586; 1 SD confidence interval); Pn 3, 22 (4, 126); Pn 4, 7 (5, 9); Pn 5, 7 (5, 10); Pn 6B, 6 (4, 8); Pn 7F, 15 (10, 22); Pn 9V, 2 (1, 4); Pn 14, 2 (0, 9); and Pn 18C, 1 (1, 1) for control group and Pn 1, 3292 (2754, 3935); Pn 3, 1982 (1093, 3594); Pn 4, 15677 (6557, 37482); Pn 5, 3 (0, 47); Pn 6B, 450 (22, 9354); Pn 7F, 1646 (110, 24529); 9V, 1516 (307, 7492); Pn 14, 2031 (1317, 3134); and Pn 18C, 825 (66, 10240) for the conjugate Lot 11Pn040716C3, assuming 3200 units/mL for each reference serum of each component PS. The conjugates induced 1-2204 folds more anti-PS specific antibody in mice as compared to the native PS control (Table 34). The immunogenicity of Pn 19F and 23F PS conjugate components by ELISA was not determined.

TABLE 34

The geometric mean anti-Pn PS antibody levels[a] with 1 SD confidence interval of mouse groups (4-5 mice per group) two weeks post $3^{rd}$ immunization with 1 μg/dose each Pn and Mn PS and 3 μg/dose Hib PS in multi-valent conjugate Lot 11Pn040716C3

| PS | Native PS mixture | Lot 11Pn040716C3 | Fold increase |
|---|---|---|---|
| 1 | 213 (77, 586) | 3292 (2754, 3935) | 15 |
| 3 | 22 (4, 126) | 1982 (1093, 3594) | 90 |
| 4 | 7 (5, 9) | 15677 (6557, 37482) | 2240 |
| 5 | 7 (5, 10) | 3 (0, 47) | 1 |
| 6B | 6 (4, 8) | 450 (22, 9354) | 75 |
| 7F | 15 (10, 22) | 1646 (110, 24529) | 110 |
| 9V | 2 (1, 4) | 1516 (307, 7492) | 758 |
| 14 | 2 (0, 9) | 2031 (1317, 3134) | 1016 |
| 18C | 1 (1, 1) | 825 (66, 10240) | 825 |

[a]Compared to a reference serum of each PS with an assigned anti-PS antibody level of 3200 units/mL.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

1. Avery O T, Goebel W F. Chemo-immunological studies on conjugated carbohydrates. II. Immunological specificity of synthetic sugar-proteins. J Exp Med 1929; 50:533-550.
2. Schneerson R, Barrera O, Sutton A, Robbins J B. Preparation, characterization, and immunogenicity of *Haemophilus influenzae* type b polysaccharide protein conjugates. J Exp Med 1980; 152:361-376.
3. Anderson P. Antibody responses to *Haemophilus influenzae* type b and diphtheria toxin induced by conjugation of oligosaccharides of the type b capsule with the nontoxic protein $CRM_{197}$. Infect Immun 1983, 39:233-238.
4. Marburg S, Jorn D. Tolman R L, et al. Bimolecular chemistry of macromolecules: synthesis of bacterial polysaccharide conjugates with *Neisseria meningitidis* membrane protein. J Amer Chem Soc 1986; 108:5282-5287.
5. Kniskern P J, Marburg S. Conjugation: design, chemistry, and analysis. In: Ellis R W, Granoff D M, editors. Development and clinical uses of *Haemophilus* b conjugate vaccines. New York: Marcel Dekker, 1994: 37-69.
6. Chu C, Schneerson R, Robbins J B, Rastogi S C. Further studies on the immunogenicity of *Haemophilus influenzae* type b and pneumococcal type 6B polysaccharide-protein conjugates. Infect Immun 1983; 40:245-256.
7. Schneerson R, Robbins J B, Parke J C, Bell C, Schlesselman J J, Sutton A, Wang Z, Schiffman G, Karpas, A. Shiloach J. Quantitative analysis of serum antibodies elicited in adults by *Haemophilus influenzae* type b and pneumococcus type 6A capsular polysaccharide-tetanus toxoid conjugates. Inect Immun 1986, 52:519-528.
8. Anderson P W, Pichichero M E, Stein E C, Porcelli S, Betts R F, Connuck D M, Korones D, Insel R A, Zahradnik J M, Eby R. Effect of oligosaccharide chain length, exposed terminal group, and hapten loading on the antibody response of human adults and infants to vaccines consisting of *Haemophilus influenzae* type b capsular antigen unterminally coupled to the diphtheria protein CRM197. J. Immunol. 1989; 142:2464-8.

9. Jennings H J, Lugowski C. Immunochemistry of groups A, B, and C meningococcal polysaccharide-tetanus toxoid conjugates. J Immunol 1981; 127:1011-8.
10. Beuvery E C, Roy R, Kanhai V et al. Characteristics of two types of meningococcal group C polysaccharide conjugates using tetanus toxoid as protein carrier protein. Dev Biol Stand 1986; 65:197-204.
11. Beuvery E C, Rossum F V, Nagel J. Comparison of the induction of immunoglobulin M and G antibodies in mice with purified pneumococcal type 3 and meningococcal group C polysaccharides and their protein conjugates. Infect Immun 1982; 37:15-22.
12. Beuvery E C, Delft R V, Miedema F et al. Immunological evaluation of meningococcal group C polysaccharide-tetanus toxoid conjugate in mice. Infect Immun 1983; 41:609-17.
13. Costantino P, Viti S, Podda A et al. Development and phase 1 clinical testing of a conjugate vaccine against meningococcus A and C. Vaccine 1992; 10:691-8.
14. Richmond P, Borrow R, Miller E et al. Meningococcal serogroup C conjugate vaccine is immunogenic in infancy and primes for memory. J Infect Dis 1999; 179:1569-72.
15. Richmond P, Borrow R, Findlow J et al. Evaluation of de-O-acetylated meningococcal C polysaccharide-tetanus toxoid conjugate vaccine in infancy: Reactogenicity, immunogenicity, immunologic priming, and bactericidal activity against O-acetylated and de-O-acetylated serogroup C strains Infect Immun 2001; 69:2378-82.
16. Beuvery E C, Miedema F, Delft R V et al. Preparation and Immunochemical characterization of meningococcal group C polysaccharide-tetanus toxoid conjugates as a new generation of vaccines. Infect Immun 1983; 40:39-45.
17. Beuvery E C, Miedema F, Delft R V et al. Vaccine potential of meningococcal group C polysaccharide-tetanus toxoid conjugate. J Infect 1983; 6:247-55.
18. Guo Z, Jennings H. Protein-polysaccharide conjugation. In: Pollard A J, Maiden MC (eds) Methods in Molecular Medicine, vol 66: Meningococcal Vaccines: methods and Protocols, Humana Press, Totowa, N.J., 2001, pg 49-54.
19. Inman J K, Dintzis H M. The derivatization of crosslinked polyacrylamide beads. Controlled introduction of functional groups for the preparation of special-purpose, biochemical adsorbents. Biochemistry 1969; 8:4074-4082.
20. Shafer D E, Toll B, Schuman R F, Nelson B L, Mond J J, Lees A. Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides. Vaccine 2000; 18(13): 1273-1281
21. King T P, Zhao S W, Lam T. Preparation of protein conjugates via intermolecular hydrazone linkage. Biochemistry 1986; 25:5774-5779.
22. U.S. Pat. No. 5,651,971
23. U.S. Pat. No. 5,965,714
24. WO Patent 02058737
25. WO Patent 03007985
26. Pierce Catalog 2003-2004, page 306.
27. Monsigny M, Petit C and Roche A C. Colorimetric determination of neutral sugars by a resorcinol sulfuric acid micromethod. Anal. Biochem. 1988; 175:525-530.
28. WO Patent 00004922
29. Kohn J and Wilchek M. The use of cyanogens bromide and other cyanylating agents for the activation of polysaccharide resins. Applied Biochem. Biotechonol. 1984; 9:285-305.
30. Carey R B, Eisenstein T K, Shockman G D, Greber T F and Swenson R M. Soluble group- and type-specific antigens from type III group B *Streptococcus*. Infection and Immunity 1980; 28:195-203.
31. Lee C H and Frasch C E. Quantification of bacterial polysaccharides by the purpald assay: Measurement of periodate-generated formaldehyde from glycol in the repeating unit. Anal. Biochem. 2001; 296:73-82.
32. Keleti G and Lederer W H. Handbook of micromethods for the biological sciences. 61. Hexoses (Anthrone). Page 73. Van Nostrand Reinhold Co., New York, 1974.
33. Keleti G and Lederer W H. Handbook of micromethods for the biological sciences. 70. Phosphorus (Total). Page 84. Van Nostrand Reinhold Co., New York, 1974.
34. Vidal J. Trinitrophenyl-protein conjugates are more complex than it is currently thought. J. Immunol. Methods 1986; 86:155-156.
35. Pierce Catalog 2003-2004, pages 241 and 305.
36. WO Patent 2005/014037 A2

What is claimed is:

1. A method for making a complex multivalent immunogenic conjugate, comprising:
    reacting a plurality of immunogenic-distinct polysaccharides with a cyanylation agent resulting in a mixture of a plurality of cyanate-activated immunogenic-distinct polysaccharides;
    reacting at least one protein with hydrazine, carbohydrazide, hydrazine dichloride, a dihydrazide, or a mixture thereof under conditions sufficient to produce a solution of at least one hydrazide-activated protein; and
    contacting the mixture of the plurality of cyanate-activated immunogenic-distinct polysaccharides with the at least one hydrazide-activated protein at a pH of about 6 to about 8 such that the plurality of cyanate-activated immunogenic-distinct polysaccharides simultaneously react with the at least one hydrazide-activated protein resulting in a complex multivalent immunogenic conjugate that includes at least one C—N bond formed between each attached immunogenic-distinct polysaccharide and the protein.

2. The method of claim 1, wherein the cyanylation agent is selected from 1-cyano-4-dimethylammoniumpyridinium tetrafluoroborate, cyanogen bromide, or N-cyano-N,N,N-triethylammonium tetrafluoroborate.

3. The method of claim 1, wherein the simultaneous reaction of the plurality of cyanate-activated immunogenic-distinct polysaccharides with the at least one hydrazide-activated protein is effected in a composition that includes the mixture of the plurality of cyanate-activated immunogenic-distinct polysaccharides and the at least one hydrazide-activated protein.

4. The method of claim 1, wherein the contacting of the mixture of the plurality of cyanate-activated immunogenic-distinct polysaccharides with the at least one hydrazide-activated protein comprises preparing a reaction composition that includes the mixture of the plurality of cyanate-activated immunogenic-distinct polysaccharides with the at least one hydrazide-activated protein.

5. The method of claim 1, further comprising reacting a second plurality of second immunogenic-distinct polysaccharides with a cyanylation agent resulting in a second mixture of a plurality of second cyanate-activated immunogenic-distinct polysaccharides; and
    contacting the second mixture of a plurality of cyanate-activated immunogenic-distinct polysaccharides with the complex multivalent immunogenic conjugate to form at least one C—N bond between each second cyanate-activated immunogenic-distinct polysaccharide and the protein.

6. The method of claim 5, wherein the reactivity of the second immunogenic-distinct polysaccharides with the cyanylation agent is greater than the reactivity of the first immunogenic-distinct polysaccharides with the cyanylation agent.

7. The method of claim 6, wherein the first immunogenic-distinct polysaccharide is selected from at least one of Meningococcal group A or Meningococcal group C.

8. The method of claim 6, wherein the second immunogenic-distinct polysaccharide is selected from at least one of Meningococcal group W135 or Meningococcal group Y.

9. A complex multivalent immunogenic conjugate prepared according to claim 1.

10. A pharmaceutical composition comprising the complex multivalent immunogenic conjugate of claim 9 and at least one pharmaceutically-acceptable carrier.

11. The method of claim 1, wherein the plurality of immunogenic-distinct polysaccharides includes at least one pneumococcal polysaccharide, at least one meningococcal polysaccharide, and at least one *Haemophilus influenzae* type b polysaccharide.

12. The method of claim 1, wherein the at least one hydrazide-activated protein is soluble at neutral pH.

13. The method of claim 12, wherein the at least one protein is reacted with hydrazine, carbohydrazide, hydrazine chloride, a dihydrazide or a mixture thereof in the presence of (i) a carbodiimide and (ii) at least one amino acid, at least one peptide, or a mixture of at least one amino acid and at least one peptide.

14. The method of claim 13, wherein the amino acid is selected from at least one of lysine, arginine, histidine, glycine, serine, threonine, glutamic acid or cysteine.

15. The method of claim 1, wherein the at least one protein is reacted with hydrazine, carbohydrazide, succinyl dihydrazide, adipic acid dihydrazide or a mixture thereof in the presence of a carbodiimide hydrochloride at a pH of 6 to 7 to obtain a solution of hydrazide-activated protein, and further comprising buffer exchanging the solution of hydrazide-activated protein to a pH of from 10.0 to 11.0.

16. The method of claim 1, wherein the at least one protein is reacted with hydrazine, carbohydrazide, succinyl dihydrazide, adipic acid dihydrazide or a mixture thereof in the presence of a carbodiimide hydrochloride at a pH of 5.5 to 6.5 to obtain a solution of hydrazide-activated protein, and further comprising buffer exchanging the solution of hydrazide-activated protein to a pH of from 10.0 to 11.0.

17. The method of claim 1, wherein 2 to 28 cyanate-activated immunogenic-distinct polysaccharides are simultaneously reacted with the at least one hydrazide-activated protein.

18. The method of claim 17, wherein the immunogenic-distinct polysaccharides are selected from the group consisting of Meningococcal polysaccharides, Pneumococcal polysaccharides, *Hemophilus influenzae* type b polysaccharide, Vi polysaccharide of *Salmonnella typhi* and group B *Streptococcus* polysaccharides.

19. The method of claim 1 wherein the immunogenic-distinct polysaccharides are selected from the group consisting of Meningococcal group A, Meningococcal group C, Meningococcal group W135 and Meningococcal group Y.

20. The method of claim 1 wherein the cyanate-activated immunogenic-distinct polysaccharides are reacted with a single hydrazide-activated protein.

21. The method of claim 1, wherein the cyanate-activated immunogenic-distinct polysaccharides are reacted with a plurality of different hydrazide-activated proteins.

22. The method of claim 13, wherein the carbodiimide is 1-[3-(dimethylamino)propyl]-3-ethyl carbodiimide hydrochloride.

23. The method of claim 15, wherein the carbodiimide is 1-[3-(dimethylamino)propyl]-3-ethyl carbodiimide hydrochloride.

24. The method of claim 1, wherein a mixture of immunogenic-distinct polysaccharides is reacted with the cyanylation agent.

25. The method of claim 1, wherein each immunogenic-distinct polysaccharide is initially reacted with the cyanylation agent, and then the resulting individual cyanate-activated immunogenic-distinct polysaccharides are mixed together to form the mixture of cyanate-activated immunogenic-distinct polysaccharides.

26. The method of claim 1, wherein the complex multivalent immunogenic conjugate comprises a structure having a plurality of immunogenic-distinct polysaccharides conjugated to a single protein construct.

27. The method of claim 1, wherein the complex multivalent immunogenic conjugate has a structure comprising:

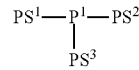

wherein $P^1$ is a carrier protein; and $PS^1$, $PS^2$, and $PS^3$ are each immunogenic-distinct polysaccharides that are covalently attached to $P^1$.

* * * * *